US012715931B2

(12) United States Patent
Chen et al.

(10) Patent No.: US 12,715,931 B2
(45) Date of Patent: Aug. 25, 2026

(54) NANOBODIES BINDING TROP2 AND USES THEREOF

(71) Applicant: BIOSION INC., Nanjing (CN)

(72) Inventors: Mingjiu Chen, Nanjing (CN); Mark Zhiqing Ma, Nanjing (CN)

(73) Assignee: BIOSION INC., Nanjing (CN)

( * ) Notice: Subject to any disclaimer, the term of this patent is extended or adjusted under 35 U.S.C. 154(b) by 628 days.

(21) Appl. No.: 18/250,800

(22) PCT Filed: Nov. 2, 2021

(86) PCT No.: PCT/CN2021/128204
§ 371 (c)(1),
(2) Date: Apr. 27, 2023

(87) PCT Pub. No.: WO2022/095851
PCT Pub. Date: May 12, 2022

(65) Prior Publication Data

US 2023/0383007 A1 Nov. 30, 2023

(30) Foreign Application Priority Data

Nov. 3, 2020 (CN) ........................ 202011209105.X

(51) Int. Cl.

| | |
|---|---|
| ***C07K 16/30*** | (2006.01) |
| ***A61K 47/68*** | (2017.01) |
| ***A61K 51/10*** | (2006.01) |

(52) U.S. Cl.
CPC .......... *C07K 16/30* (2013.01); *A61K 47/6817* (2017.08); *A61K 47/6851* (2017.08); *A61K 51/1045* (2013.01); *C07K 2317/24* (2013.01); *C07K 2317/569* (2013.01); *C07K 2317/92* (2013.01)

(58) Field of Classification Search
None
See application file for complete search history.

(56) References Cited

FOREIGN PATENT DOCUMENTS

| | | | |
|---|---|---|---|
| CN | 105849126 | A | 8/2016 |
| CN | 107446050 | A | 12/2017 |
| CN | 111518212 | A | 8/2020 |
| CN | 112321715 | A | 2/2021 |
| EP | 3088419 | A1 | 11/2016 |
| WO | 2015098099 | A | 7/2015 |
| WO | 2015126548 | A1 | 8/2015 |
| WO | 2013068946 | A | 12/2017 |
| WO | 2018157147 | A1 | 8/2018 |
| WO | 2020016662 | A2 | 1/2020 |
| WO | 2020191092 | A1 | 9/2020 |

OTHER PUBLICATIONS

Skkorodumova, 2024, Human Genome Var. vol. 11: 1-7.*
Rugo, et al., TROPiCS-02: A Phase III study investigating sacituzumab govitecan in the treatment of HR+/HER2-metastatic breast cancer, Future Oncology (Mar. 30, 2020) vol. 16. No. 12, p. 705-715.
ISR and Written Opinion issued Jan. 28, 2022 in International Application No. PCT/CN2021/128204.
CNIPA, First Office Action issued Nov. 16, 2021 to counterpart Chinese Application No. 202011209105.X.
JPO, Notice of Reasons for Refusal issued Oct. 7, 2025 to counterpart Japanese Application No. 2023526423.
EPO, Supplementary European Search Report and Written Opinion issued May 14, 2024 to counterpart European Application No. 21888548.1.

* cited by examiner

*Primary Examiner* — Amy E Juedes
(74) *Attorney, Agent, or Firm* — Duane Morris LLP; Thomas J. Kowalski

(57) ABSTRACT

A heavy chain only antibody that specifically binds human TROP2, or an antigen-binding portion thereof is provided. A nucleic acid molecule encoding the antibody or the antigen-binding portion thereof, an expression vector, a host cell and a method for expressing the antibody or the antigen-binding portion thereof are also provided. Further provided are an immunoconjugate and a pharmaceutical composition comprising the antibody or the antigen-binding portion thereof, as well as a treatment method using an anti-TROP2 antibody or the antigen-binding portion thereof.

19 Claims, 6 Drawing Sheets

Specification includes a Sequence Listing.

|  | 01-5A | 01-9F | TROP2 BM1 |
| --- | --- | --- | --- |
| EC50 | 17.71 | 20.83 | 37.37 |

|  | 01-5A | 01-9F | TROP2 BM1 |
| --- | --- | --- | --- |
| IC50 | 41.71 | 27.36 | 54.27 |

| | 01-9F | 01-5A | TROP2 BM1 |
|---|---|---|---|
| IC50 | 49.45 | 58.87 | 76.22 |

| | 01-9F | 01-9F-Fc | 01-9F-CDR-Fc-V5 |
|---|---|---|---|
| IC50 | 0.08608 | 0.06713 | 0.07566 |

| 01-9F-CDR-Fc-V6 | 01-9F-CDR-Fc-V9 | 01-9F-CDR-Fc-V11 | TROP2 BM1 |
|---|---|---|---|
| 0.106 | 0.06556 | 0.07994 | 0.1034 |

| | 01-9F-Fc-CDRV11-V1 | 01-9F-Fc-CDRV11-V9 | 01-9F-Fc-CDRV11-V11 | 01-9F | 01-9F-CDR-Fc-V11 | TROP2 BM1 |
|---|---|---|---|---|---|---|
| IC50 | 0.2662 | 0.2069 | 0.1782 | 0.1854 | 0.1601 | 0.1168 |

| | 01-9F-Fc-CDRV11-V11 | 01-9F | 01-9F-CDR-Fc-V11 | TROP2 BM1 |
|---|---|---|---|---|
| EC50 | 0.1691 | 0.1635 | 0.1504 | 0.2694 |

| | 01-9F-Fc-CDRV11-V11 | 01-9F | 01-9F-CDR-Fc-V11 | TROP2 BM1 |
|---|---|---|---|---|
| EC50 | 0.09592 | 0.1041 | 0.1129 | 0.162 |

| | 01-9F-Fc-CDRV11-V11 | 01-9F | 01-9F-CDR-Fc-V11 | TROP2 BM1 |
|---|---|---|---|---|
| EC50 | 0.09009 | 0.1073 | 0.1128 | 0.1612 |

| | 01-9F-Fc-CDRV11-V11 | 01-9F | 01-9F-CDR-Fc-V11 | TROP2 BM1 |
|---|---|---|---|---|
| EC50 | 0.3873 | 0.5299 | 0.4735 | 0.7059 |

| | 01-9F-Fc-CDRV11-V11 | 01-9F | 01-9F-CDR-Fc-V11 | TROP2 BM1 |
|---|---|---|---|---|
| IC50 | 0.2443 | 0.2467 | 0.198 | 0.5628 |

NANOBODIES BINDING TROP2 AND USES THEREOF

RELATED APPLICATIONS AND INCORPORATION BY REFERENCE

This application claims priority to Chinese Application No.: 202011209105.X filed on Nov. 3, 2020.

The foregoing applications, and all documents cited therein or during their prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

SEQUENCE STATEMENT

The instant application contains a Sequence Listing which has been submitted electronically and is hereby incorporated by reference in its entirety. Said ASCII copy was created Oct. 30, 2021, is named 55532_00102SL.txt and is 49,734 bytes in size.

FIELD OF THE INVENTION

The present disclosure relates generally to an isolated monoclonal heavy chain only antibody, or an antigen-binding portion thereof, that binds to human TROP2, with high affinity and functionality. A nucleic acid molecule encoding the antibody or the antigen-binding portion thereof, an expression vector, a host cell and a method for expressing the antibody or the antigen-binding portion thereof are also provided. The present disclosure further provides a bispecific molecule, an immunoconjugate, a chimeric antigen receptor, an oncolytic virus, and a pharmaceutical composition which may comprise the antibody or the antigen-binding portion thereof, as well as a treatment method using the anti-TROP2 antibody or the antigen-binding portion thereof of the disclosure.

BACKGROUND OF THE INVENTION

TROP2 is a transmembrane glycoprotein that is also known as epithelial glycoprotein-1 (EGP-1), membrane component surface marker-1 (M1S1), tumor-associated calcium signal transducer-2 (TACSTD2) and gastrointestinal antigen 733-1 (GA733-1). Each TROP2 molecule is composed of a hydrophobic precursor peptide, an extracellular domain, a transmembrane domain and a cytoplasmic tail. The cytoplasmic tail contains a highly conserved phosphatidylinositol 4,5-bisphosphate (PIP2) binding sequence and a serine phosphorylation site at position 303 (Zaman S et al., (2019) Targeting Trop-2 in solid tumors: future prospects. *Onco Targets Ther.* 12:1781-1790). The binding partners of TROP2 include IFG-1, Claudin-1, Claudin-7, cyclin D1 and PKC (Shvartsur A et al., (2015) Trop2 and its overexpression in cancers: regulation and clinical/therapeutic implications. *Genes Cancer.* 6(3-4):84-105).

TROP2 is expressed at low levels in normal tissues, playing a role in e.g., embryonic organ development and fetal growth, while upregulated TROP2 expression has been found in all cancer types independent of baseline TROP2 levels in normal counterparts (Mustata R C et al., (2013) Identification of Lgr5-independent spheroid-generating progenitors of the mouse fetal intestinal epithelium. *Cell Reports.* 5(2):421-432; Guerra E et al., (2012) mTrop1/Epcam knockout mice develop congenital tufting enteropathy through dysegulation of intestinal e-cadherin/β-catenin. *PLoS ONE.* 7(11): e49302; Trerotola M et al., (2013) Upregulation of Trop-2 quantitatively stimulates human cancer growth. *Oncogene.* 32(2): 222-233). Studies have shown several transcription factors on which TROP2 expression depends are correlated with cancer development, such as TP63/TP53L and Wilm's tumor 1 (WT1), and TROP2 is demonstrated to be involved in many cell signaling pathways associated with tumorigenesis. For example, TROP2 signaling regulates cell self-renewal and proliferation via β-catenin signaling, and thus promotes stem cell-like properties of cancer cells (Stoyanova T et al., (2012) Regulated proteolysis of Trop2 drives epithelial hyperplasia and stem cell self-renewal via β-catenin signaling. *Genes Dev.* 26(20):2271-2285). TROP2 overexpression promotes tumor invasion in cervical, ovarian, colon and thyroid cancers, and TROP2 knock-down decreases cancer cell invasion (Guan H et al., (2017) Trop2 enhances invasion of thyroid cancer by inducing MMP2 through ERK and JNK pathways. *BMC Cancer.* 17(1):486; Liu T et al., (2013) Overexpression of Trop2 predicts poor prognosis of patients with cervical cancer and promotes the proliferation and invasion of cervical cancer cells by regulating ERK signaling pathway. *PLoS One.* 8(9):e75864; Wu B et al., (2017) Overexpression of Trop2 promotes proliferation and invasion of ovarian cancer cells. *Exp Ther Med.* 14(3):1947-1952; Zhao P et al., (2018) TNF-α promotes colon cancer cell migration and invasion by upregulating Trop-2. *Oncol Lett.* 15(3):3820-3827). Recently, TROP2 signaling has been further found to modulate signaling for cell migration. For instance, it was reported that TROP2 regulates β1 integrin functions to promote prostate cancer metastasis (Trerotola M et al., (2013) Trop-2 promotes prostate cancer metastasis by modulating β(1) integrin functions. *Cancer Res.* 73(10):3155-3167).

High TROP2 expression has been clinically correlated with poor prognosis in e.g., hilar cholangiocarcinoma, cervical cancer, and gastric cancer. In a meta-analysis including 2,569 patients, TROP2 expression increase was statistically linked to poor overall and disease-free survival outcomes in several solid tumors (Fong D et al., (2008) High expression of Trop2 correlates with poor prognosis in pancreatic cancer. *Br J Cancer.* 99(8):1290-1295; Ning S et al., (2013) Trop2 correlates with microvessel density and poor prognosis in hilar cholangiocarcinoma. *J Gastrointest Surg.* 17(2):360-368; Liu T et al., (2013) Overexpression of Trop2 predicts poor prognosis of patients with cervical cancer and promotes the proliferation and invasion of cervical cancer cells by regulating ERK signaling pathway. *PLoS One.* 8(9):e75864; Zhao W et al., (2016) Trop2 is overexpressed in gastric cancer and predicts poor prognosis. Oncotarget. 7(5):6136-6145; Zeng P et al., (2016) Impact of Trop2 expression on prognosis in solid tumors: a systematic review and meta-analysis. *Sci Rep.* 6:33658). TROP2's role as a tumor marker is even being tested in a certain clinical trial.

Because of its structure characteristic and correlation with cancer, TROP2 is an attractive therapeutic target. Several anti-TROP2 antibodies were prepared, some were found to inhibit breast cancer progression and induce apoptosis in xenograft mouse model (Lin H et al., (2014) A novel human Fab antibody for Trop2 inhibits breast cancer growth in vitro and in vivo. *Int J Cancer.* 134(5):1239-1249). However, none showed therapeutic value as a naked antibody, probably due to their high internalization rates, until Pr1E11 was identified by IKEDA et al., in 2015 with higher binding affinity and lower internalization activity (Ikeda M et al., (2015) Pr1E11, a novel anti-TROP-2 antibody isolated by adenovirus-based antibody screening, recognizes a unique epitope. *Biochem Biophys Res Commun.* 458(4):877-82). Pr1E11 was determined in a later study to induce potent antibody-dependent cytotoxicity in vivo, which was presumed to be high cell surface retention related (Ikeda M et al., (2016) Cell Surface Antibody Retention Influences In Vivo Antitumor Activity Mediated by Antibody-dependent Cellular Cytotoxicity. *Anticancer Res.* 36(11):5937-5944). Currently, most TROP2 targeted therapeutics that are under pre-clinical and clinical trials are antibody-drug conjugates (ADCs), including DS-1062a, IMMU-132 and PF-06664178, with some encouraging outcomes obtained till now in solid cancer treatment with limited toxicity (Zaman S et al., (2019) supra).

There is a need for additional anti-TROP2 antibodies with low internalization activity to be used as naked antibodies or with high internalization activity for ADC preparation.

Citation or identification of any document in this application is not an admission that such document is available as prior art to the present invention.

SUMMARY OF THE INVENTION

The present disclosure provides an isolated heavy chain only antibody, or an antigen-binding portion thereof, that binds to TROP2 (e.g., human TROP2) and has comparable, if not higher, binding affinity/capability to human and/or monkey TROP2, and comparable, if not higher, internalization activity, as compared to prior art anti-TROP2 antibodies such as sacituzumab (the antibody part of IMMU-132).

The heavy chain only antibody or antigen-binding portion of the disclosure can be used for a variety of applications, including detection of TROP2 proteins in vitro and in vivo if radioactively labeled, and treatment of TROP2 related diseases, such as cancers.

Accordingly, in one aspect, the disclosure pertains to an isolated monoclonal heavy chain only antibody (e.g., a camelid, chimeric or humanized antibody), or an antigen-binding portion thereof, that binds TROP2, having a variable region that may comprise a VH CDR1 region, a VH CDR2 region and a VH CDR3 region, wherein the VH CDR1 region, the VH CDR2 region and the VH CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 2 (X1=D, X2=G, X3=D, X4=S) and 3 (X1=D, X2=G), respectively; (2) SEQ ID NOs: 1, 2 (X1=D, X2=G, X3=D, X4=S) and 3 (X1=E, X2=G), respectively; (3) SEQ ID NOs: 1, 2 (X1=D, X2=G, X3=D, X4=S) and 3 (X1=D, X2=A), respectively; (4) SEQ ID NOs: 1, 2 (X1=D, X2=G, X3=D, X4=S) and 3 (X1=I, X2=G), respectively; (5) SEQ ID NOs: 1, 2 (X1=E, X2=G, X3=D, X4=S) and 3 (X1=E, X2=G), respectively; (6) SEQ ID NOs: 1, 2 (X1=D, X2=A, X3=D, X4=S) and 3 (X1=E, X2=G), respectively; (7) SEQ ID NOs: 1, 2 (X1=E, X2=G, X3=D, X4=S) and 3 (X1=D, X2=A), respectively; (8) SEQ ID NOs: 1, 2 (X1=D, X2=A, X3=D, X4=S) and 3 (X1=D, X2=A), respectively; (9) SEQ ID NOs: 1, 2 (X1=E, X2=G, X3=E, X4=S) and 3 (X1=E, X2=G), respectively; (10) SEQ ID NOs: 1, 2 (X1=D, X2=A, X3=E, X4=S) and 3 (X1=E, X2=G), respectively; (11) SEQ ID NOs: 1, 2 (X1=E, X2=G, X3=D, X4=T) and 3 (X1=D, X2=A), respectively; or (12) SEQ ID NOs: 1, 2 (X1=D, X2=A, X3=D, X4=T) and 3 (X1=D, X2=A), respectively.

The isolated monoclonal heavy chain only antibody, or the antigen-binding portion thereof, of the present disclosure may comprise a variable region that may comprise an amino acid sequence having at least 85%, 86%, 87%, 88%, 89%, 90%, 91%, 92%, 93%, 94%, 95%, 96%, 97%, 98%, 99% or 100% identity to SEQ ID NO: 4 (X1=S, X2=Q, X3=D, X4=G, X5=P; X1=S, X2=Q, X3=E, X4=G, X5=P; X1=S, X2=Q, X3=D, X4=A, X5=P; X1=S, X2=Q, X3=I, X4=G, X5=P; or X1=T, X2=G, X3=D, X4=G, X5=L), 5 (X1=E, X2=G, X3=D; X1=D, X2=A, X3=D; X1=E, X2=G, X3=E; or X1=D, X2=A, X3=E); 6 (X1=E, X2=G, X3=S; X1=D, X2=A, X3=S; X1=E, X2=G, X3=T; or X1=D, X2=A, X3=T), 7, 8 (X1=F, X2=Y, X3=K, X4=A; X1=L, X2=F, X3=K, X4=A; X1=L, X2=Y, X3=R, X4=A; X1=L, X2=Y, X3=K, X4=R; or X1=L, X2=Y, X3=K, X4=A), 9 (X1=F, X2=Y, X3=K, X4=A; X1=L, X2=F, X3=K, X4=A; X1=L, X2=Y, X3=R, X4=A; X1=L, X2=Y, X3=K, X4=R; or X1=L, X2=Y, X3=K, X4=A), 10 (X1=F, X2=Y, X3=K, X4=A; X1=L, X2=F, X3=K, X4=A; X1=L, X2=Y, X3=R, X4=A; X1=L, X2=Y, X3=K, X4=R; or X1=L, X2=Y, X3=K, X4=A); 11 (X1=F, X2=Y, X3=K, X4=A; X1=L, X2=F, X3=K, X4=A; X1=L, X2=Y, X3=R, X4=A; X1=L, X2=Y, X3=K, X4=R; or X1=L, X2=Y, X3=K, X4=A), 12, or 13 (X1=V, X2=W; or X1=F, X2=G). The amino acid sequences of SEQ ID NOs: 4 (X1=S, X2=Q, X3=D, X4=G, X5=P), 6 (X1=D, X2=A, X3=T) and 9 (X1=L, X2=Y, X3=K, X4=A) may be encoded by the nucleotide sequences of SEQ ID NOs: 23, 24 and 25, respectively.

The isolated monoclonal heavy chain only antibody, or the antigen-binding portion thereof, of the present disclosure may comprise a constant region or a functional fragment thereof, linked to the variable region, wherein the C terminus of the variable region is linked to the N terminus of the constant region. The constant region may be a heavy chain constant region with enhanced FcR binding capability, such as human IgG1 heavy chain constant region or a functional fragment thereof having the amino acid sequence set forth in e.g., SEQ ID NO.: 14. The heavy chain constant region may also be human IgG2 or IgG4 constant region or a functional fragment thereof engineered to have enhanced FcR binding affinity. The amino acid sequence of SEQ ID NO: 14 may be encoded by the nucleotide sequence of SEQ ID NO: 26.

The disclosure also provides a bispecific molecule that may comprise the heavy chain only antibody, or the antigen-binding portion thereof, of the disclosure, linked to a second functional moiety (e.g., a second antibody) having a different binding specificity than said antibody, or antigen-binding portion thereof. The disclosure also provides an immunoconjugate that may comprise a heavy chain only antibody, or antigen-binding portion thereof, of the disclosure, linked to a therapeutic agent, such as a cytotoxin, e.g., SN-38, or a radioactive label. The heavy chain only antibody or the antigen binding portion thereof of the present disclosure can be made into part of a chimeric antigen receptor (CAR). Also provided is an immune cell that may comprise the antigen chimeric receptor, such as a T cell and a NK cell. The heavy chain only antibody or the antigen binding portion thereof of the present disclosure can also be encoded by or used in conjunction with an oncolytic virus.

The heavy chain only antibody or antigen-binding portion thereof, the immunoconjugate, or the bispecific molecule may be radioactively labeled and used in clinical imaging to e.g., trace/detect the distribution of tumors/cancers, including distribution of metastatic tumors/cancers. The radioactive label includes, but not limited to, $^{3}H$.

Nucleic acid molecules encoding the heavy chain only antibody, or the antigen-binding portion thereof, the bispecific molecule, the immunoconjugate, or the CAR of the disclosure are also encompassed by the disclosure, as well as expression vectors that may comprise such nucleic acids and host cells that may comprise such expression vectors. A method for preparing the anti-TROP2 heavy chain only antibody or the antigen-binding portion thereof of the disclosure using the host cell is also provided, that may comprise steps of (i) expressing the antibody or antigen-binding portion thereof in the host cell and (ii) isolating the antibody or antigen-binding portion thereof from the host cell or its cell culture.

Pharmaceutical compositions that may comprise the heavy chain only antibody, or the antigen-binding portion thereof, the immunoconjugate, the bispecific molecule, the oncolytic virus, the CAR or CAR-T cell, the nucleic acid molecule, the expression vector, or the host cell of the disclosure, and a pharmaceutically acceptable carrier, are also provided. In certain embodiments, the pharmaceutical composition may further contain a therapeutic agent for treating a specific disease, such as an anti-cancer agent.

In yet another aspect, the disclosure provides a method for treating a disease associated with TROP2 (e.g., excessive TROP2 expression) in a subject in need thereof, which may comprise administering to a subject a therapeutically effective amount of the pharmaceutical composition of the present disclosure. The disease may be a tumor or cancer. The tumor may be a solid tumor or a non-solid tumor, including, but not limited to, breast cancer, colorectal cancer, gastric adenocarcinoma, esophageal cancer, hepatocellular carcinoma, non-small-cell lung cancer, small-cell lung cancer, ovarian epithelial cancer, prostate cancer, pancreatic ductal adenocarcinoma, head and neck cancer, squamous cell cancer, renal cell cancer, urinary bladder neoplasm, cervical cancer, endometrial cancer, follicular thyroid cancer, and glioblastoma multiforme. In certain embodiments, at least one additional anti-cancer antibody may be further administered, such as an anti-VISTA antibody, an anti-PD-1 antibody, an anti-PD-L1 antibody, an anti-LAG-3 antibody, an anti-CTLA-4 antibody, an anti-TIM3 antibody, an anti-STAT3 antibody, and/or an anti-ROR1 antibody. In certain embodiments, the subject is human.

In another aspect, the disclosure provides a method for cancer imaging in a subject in need thereof, comprising administering the subject with a radioactively labeled anti-TROP2 heavy chain only antibody or antigen-binding portion thereof, the immunoconjugate, or the bispecific molecule of the disclosure. The method may be used to trace/detect the distribution of a tumor or cancer with high TROP2 expression, including, but not limited to, esophageal squamous cell carcinoma, colorectal cancer, pancreatic cancer, colon cancer, papillary thyroid cancer, breast cancer, and bladder cancer. In certain embodiments, the subject is human.

Other features and advantages of the instant disclosure will be apparent from the following detailed description and examples, which should not be construed as limiting. The contents of all references, Genbank entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
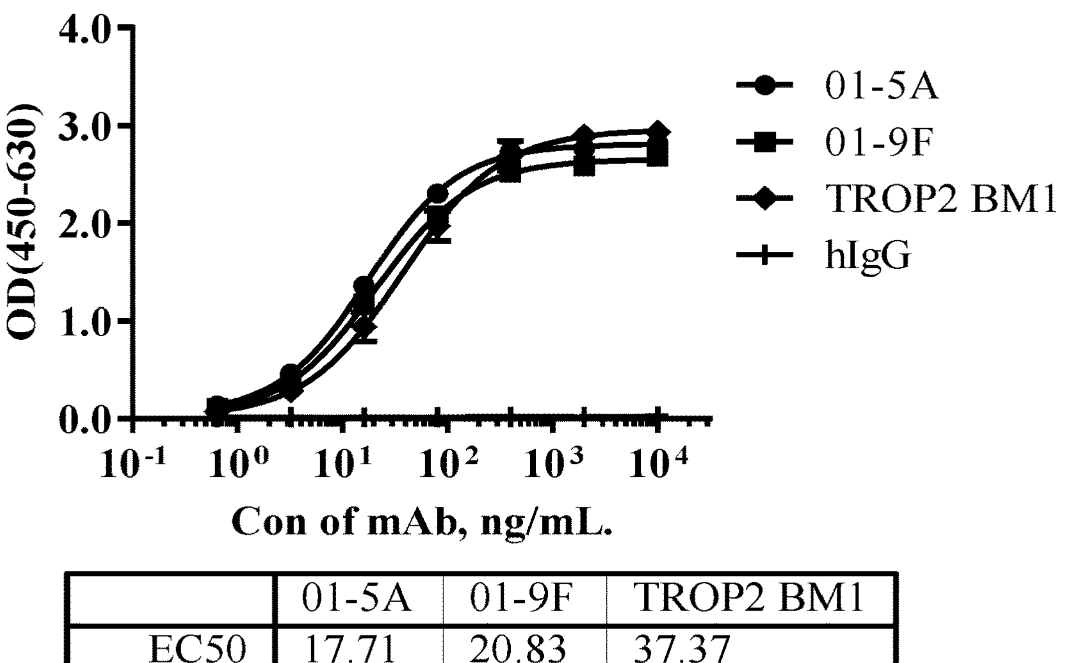
FIG. 1 shows the binding capabilities of single domain antibodies 01-9F and 01-5A to human TROP2 in an indirect ELISA.

To ensure that the present disclosure may be more readily understood, certain terms are first defined. Additional definitions are set forth throughout the detailed description.

The term "TROP2" refers to tumor-associated calcium signal transducer 2, also known as epithelial glycoprotein-1, gastrointestinal antigen 733-1 and membrane component surface marker-1. The term "TROP2" may comprise variants, isoforms, homologs, orthologs and paralogs. For example, an antibody specific for a human TROP2 protein may, in certain cases, cross-react with a TROP2 protein from a species other than human, such as monkey. In other embodiments, an antibody specific for a human TROP2 protein may be completely specific for the human TROP2 protein and exhibit no cross-reactivity to other species or of other types, or may cross-react with TROP2 from certain other species but not all other species.

The term "human TROP2" refers to a TROP2 protein having an amino acid sequence from a human, such as the amino acid sequence of human TROP2 set forth in SEQ ID NO: 20. The terms "monkey TROP2" or "cynomolgus TROP2" refer to a TROP2 protein having an amino acid sequence from *Macaca nemestrina* or *Macaca mulatta*, such as the amino acid sequence having NCBI Accession No. XP_001114599.1 or XP_011762693.1.

In some instances, the term "antibody" specifically refers to a heavy chain only antibody or the antigen-binding portion thereof, of the disclosure. The term "heavy chain only antibody" or "HCAb" refers to a functional antibody, which comprises heavy chains only, but lacks the light chains usually found in a 4-chain immunoglobulin. The naturally occurring heavy chain only antibodies are found in e.g., camelids (such as camels, llamas, or alpacas). Each camelid heavy chain only antibody contains a heavy chain variable region/domain, called $V_HH$ domain, $V_HH$ fragment or single chain antibody (sdAb), and a heavy chain constant region. The $V_HH$ functions to interact with an antigen. The $V_HH$ contains three complementarity determining regions (CDRs) and four framework regions (FRs), arranged from amino-terminus to carboxy-terminus in the following order: FR1, CDR1, FR2, CDR2, FR3, CDR3, FR4. The heavy chain constant region contains a hinge region, a CH2 domain and a CH3 domain. The lacking $C_H1$ domain is replaced with an extended hinge region. In a chimeric or humanized heavy chain only antibody, the heavy chain constant region may contain a typical IgG, such as IgG1, IgG2 or IgG4, constant region. The constant region may mediate the binding of the heavy chain only antibody to host tissues or factors, including various cells of the immune system (e.g., effector cells) and the first component (C1q) of the classical complement system.

The "antigen binding portion" as used in connection with a heavy chain only antibody refers to one or more fragments of a heavy chain only antibody that retain the ability to specifically bind to an antigen (e.g., TROP2). It has been shown that the antigen-binding function of a heavy chain antibody can be performed by fragments of a full-length heavy chain only antibody. Examples of "antigen-binding portions of a heavy chain only antibody include, but not limited to, (i) an isolated complementarity determining region (CDR); (ii) a monovalent $V_HH$ fragment; (iii) a bivalent fragment comprising two monovalent $V_HH$ fragments; (iv) a monovalent fragment comprising a $V_HH$ fragment linked to a partial heavy chain constant region, such as a $V_HH$ domain linked to the CH2 domain, or CH2 and CH3 domains of a heavy chain constant region; (v) a bivalent fragment comprising two $V_HH$ fragments each linked to a partial heavy chain constant region; (vi) multiple monovalent $V_HH$ domains linked with or without linkers. The term "single domain antibody", "sdAb", or "nanoantibody" refers to a single antigen-binding polypeptide comprising a single monomeric variable antibody domain having three complementary determining regions (CDRs), which is capable of binding to an antigen without pairing with a corresponding CDR-containing polypeptide. In some cases, the single domain antibody is engineered from a camelid HCAb, and is also called the $V_HH$ domain or fragment of the HCAb. The single domain antibody is a kind of antigen-binding portion of a heavy chain only antibody. The $V_HHs$ may also be known as nanobodies. Camelid sdAb is one of the smallest known antigen binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)).

An "isolated antibody", as used herein, is intended to refer to an antibody that is substantially free of other antibodies having different antigenic specificities (e.g., an isolated antibody that specifically binds a TROP2 protein is substantially free of antibodies that specifically bind antigens other than TROP2 proteins). An isolated antibody that specifically binds a human TROP2 protein may, however, have cross-reactivity to other antigens, such as TROP2 proteins from other species. Moreover, an isolated antibody can be substantially free of other cellular material and/or chemicals.

The term "camelid antibody", as used herein, is intended to include antibodies having variable regions in which both the framework and CDR regions are derived from camelid germline immunoglobulin sequences. Furthermore, if the antibody contains a constant region, the constant region also is derived from camelid germline immunoglobulin sequences. The camelid antibodies of the disclosure can include amino acid residues not encoded by camelid germline immunoglobulin sequences (e.g., mutations introduced by random or site-specific mutagenesis in vitro or by somatic mutation in vivo). However, the term "camelid antibody", as used herein, is not intended to include antibodies in which CDR sequences derived from the germline of another mammalian species have been grafted onto camelid framework sequences.

The term "chimeric antibody" refers to an antibody made by combining genetic material from a nonhuman source with genetic material from a human being. Or more generally, a chimeric antibody is an antibody having genetic material from a certain species with genetic material from another species.

The term "humanized antibody", as used herein, refers to an antibody from non-human species whose protein sequences have been modified to increase similarity to antibody variants produced naturally in humans.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human TROP2" is intended to refer to an antibody that binds to human TROP2 protein (and possibly a TROP2 protein from one or more non-human species) but does not substantially bind to non-TROP2 proteins. Preferably, the antibody binds to human TROP2 protein with "high affinity", namely with a $K_D$ of $5.0\times10^{-8}$ M or less, more preferably $1.0\times10^{-8}$ M or less, and more preferably $2.0\times10^{-9}$ M or less.

The term "does not substantially bind" to a protein or cells, as used herein, means does not bind or does not bind with a high affinity to the protein or cells, i.e. binds to the protein or cells with a $K_D$ of $1.0\times10^{-6}$ M or more, more preferably $1.0\times10^{-5}$ M or more, more preferably $1.0\times10^{-4}$ M or more, more preferably $1.0\times10^{-3}$ M or more, even more preferably $1.0\times10^{-2}$ M or more.

The term "high affinity" for an IgG antibody refers to an antibody having a $K_D$ of $1.0\times10^{-6}$ M or less, more preferably $5.0\times10^{-8}$ M or less, even more preferably $1.0\times10^{-8}$ M or less, even more preferably $1.0\times10^{-9}$ M or less and even more preferably $5.0\times10^{-10}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "$EC_{50}$", also known as half maximal effective concentration, refers to the concentration of an antibody which induces a response halfway between the baseline and maximum after a specified exposure time.

The term "$IC_{50}$", also known as half maximal inhibitory concentration, refers to the concentration of an antibody which inhibits a specific biological or biochemical function by 50% relative to the absence of the antibody.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody or the antigen binding portion of the present disclosure sufficient to prevent or ameliorate the symptoms associated with a disease or condition (such as a chronic inflammation) and/or lessen the severity of the disease or condition. A therapeutically effective amount is understood to be in context to the condition being treated, where the actual effective amount is readily discerned by those of skill in the art.

Various aspects of the disclosure are described in further detail in the following subsections.

The heavy chain only antibody, or the antigen-binding portion thereof, of the disclosure specifically binds to human TROP2 with comparable, if not higher, binding affinity/capability to human and/or monkey TROP2, and has comparable, if not higher, internalization activity, as compared to prior art anti-TROP2 antibodies such as sacituzumab (the antibody part of IMMU-132).

The antibodies or antigen-binding portions thereof of the disclosure are camelid, chimeric and humanized. The antibodies of the disclosure are heavy chain-only antibodies.

TABLE 1

Amino acid sequence ID numbers of heavy/light chain variable regions and CDRs of heavy chain only antibodies

| Antibody ID | $V_H$-CDR1 | $V_H$-CDR2 | $V_H$-CDR3 | $V_H$ |
|---|---|---|---|---|
| 01-9F | 1 | 2, X1 = D, X2 = G, X3 = D, X4 = S | 3, X1 = D, X2 = G | 4, X1 = S, X2 = Q, X3 = D, X4 = G, X5 = P |
| 01-9F-CDR-V1 | 1 | 2, X1 = D, X2 = G, X3 = D, X4 = S | 3, X1 = E, X2 = G | 4, X1 = S, X2 = Q, X3 = E, X4 = G, X5 = P |
| 01-9F-CDR-V2 | 1 | 2, X1 = D, X2 = G, X3 = D, X4 = S | 3, X1 = D, X2 = A | 4, X1 = S, X2 = Q, X3 = D, X4 = A, X5 = P |
| 01-9F-CDR-V3 | 1 | 2, X1 = D, X2 = G, X3 = D, X4 = S | 3, X1 = I, X2 = G | 4, X1 = S, X2 = Q, X3 = I, X4 = G, X5 = P |
| 01-9F-CDR-V4 | 1 | 2, X1 = E, X2 = G, X3 = D, X4 = S | 3, X1 = E, X2 = G | 5, X1 = E, X2 = G, X3 = D |
| 01-9F-CDR-V5 | 1 | 2, X1 = D, X2 = A, X3 = D, X4 = S | 3, X1 = E, X2 = G | 5, X1 = D, X2 = A, X3 = D |
| 01-9F-CDR-V6 | 1 | 2, X1 = E, X2 = G, X3 = D, X4 = S | 3, X1 = D, X2 = A | 6, X1 = E, X2 = G, X3 = S |
| 01-9F-CDR-V7 | 1 | 2, X1 = D, X2 = A, X3 = D, X4 = S | 3, X1 = D, X2 = A | 6, X1 = D, X2 = A, X3 = S |
| 01-9F-CDR-V8 | 1 | 2, X1 = E, X2 = G, X3 = E, X4 = S | 3, X1 = E, X2 = G | 5, X1 = E, X2 = G, X3 = E |
| 01-9F-CDR-V9 | 1 | 2, X1 = D, X2 = A, X3 = E, X4 = S | 3, X1 = E, X2 = G | 5, X1 = D, X2 = A, X3 = E |
| 01-9F-CDR-V10 | 1 | 2, X1 = E, X2 = G, X3 = D, X4 = T | 3, X1 = D, X2 = A | 6, X1 = E, X2 = G, X3 = T |

TABLE 1-continued

| Amino acid sequence ID numbers of heavy/light chain variable regions and CDRs of heavy chain only antibodies | | | | |
|---|---|---|---|---|
| Antibody ID | $V_H$-CDR1 | $V_H$-CDR2 | $V_H$-CDR3 | $V_H$H |
| 01-9F-CDR-V11 | 1 | 2, X1 = D, X2 = A, X3 = D, X4 = T | 3, X1 = D, X2 = A | 6, X1 = D, X2 = A, X3 = T |
| 01-9F-CDR-V11-V1 | 1 | 2, X1 = D, X2 = A, X3 = D, X4 = T | 3, X1 = D, X2 = A | 7 |
| 01-9F-CDR-V11-V2 | 1 | 2, X1 = D, X2 = A, X3 = D, X4 = T | 3, X1 = D, X2 = A | 8, X1 = F, X2 = Y, X3 = K, X4 = A |
| 01-9F-CDR-V11-V3 | 1 | 2, X1 = D, X2 = A, X3 = D, X4 = T | 3, X1 = D, X2 = A | 8, X1 = L, X2 = F, X3 = K, X4 = A |
| 01-9F-CDR-V11-V4 | 1 | 2, X1 = D, X2 = A, X3 = D, X4 = T | 3, X1 = D, X2 = A | 8, X1 = L, X2 = Y, X3 = R, X4 = A |
| 01-9F-CDR-V11-V5 | 1 | 2, X1 = D, X2 = A, X3 = D, X4 = T | 3, X1 = D, X2 = A | 8, X1 = L, X2 = Y, X3 = K, X4 = R |
| 01-9F-CDR-V11-V6 | 1 | 2, X1 = D, X2 = A, X3 = D, X4 = T | 3, X1 = D, X2 = A | 8, X1 = L, X2 = Y, X3 = K, X4 = A |
| 01-9F-CDR-V11-V7 | 1 | 2, X1 = D, X2 = A, X3 = D, X4 = T | 3, X1 = D, X2 = A | 9, X1 = F, X2 = Y, X3 = K, X4 = A |
| 01-9F-CDR-V11-V8 | 1 | 2, X1 = D, X2 = A, X3 = D, X4 = T | 3, X1 = D, X2 = A | 9, X1 = L, X2 = F, X3 = K, X4 = A |
| 01-9F-CDR-V11-V9 | 1 | 2, X1 = D, X2 = A, X3 = D, X4 = T | 3, X1 = D, X2 = A | 9, X1 = L, X2 = Y, X3 = R, X4 = A |
| 01-9F-CDR-V11-V10 | 1 | 2, X1 = D, X2 = A, X3 = D, X4 = T | 3, X1 = D, X2 = A | 9, X1 = L, X2 = Y, X3 = K, X4 = R |
| 01-9F-CDR-V11-V11 | 1 | 2, X1 = D, X2 = A, X3 = D, X4 = T | 3, X1 = D, X2 = A | 9, X1 = L, X2 = Y, X3 = K, X4 = A |
| 01-9F-CDR-V11-V12 | 1 | 2, X1 = D, X2 = A, X3 = D, X4 = T | 3, X1 = D, X2 = A | 10, X1 = F, X2 = Y, X3 = K, X4 = A |
| 01-9F-CDR-V11-V13 | 1 | 2, X1 = D, X2 = A, X3 = D, X4 = T | 3, X1 = D, X2 = A | 10, X1 = L, X2 = F, X3 = K, X4 = A |
| 01-9F-CDR-V11-V14 | 1 | 2, X1 = D, X2 = A, X3 = D, X4 = T | 3, X1 = D, X2 = A | 10, X1 = L, X2 = Y, X3 = R, X4 = A |
| 01-9F-CDR-V11-V15 | 1 | 2, X1 = D, X2 = A, X3 = D, X4 = T | 3, X1 = D, X2 = A | 10, X1 = L, X2 = Y, X3 = K, X4 = R |
| 01-9F-CDR-V11-V16 | 1 | 2, X1 = D, X2 = A, X3 = D, X4 = T | 3, X1 = D, X2 = A | 10, X1 = L, X2 = Y, X3 = K, X4 = A |
| 01-9F-CDR-V11-V17 | 1 | 2, X1 = D, X2 = A, X3 = D, X4 = T | 3, X1 = D, X2 = A | 11, X1 = F, X2 = Y, X3 = K, X4 = A |
| 01-9F-CDR-V11-V18 | 1 | 2, X1 = D, X2 = A, X3 = D, X4 = T | 3, X1 = D, X2 = A | 11, X1 = L, X2 = F, X3 = K, X4 = A |
| 01-9F-CDR-V11-V19 | 1 | 2, X1 = D, X2 = A, X3 = D, X4 = T | 3, X1 = D, X2 = A | 11, X1 = L, X2 = Y, X3 = R, X4 = A |
| 01-9F-CDR-V11-V20 | 1 | 2, X1 = D, X2 = A, X3 = D, X4 = T | 3, X1 = D, X2 = A | 11, X1 = L, X2 = Y, X3 = K, X4 = R |
| 01-9F-CDR-V11-V21 | 1 | 2, X1 = D, X2 = A, X3 = D, X4 = T | 3, X1 = D, X2 = A | 11, X1 = L, X2 = Y, X3 = K, X4 = A |
| 01-9F-CDR-V11-V22 | 1 | 2, X1 = D, X2 = A, X3 = D, X4 = T | 3, X1 = D, X2 = A | 12 |
| 01-9F-CDR-V11-V23 | 1 | 2, X1 = D, X2 = A, X3 = D, X4 = T | 3, X1 = D, X2 = A | 13, X1 = V, X2 = W |
| 01-9F-CDR-V11-V24 | 1 | 2, X1 = D, X2 = A, X3 = D, X4 = T | 3, X1 = D, X2 = A | 13, X1 = F, X2 = G |
| 01-5A | 1 | 2, X1 = D, X2 = G, X3 = D, X4 = S | 3, X1 = D, X2 = G | 4, X1 = T, X2 = G, X3 = D, X4 = G, X5 = L |

The antibodies with Fc regions can be referred to as 01-9F-CDR-Vn-Fc (or 01-9F-CDR-Fc-Vn (n = 1-11)) and 01-9F-CDR-V11-Vn-Fc (or 01-9F-Fc-CDRV11-Vn (n = 1-24)) herein.

The antibody or antigen-binding portion thereof of the disclosure is the monoclonal antibody structurally and chemically characterized as described below and in the following Examples. The amino acid sequence ID numbers of the variable regions and CDRs of the disclosure are summarized in Table 1, some antibodies sharing the same $V_H$H. The constant region for the antibodies may be a heavy chain constant region or a functional fragment thereof comprising the amino acid sequence of e.g., SEQ ID NO: 14. The antibodies of the disclosure may also contain human IgG1, IgG2 or IgG4 heavy chain constant region.

The variable region CDRs in Table 1 have been defined by the Kabat numbering system. However, as is well known in the art, CDR regions can also be determined by other systems such as Chothia, and IMGT, AbM, or Contact numbering system/method, based on variable region sequences.

The $V_H$H sequences (or CDR sequences) of other Anti-TROP2 antibodies which bind to human TROP2 can be "mixed and matched" with the $V_H$H sequences (or CDR sequences) of the anti-TROP2 antibody of the present disclosure.

Accordingly, in one embodiment, an antibody of the disclosure, or an antigen binding portion thereof, may comprise a variable region which may comprise an amino acid sequence listed above in Table 1, wherein the antibody specifically binds human TROP2.

In another embodiment, an antibody of the disclosure, or an antigen binding portion thereof, may comprise the CDR1, CDR2, and CDR3 regions of the heavy chain variable region listed above in Table 1, wherein the antibody specifically binds human TROP2.

In yet another embodiment, the antibody, or antigen binding portion thereof, includes the CDR2 region of anti-TROP2 antibody combined with CDRs of other antibodies which bind human TROP2, e.g., CDR1 and/or CDR3 from the variable region of a different anti-TROP2 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIA journal* 8: *Scientific Review* 8 (2001); Igarashi et al., *J. Biochem* (Tokyo) 117:452-7 (1995); Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

The antibody of the present disclosure possesses one or more of the following functional properties described above, such as high affinity binding to human TROP2.

In various embodiments, the antibody can be, for example, a camel, chimeric, or humanized antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

Antibodies of the disclosure can be prepared using an antibody having the $V_H$H sequences of the anti-TROP2 antibody of the present disclosure as starting material to engineer a modified antibody. An antibody can be engineered by modifying one or more residues within the variable region (i.e., $V_H$H), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the three complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad.* See also U.S.A. 86:10029-10033; U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, which may comprise a variable region that may comprise CDR1, CDR2, and CDR3 sequences which may comprise the sequences of the present disclosure, as described above, as described above. While these antibodies contain the $V_H$H CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo12 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the disclosure. The $V_H$H CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$H CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the disclosure provides isolated anti-TROP2 monoclonal antibodies, or antigen binding portions thereof, which may comprise a variable region that may comprise: (a) a CDR1 region which may comprise the sequence of the present disclosure, or an amino acid sequence having one, two, three, four or five amino acid substitutions, deletions or additions; (b) a CDR2 region which may comprise the sequence of the present disclosure, or an amino acid sequence having one, two, three, four or five amino acid substitutions, deletions or additions; (c) a CDR3 region which may comprise the sequence of the present disclosure, or an amino acid sequence having one, two, three, four or five amino acid substitutions, deletions or additions.

Engineered antibodies of the disclosure include those in which modifications have been made to framework residues within $V_H$H, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase or reduce the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 (α (1, 6)-fucosyltransferase), such that antibodies expressed in the Ms704, Ms705, and Ms709 cell lines lack fucose on their carbohydrates. The Ms704, Ms705, and Ms709 FUT8−/−cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1, 6 bond-related enzyme. EP 1,176,195 also describes cell lines which have a low enzyme activity for adding fucose to the N-acetylglucosamine that binds to the Fe region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. Methods for production of antibodies in a plant system are disclosed in the U.S. patent application 60/836,998, filed on Aug. 11, 2006. The fucose residues of the antibody can be cleaved off using a fucosidase enzyme; e.g., the fucosidase α-L-fucosidase removes fucosyl residues from antibodies (Tarentino et al., (1975) *Biochem.* 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EP 0 154 316 and EP 0 401 384.

Antibodies of the disclosure can be characterized by their various physical properties, to detect and/or differentiate different classes thereof.

For example, antibodies can contain one or more glycosylation sites in the variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al., (2000) *Mol Immunol* 37:697-706). Glycosylation has been known to occur at motifs containing an N-X-S/T sequence. In some instances, it is preferred to have an anti-TROP2 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a link into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-TROP2 antibody that contains a pI value that falls in the normal range. This can be achieved either by selecting antibodies with a pI in the normal range or by mutating charged surface residues.

In another aspect, the disclosure provides nucleic acid molecules that encode the variable regions, or CDRs, of the antibodies of the disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the heavy chain of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$H sequences of the TROP2 monoclonal antibody or the CDRs. Once DNA fragments encoding $V_H$H segments are obtained, these DNA fragments can be further manipulated by standard recombinant DNA techniques, for example to convert the variable region genes to full-length antibody chain genes, or to $V_H$H fragment genes.

The isolated DNA encoding the $V_H$H region can be converted to a full-length heavy chain gene by operatively linking the $V_H$-encoding DNA to another DNA molecule encoding heavy chain constant regions ($C_H$1, $CH_2$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region.

Monoclonal antibodies (mAbs) of the present disclosure can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Antibodies of the disclosure also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length heavy chain obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyomavirus enhancer. Alternatively, non-viral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the heavy chains, the expression vector(s) encoding the heavy chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the disclosure include Chinese Hamster Ovary (CHO cells) (including dhfr-CHO cells, described in Urlaub and Chasm, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

In another aspect, the present disclosure features bispecific molecules which may comprise one or more antibodies of the disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to the FcR binding specificity and an anti-TROP2 binding specificity, a third specificity.

In yet another aspect, the invention provides diagnostic methods, compositions and kits. In an embodiment, an antibody or an antigen-binding portion of the invention is used to determine the presence and expression of TROP2 in a tissue. In an embodiment, the diagnostic indicates prognosis and/or directs treatment and/or follow-up treatment. For example, TROP2 signaling has been targeted for treatment of tumors. In an embodiment, an antibody or an antigen binding portion of the invention is employed in diagnostic kit or method to determine prognosis and appropriate treatment and follow-up of TROP2 related tumors or cancers.

Antibodies of the disclosure can be conjugated to a therapeutic agent, a cytotoxin, or a radioactive label, to form an immunoconjugate. The cytotoxin may be a recombinant protein termed DT3C, having e.g., the amino acid sequence of SEQ ID NO: 22.

An oncolytic virus preferentially infects and kills cancer cells. Antibodies of the present disclosure can be used in conjunction with oncolytic viruses. Alternatively, oncolytic viruses encoding antibodies of the present disclosure can be introduced into human body.

Also provided herein are a chimeric antigen receptor (CAR) containing an anti-TROP2 $V_H$H fragment, the anti-TROP2 $V_H$H may comprise CDRs and heavy chain variable regions described herein.

The anti-TROP2 CAR may comprise (a) an extracellular antigen binding domain which may comprise an anti-TROP2 $V_H$H; (b) a transmembrane domain; and (c) an intracellular signaling domain.

The CAR may contain a signal peptide at the N-terminus of the extracellular antigen binding domain that directs the nascent receptor into the endoplasmic reticulum, and a hinge peptide at the N-terminus of the extracellular antigen binding domain that makes the receptor more available for binding. The CAR preferably comprises, at the intracellular signaling domain, a primary intracellular signaling domain and one or more co-stimulatory signaling domains. The mainly used and most effective primary intracellular signaling domain is CD3-zeta cytoplasmic domain which contains ITAMs, the phosphorylation of which results in T cell activation. The co-stimulatory signaling domain may be derived from the co-stimulatory proteins such as CD28, CD137 and OX40.

The CARs may further add factors that enhance T cell expansion, persistence, and anti-tumor activity, such as cytokines, and co-stimulatory ligands.

Also provided are engineered immune effector cells, which may comprise the CAR provided herein. In certain embodiments, the immune effector cell is a T cell, an NK cell, a peripheral blood mononuclear cell (PBMC), a hematopoietic stem cell, a pluripotent stem cell, or an embryonic stem cell. In certain embodiments, the immune effector cell is a T cell.

In another aspect, the present disclosure provides a pharmaceutical composition which may comprise one or more antibodies (or antigen-binding portions thereof, the bispecifics, CAR-T cells, oncolytic viruses, immunoconjugates, or alternatively nucleic acid molecules or the expression vectors of the disclosure capable of expressing the same) of the present disclosure formulated together with a pharmaceutically acceptable carrier. The antibodies (or antigen-binding portions thereof, the bispecifics, CAR-T cells, oncolytic viruses, immunoconjugates, or alternatively nucleic acid molecules or the expression vectors of the disclosure capable of expressing the same) can be dosed separately when the composition contains more than one antibody (or antigen-binding portion thereof, bispecific, CAR-T cell, oncolytic virus, immunoconjugate, or alternatively nucleic acid molecule or expression vector of the disclosure capable of expressing the same). The composition may optionally contain one or more additional pharmaceutically active ingredients, such as another antibody or a drug, such as an anti-tumor drug.

The pharmaceutical composition may comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: The Science and Practice of Pharmacy, 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion. Alternatively, an antibody of the disclosure can be administered via a non-parenteral route, such as a topical, epidermal or mucosal route of administration, e.g., intranasally, orally, vaginally, rectally, sublingually or topically.

Pharmaceutical compositions can be in the form of sterile aqueous solutions or dispersions. They can also be formulated in a micro-emulsion, liposome, or other ordered structure suitable to high drug concentration.

The amount of active ingredient which can be combined with a cater material to produce a single dosage form will vary depending upon the subject being treated and the particular mode of administration and will generally be that amount of the composition which produces a therapeutic effect. Generally, out of one hundred percent, this amount will range from about 0.010% to about ninety-nine percent of active ingredient.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the composition, the dosage may range from about 0.0001 to 100 mg/kg. An exemplary treatment regime entails administration once a month.

A "therapeutically effective dosage" of an anti-TROP2 antibody, or the antigen-binding portion thereof, or the bispecifics, CAR-T cells, oncolytic viruses, immunoconjugates of the disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably eliminate inflammations by at least about 20%, more preferably by at least about 40%, even more preferably by at least about 60%, and still more preferably by at least about 80% relative to untreated subjects.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies of the disclosure can be formulated to ensure proper distribution in vivo. For example, to ensure that the therapeutic antibody or antigen-binding portion thereof of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS Lett.* 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) *Immunomethods* 4:273.

The pharmaceutical composition which may comprise the antibodies or the antigen-binding portion thereof, or the bispecifics, CAR-T cells, oncolytic viruses, immunoconjugates, or alternatively a nucleic acid molecule or a vector of the disclosure capable of expressing the same of the present disclosure have numerous in vitro and in vivo utilities involving, for example, treatment of tumors with excessive TROP2 signaling.

Given that the TROP2 is associated with tumor cell proliferation, the disclosure provides methods for treating TROP2 related tumors or cancers, which may comprise administering to the subject the pharmaceutical composition of the disclosure. The tumor may be a solid tumor or a hematological tumor, including, but not limited to, breast cancer, colorectal cancer, gastric adenocarcinoma, esophageal cancer, hepatocellular carcinoma, non-small-cell lung cancer, small-cell lung cancer, ovarian epithelial cancer, prostate cancer, pancreatic ductal adenocarcinoma, head and neck cancer, squamous cell cancer, renal cell cancer, urinary bladder neoplasm, cervical cancer, endometrial cancer, follicular thyroid cancer, and glioblastoma multiforme. In certain embodiments, at least one additional anti-cancer antibody may be further administered, such as an anti-VISTA antibody, an anti-PD-1 antibody, an anti-PD-L1 antibody, an anti-LAG-3 antibody, an anti-CTLA-4 antibody, an anti-TIM 3 antibody, an anti-STAT3 antibody, and/or an anti-ROR1 antibody. In certain embodiments, the subject is human.

In another aspect, the disclosure provides methods of combination therapy in which the pharmaceutical composition of the present disclosure is co-administered with one or more additional antibodies that are effective in inhibiting tumor growth in a subject. In one embodiment, the disclosure provides a method for inhibiting tumor growth in a subject which may comprise administering to the subject the pharmaceutical composition of the disclosure and one or more additional antibodies, such as an anti-OX40 antibody, an anti-TIM-3 antibody, an anti-CD137 antibody, an anti-GITR antibody, an anti-LAG-3 antibody, an anti-PD-L1 antibody, and anti-PD-1 antibody. In certain embodiments, the subject is human. The TROP2 pathway blockade can also be further combined with standard cancer treatments. For example, TROP2 pathway blockade can be combined with LAG-3 and/or PD-1 blockade and also chemotherapeutic regimes. For example, a chemotherapeutic agent can be administered with the anti-TROP2 antibodies, which may be a cytotoxic agent. For example, epitubicin, oxaliplatin, and 5-FU are administered to patients receiving anti-TROP2 therapy. Optionally, the combination of anti-TROP2 and one or more additional antibodies (e.g., anti-LAG-3 and/or anti-PD-1 antibodies) can be further combined with an immunogenic agent, such as cancerous cells, purified tumor antigens (including recombinant proteins, peptides, and carbohydrate molecules), and cells transfected with genes encoding immune stimulating cytokines (He et al., (2004) *J.*

*Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF. Other therapies that may be combined with anti-TROP2 antibody includes, but not limited to, interleukin-2 (IL-2) administration, radiation, surgery, or hormone deprivation.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The disclosure further provides a method for imaging of TROP2-positive tissues, e.g., cancer tissues, in a subject in need thereof, comprising administering the subject with a radioactively labeled anti-TROP2 antibody or antigen-binding portion thereof, the immunoconjugate, or the bispecific molecule of the disclosure. The method may be used to trace/detect the distribution of a tumor or cancer with high TROP2 expression, including, but not limited to, esophageal squamous cell carcinoma, colorectal cancer, pancreatic cancer, colon cancer, papillary thyroid cancer, breast cancer, and bladder cancer. In certain embodiments, the subject is human.

Although the present invention and its advantages have been described in detail, it should be understood that various changes, substitutions and alterations can be made herein without departing from the spirit and scope of the invention as defined in the appended claims.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Generation of Single Domain Antibodies Against TROP2

Library Construction and Screening

Healthy adult camels were immunized according to the method as described in E Harlow, D. Lane, Antibody: A Laboratory Manual, Cold Spring Harbor Laboratory Press, Cold Spring Harbor, N.Y., 1998. In house made recombinant human TROP2 protein with human IgG1 Fc at the C-terminus (amino acid sequence set forth in SEQ ID NO: 15) was used as the immunogen. Immunizing dosages contained 1.0 mg human TROP2-Fc protein/camel/injection for primary immunization and 0.5 mg human TROP2-Fc protein/camel/injection for boost immunizations. To increase immune response, the complete Freud's adjuvant and incomplete Freud's adjuvant (Sigma, St. Louis, Mo., USA) were used respectively for primary and boost immunizations. After 5 immunizations, lymphocytes were isolated from 100 ml camel peripheral blood, and total RNAs were extracted by FastPure Cell/Tissue Total RNA Isolation Kit (Vazyme, Cat #RC101). Extracted RNAs were reverse transcribed into cDNAs using Hiscript III 1st Strand cDNA Synthesis kit (+gDNA wiper) (Vazyme, Cat #R312-01) according to the manual. Nucleic acid fragments encoding $V_H$Hs were amplified by nested PCRs.

Target $V_H$H nucleic acid fragments were cloned into phage display vector pMECS using endonuclease Pst and NotI (from NEB). The products were then electro-transformed into *E. coli* competent cell TG1 (from Lucigen Corporation), and phage display library for single domain antibodies against TROP2 was constructed and verified. By plating serial dilutions, library capability was determined as about $2.0\times10^8$. To determine the insertion ratio of the library, 95 clones were randomly selected for colony PCR. The results revealed an insertion ratio of more than 89.5%.

Panning for Single Domain Antibodies Against TROP2

The anti-TROP2 antibodies' cross-reactions to human TROP2 protein were measured in a phage ELISA using human TROP2-his protein (in house made with SEQ ID NO: 16). Phages that specifically bound to TROP2 were dissociated with glycine (pH=2.2, 100 mM), and used to infect *E. coli* TG1 in log phase, producing phages which were then purified for next round screening. The same screening was repeated for 2 rounds.

Selection of Individual Positive Clones by Phage Enzyme-Linked Immunoassay (ELISA)

TROP2 binding positive phages as obtained after 2 rounds of panning were used to infect blank *E. coli* which was then plated. A total of 940 single colonies were picked and inoculated in 2YT medium supplemented with 100 μg/mL ampicillin. When the optical density (OD) of the bacterial solution reached 0.6-0.8, 1M IPTG (QIAGEN, Cat #RT108-01) was added in a ratio of 1000:1, and antibody expression was induced overnight at 30° C.

ELISA plates were coated with 100 μl 1 μg/ml human TROP2-his protein (in house made with SEQ ID NO: 16), or 1 μg/ml cynomolgus TROP2-his protein (in house made with SEQ ID NO: 19) in carbonate/bicarbonate buffer (pH 9.6) overnight at 4° C., washed once with wash buffer (PBS+0.05% v/v Tween-20, PBST) and then blocked with 200 μl/well blocking buffer (5% w/v non-fatty milk in PBST) for 2 hours at 37° C. Plates were washed 4 times, and respectively incubated with 100 μl bacterial culture supernatant, and sacituzumab (used as the benchmark, also referred to as BM or BM1 hereinafter, in house made with heavy chain and light chain amino acid sequences set forth in SEQ ID NOs: 17 and 18) in 5% w/v non-fatty milk in PBST at 200 ng/ml, for 40 minutes at 37° C. The plates were washed 4 times, and incubated with THE™ HA Tag Antibody [HRP], mAb, Mouse Antibody (1:5000 dilution in PBST, GenScript, Cat #A01296, 100 μl/well, for plates with bacterial culture supernatans of the disclosure) or Peroxidase AffiniPure $F(ab')_2$ Fragment Goat Anti-Human IgG, Fcγ fragment specific (Jackson Immunoresearch, Cat #109-036-098, for plates with the benchmark), for 40 minutes at 37° C. After a final wash, plates were incubated with 100 μl/well ELISA substrate TMB (Innoreagents, Cat #TMB-S-002) at room temperature. The reaction was stopped in 3-10 minutes with 50 μl/well 1M $H_2SO_4$, and the absorbance of each well was read on a microplate reader using dual wavelength mode with 450 nm for TMB and 630 nm as the reference wavelength. When the OD of a sample well was 2 times higher than the OD of the blank well, the sample can be determined as positive. The results of exemplary supernatants were shown in Table 2.

TABLE 2

Binding Activities of Clones against TROP2

| Clone ID# | Indirect ELISA OD (450-630) | |
|---|---|---|
| | Human TROP2-his | CynomolgusTROP2-his |
| 01-9F | 0.97 | 0.59 |
| 01-5A | 1.03 | 0.56 |
| sacituzumab | 3.94 | 3.96 |
| Blank | 0.01 | 0.01 |

Bacteria in the positive wells were transferred to and cultured in LB liquid medium supplemented with 100 μg/ml Ampicillin for plasmid extraction and subsequent sequencing.

The amino acid sequences of the antibodies produced by each clone were analyzed according to the sequence alignment software Vector NTI, and two single domain antibodies were finally obtained whose CDR and $V_H$H sequences were listed in Table 1.

Example 2 Preliminary Evaluation of Single Domain Antibodies Against TROP2

The vectors each containing a nucleotide encoding the $V_H$H were transiently transfected into 100 ml 293F suspension cell cultures, with 3 μg/ml PEI. Cell supernatants containing single domain antibodies were harvested after six days in shaking flasks, spun down to pellet cells, and then single domain antibodies were purified from cell supernatant by Protein A sepharose columns (from bestchrom (Shanghai) Biosciences, Cat #AA0273). Briefly, the columns were washed using PBS buffer in 5 to 10 column volumes. Cell supernatants were passed through the columns, and then the columns were washed using PBS buffer until the absorbance for protein reached the baseline. The columns were eluted with elution buffer (0.1 M Glycine-HCl, pH 2.7), and immediately collected into 1.5 ml tubes with neutralizing buffer (1 M Tris-HCl, pH 9.0). Fractions containing single domain antibodies were pooled and dialyzed in PBS overnight at 4° C.

The purified single domain antibodies were subject to the indirect ELISA, epitope binning, BIAcore affinity test and cell-based internalization assay, following the protocols described below.

The single domain antibodies of the disclosure were tested in the indirect ELISA for their cross-reaction with cynomolgus TROP2 protein. Briefly, 96-well micro plates were coated with 100 μl 2 μg/ml human TROP2-his protein (prepared in-house with SEQ ID NO: 16) in carbonate/bicarbonate buffer (pH 9.6) overnight at 4° C. ELISA plates were washed once with wash buffer (PBS+0.05% v/v Tween-20, PBST) and then blocked with 200 μl/well blocking buffer (5% w/v non-fatty milk in PBST) for 2 hours at 37° C. Plates were washed 4 times and incubated with 100 μl/well serially diluted anti-TROP2 antibodies of the disclosure or controls (starting at 66.7 nM, 5-fold serial dilution in 2.5% w/v non-fatty milk in PBST) for 40 minutes at 37° C. ELISA plates were washed 4 times again and incubated with Peroxidase AffiniPure $F(ab')_2$ Fragment Goat Anti-Human IgG, Fey fragment specific (Jackson Immuno Research, Cat #109-036-098, 1:5000 dilution in PBST buffer, 100 μl/well) for 40 minutes at 37° C. After a final wash, plates were incubated with 100 μl/well TMB (Innoreagents) at room temperature. The reaction was stopped 3-10 minutes later at room temperature with 50 μl/well 1M $H_2SO_4$, and the absorbance of each well was read on a microplate reader using dual wavelength mode with 450 nm for TMB and 630 nm as the reference wavelength. The OD (450-630) values were plotted against antibody concentration. Data was analyzed using Graphpad Prism software and $EC_{50}$ values were reported. The results were shown in FIG. 1.

The purified anti-TROP2 mouse monoclonal antibodies (mAbs) were characterized for binding affinity and binding kinetics by Biacore T200 system (GE healthcare, Pittsburgh, PA, USA). Briefly, goat anti-human IgG (GE healthcare, Cat #BR100839, Human Antibody Capture Kit) was covalently linked to a CM5 chip (carboxy methyl dextran coated chip from GE healthcare #BR100530) via primary amines, using a standard amine coupling kit (GE healthcare, Pittsburgh, PA, USA) provided by Biacore. Un-reacted moieties on the chip (biosensor) surface were blocked with ethanolamine. The anti-TROP2 antibodies of the disclosure and the benchmark at the concentration of 2 μg/ml were respectively flowed onto the chip at a flow rate of 10 μL/min. Then, serially diluted human TROP2-his protein (prepared in-house with SEQ ID NO: 16), or cynomolgus TROP2-his protein (prepared in-house with SEQ ID NO: 19), 2-fold dilution in $HBS-EP^+$ buffer (provided by Biacore) starting at 160 nM, were flowed onto the chip at a flow rate of 30 μL/min. The antigen-antibody association kinetics was followed for 2 minutes and the dissociation kinetics was followed for 10 minutes. The association and dissociation curves were fit to a 1:1 Langmuir binding model using BIAcore evaluation software. The results were shown in Table 3.

The anti-TROP2 antibodies were tested for their epitope binding in a competitive ELISA assay. Briefly, 100 μl of the benchmark at 1 μg/mL in PBS was coated on 96-well micro plates for 2 hours at 37° C. ELISA plates were washed once with wash buffer (PBS+0.05% v/v Tween-20, PBST) and then blocked with 200 μl blocking buffer (5% w/v non-fatty milk in PBST) for 2 hours at 37° C. While blocking, the anti-TROP2 antibodies of the disclosure or controls were diluted with biotin labeled human TROP2-his protein (SEQ ID NO: 16, 34 ng/mL in 2.5% w/v non-fatty milk in PBST), starting at 80 nM with a 5-fold serial dilution, and incubated at room temperature for 40 minutes. After plate washing 4 times, the antibody/TROP2-his protein mixtures were added to benchmark coated plates, 100 μl per well. After incubation at 37° C. for 40 minutes, plates were washed 4 times again using wash buffer. Then the plates were added and incubated with 100 μl Peroxidase Streptavidin (1:10000 dilution in PBST buffer, Jackson Immunoresearch, Cat #016-030-084) for 40 minutes at 37° C. Plates were washed again using wash buffer. Finally, TMB was added and the reaction was stopped using 1M $H_2SO_4$. The absorbance of each well was read on a microplate reader using dual wavelength mode with 450 nm for TMB and 630 nm as the reference wavelength, and the OD (450-630) values were plotted against antibody concentration. Data was analyzed using Graphpad Prism software and $IC_{50}$ values were reported. The results were shown in FIG. 2.

For the cell-based internalization assay, the anti-TROP2 antibodies were evaluated precisely for their internalization efficiencies using Biosion in-house prepared 293F-TROP2 cells (clone ID #3A8) stably expressing full length human TROP2 (uniprot #P09758, SEQ ID NO.: 20) on cell membrane. The 293F-TROP2 cells were prepared by transfecting 293F cells (Thermofisher Inc., Cat #11625019) with a pCMV-T-P plasmid inserted with TROP2 coding sequence between EcoRI and XbaI sites, following the instruction of lipofectamine 3000 transfection reagent (Thermo Fisher).

Firstly, $5\times10^3$ 293F-TROP2 cells in 100 μL FreeStyle293 medium (Gibco, Cat #12338-018) supplemented with 10% v/v FBS (Gibco, Cat #10099-141) were plated in 96 well-flat bottom plates (Thermo Fisher Scientific Inc., Cat #167008). On the next day of cell seeding, the anti-TROP2 antibodies of the disclosure or controls, 1.6 μg/mL in FreeStyle293 medium with 10% v/v FBS, were mixed with DTTP1170, a recombinant protein synthesized using the amino acid sequence set forth in SEQ ID NO: 22, 1.6 μg/mL in FreeStyle293 medium with 10% v/v FBS, at 1:1 volume ratio, and incubated at room temperature for 30 minutes, which were then serially diluted in the cell culture medium, 3-fold serial dilution, starting from 0.8 μg/mL. Then, 100 μl of the serially diluted antibody/DTTP1170 mixtures were added to the cell plates, and incubated in a $CO_2$ incubator at 37° C. for 72 hours. The plates were added with Cell Titer Glo reagent (Vazyme Biotech Co., Ltd, Cat #DD1101-02) and incubated for 3-5 minutes at room temperature. The cell culture plates were then analyzed by Tecan infinite 200Pro plate-reader. Data were analyzed using Graphpad prism software and $IC_{50}$ values were reported as the antibody concentrations that achieved 50% of maximal inhibition on cell viability. The results were shown in FIG. 3. When the mAb-DTTP conjugates were internalized by the target cells, target cell viability markedly decreased. If the conjugates were not internalized, then the free DTTP1170 in the medium had no or little cell killing activity.

TABLE 3

Binding affinities of single domain antibodies

| Clone ID# | Kinetics on Biacore: Human TROP2-his $K_a$ ($M^{-1}s^{-1}$) | $K_d$ ($s^{-1}$) | $K_D$ (M) | Cyno TROP2-his $K_a$ ($M^{-1}s^{-1}$) | $K_d$ ($s^{-1}$) | $K_D$ (M) |
|---|---|---|---|---|---|---|
| 01-9F | 3.09E+05 | 8.11E−06 | 2.62E−11 | 2.87E+05 | 1.61E−04 | 5.58E−10 |
| 01-5A | 2.80E+05 | 2.73E−05 | 9.75E−11 | 2.66E+05 | 1.72E−04 | 6.47E−10 |
| BM | 2.84E+05 | 1.16E−04 | 4.09E−10 | 2.57E+05 | 2.24E−04 | 8.74E−10 |

It can be seen from Table 3 that the single domain antibodies of the disclosure specifically bound to human TROP2 with higher binding affinities than the benchmark, and specifically bound to cynomolgus monkey TROP2 with comparable affinities to the benchmark.

FIG. 1 showed that the single domain antibodies of the disclosure specifically bound to human TROP2 protein with similar Bmaxs but a bit lower EC50s as compared with the benchmark.

Figure 2:
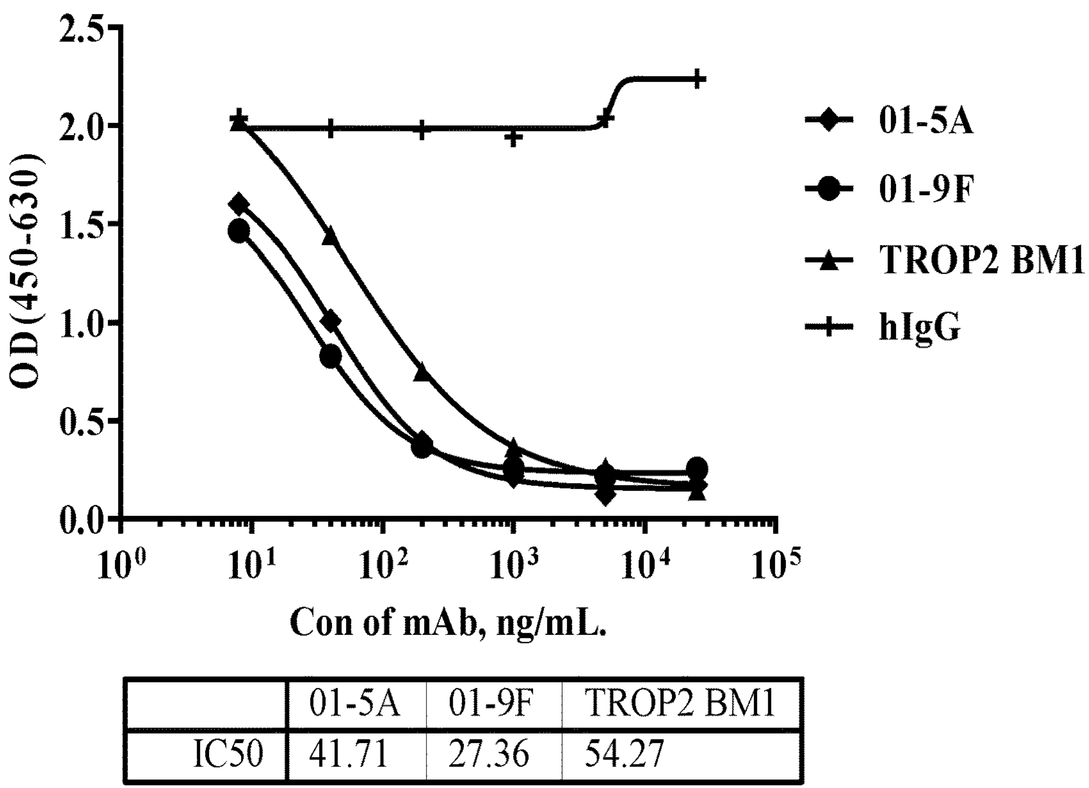
FIG. 2 shows the abilities of single domain antibodies 01-9F and 01-5A to block benchmark-human TROP2 binding in a competitive ELISA test.

As shown in FIG. 2, the single domain antibodies of the disclosure were able to block human TROP2-benchmark binding, suggesting they bound to the same or similar epitope as the benchmark did.

Figure 3:
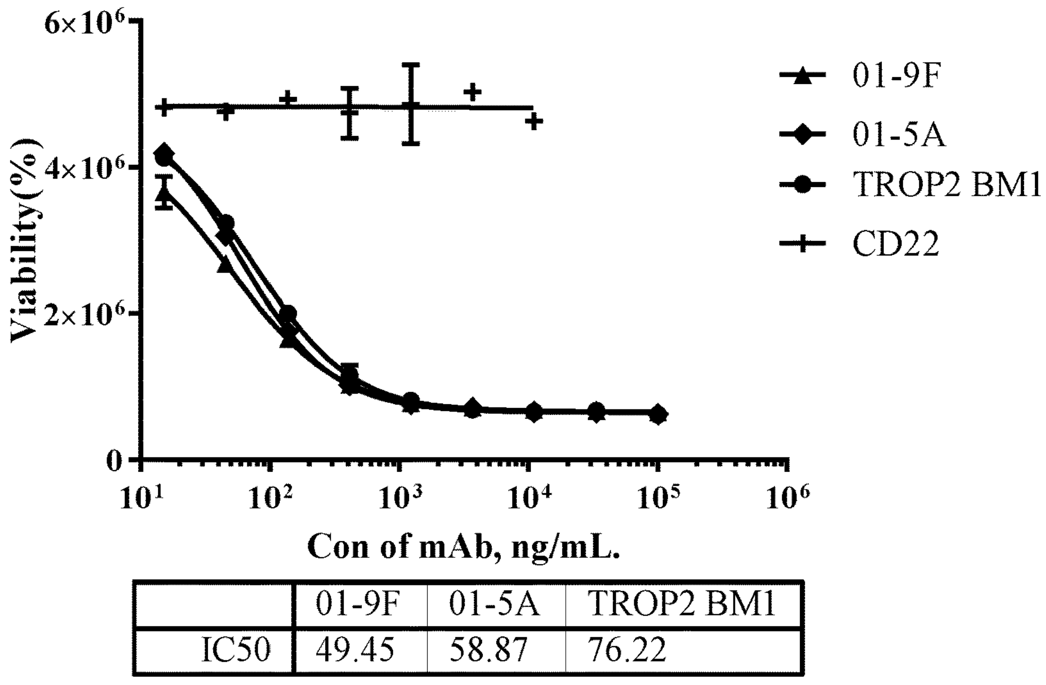
FIG. 3 shows the internalization-mediated cellular toxicities of DT3C conjugates of single domain antibodies 01-9F and 01-5A on 293F-TROP2 cells.

Further, as shown in FIG. 3, the DT3C conjugates of single domain antibodies of the disclosure more efficiently caused target cell death than the benchmark-DT3C conjugate.

Example 3 Genetic Engineering of Single Domain Antibody 01-9F

The 01-9F single domain antibody ($V_HH$) was cloned in frame to human IgG1 Fc region (prepared in-house with SEQ ID NO: 14), wherein the C terminus of the $V_HH$ was linked to the N terminus of the Fc region.

The vectors each containing a nucleotide encoding the $V_HH$ linked to human IgG1-Fc region were transiently incubated with 100 ml 293F suspension cell cultures, with 3 μg/ml PEI. Cell supernatants containing the heavy chain only antibodies ($V_HH$-Fc) were harvested after six days in shaking flasks, spun down to pellet cells, and then the obtained heavy chain only antibody (also referred to as 01-9F-Fc herein) was purified from cell supernatants as described above.

To avoid or reduce post translational modifications such as isomerization of certain amino acid residues in e.g., the CDR regions that might adversely affect antibody's production, stability, safety and/or efficacy, the single domain antibody 01-9F was further modified in the CDR2 or CDR3 region, and a total of 11 modified variants, namely 01-9F-CDR-V1 to 01-9F-CDR-V11, were obtained, whose CDR and $V_HH$ sequence ID numbers were listed in Table 1.

The vectors each containing a nucleotide encoding the $V_HH$ of one of 01-9F-CDR-V1 to 01-9F-CDR-V11 linked to human IgG1 heavy-chain constant region (SEQ ID NO: 14), were transiently transfected into 100 ml 293F suspension cell cultures, with 3 μg/ml PEI.

Example 4 Characterization of 01-9F-Fc Variants

Cell supernatants containing the heavy chain only antibodies (01-9F-Fc variants), i.e., 01-9F-CDR-V1-Fc to 01-9F-CDR-V11-Fc, were harvested after six days in shaking flasks, spun down to pellet cells, and tested in BIAcore affinity test and cell-based internalization assay, following the protocols in the foregoing Examples with modifications described below.

For the BIAcore test, cell supernatants containing the 01-9F-Fc variants were respectively flowed onto the chip instead of the purified anti-TROP2 antibodies, at a flow rate of 10 μL/min, and 40 nM human TROP2-his proteins (prepared in-house with SEQ ID NO: 16) in HBS-EP$^+$ buffer (provided by Biacore), instead of serially diluted human TROP2-his proteins, were flowed onto the chip at a flow rate of 30 μL/min. The $K_D$, $K_a$ and $K_d$ values were determined and summarized in Table 4 below.

TABLE 4

Binding affinities of 01-9F-Fc variants

| Clone ID# | Kinetics on Biacore Human TROP2-his $K_a$ ($M^{-1}s^{-1}$) | $K_d$ ($s^{-1}$) | $K_D$ (M) |
|---|---|---|---|
| 01-9F-CDR-V1-Fc | 3.25E+05 | 1.03E−04 | 3.17E−10 |
| 01-9F-CDR-V2-Fc | 3.68E+05 | 9.23E−05 | 2.51E−10 |

TABLE 4-continued

Binding affinities of 01-9F-Fc variants

| Clone ID# | Kinetics on Biacore Human TROP2-his $K_a$ ($M^{-1}s^{-1}$) | $K_d$ ($s^{-1}$) | $K_D$ (M) |
|---|---|---|---|
| 01-9F-CDR-V3-Fc | 2.61E+05 | 1.17E−04 | 4.50E−10 |
| 01-9F-CDR-V4-Fc | 3.20E+05 | 7.01E−05 | 2.19E−10 |
| 01-9F-CDR-V5-Fc | 3.68E+05 | 3.99E−05 | 1.08E−10 |
| 01-9F-CDR-V6-Fc | 3.36E+05 | 6.62E−05 | 1.97E−10 |
| 01-9F-CDR-V7-Fc | 4.39E+05 | 1.14E−04 | 2.61E−10 |
| 01-9F-CDR-V8-Fc | 3.23E+05 | 6.92E−05 | 2.15E−10 |
| 01-9F-CDR-V9-Fc | 4.13E+05 | 1.05E−04 | 2.54E−10 |
| 01-9F-CDR-V10-Fc | 4.50E+05 | 1.17E−04 | 2.59E−10 |
| 01-9F-CDR-V11-Fc | 4.75E+05 | 8.17E−05 | 1.72E−10 |
| 01-9F-Fc | 4.56E+05 | 1.54E−04 | 3.38E−10 |
| 01-9F | 5.02E+05 | 1.01E−04 | 2.02E−10 |

In the cell-based internalization assay, DT3C was used to conjugate the heavy chain only antibodies, and an in house made anti-CD22 antibody was used as a negative control. Briefly, $1.5\times10^3$ 293F-TROP2 cells in 100 μL FreeStyle293 medium (Gibco, Cat #12338-018) supplemented with 10% v/v FBS (Gibco, Cat #10099-141) were plated in 96 well-flat bottom plates (Thermo Fisher Scientific Inc., Cat #167008). The 01-9F-Fc variants or controls, 40 nM in FreeStyle293 medium with 10% v/v FBS, were mixed with DT3C proteins, 40 nM in FreeStyle293 medium with 10% v/v FBS, at 1:1 volume ratio, and incubated at room temperature for 30 minutes, which were then serially diluted in the cell culture medium, 3-fold serial dilution, starting from 20 nM. The results were shown in FIG. 4.

It can be seen from Table 4 that the 01-9F-CDR-Fc variants of the disclosure specifically bound to human TROP2 with comparable binding affinities compared to 01-9F and 01-9F-Fc.

Figure 4:
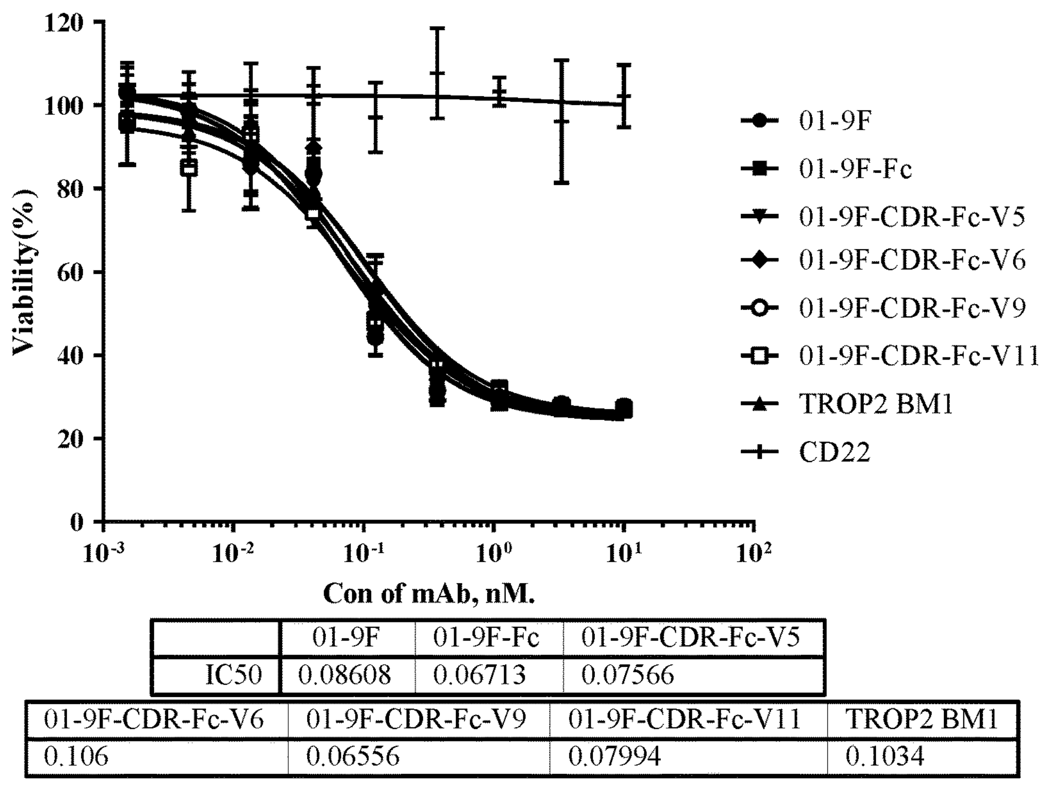
FIG. 4 shows the internalization-mediated cellular toxicities of DT3C conjugates of heavy chain only antibodies 01-9F-CDR-V5-Fc, 01-9F-CDR-V6-Fc, 01-9F-CDR-V9-Fc and 01-9F-CDR-V11-Fc on 293F-TROP2 cells.

According to FIG. 4, the DT3C conjugates of 01-9F-Fc variants, including 01-9F-CDR-V5-Fc, 01-9F-CDR-V9-Fc and 01-9F-CDR-V11-Fc, more efficiently caused target cell death compared to benchmark-DT3C conjugate.

Example 5 Humanization of 01-9F-CDR-V11

The variant 01-9F-CDR-V11-Fc was purified and humanized, and a total of 24 exemplary humanized antibodies, namely 01-9F-CDR-V11-V1-Fc to 01-9F-CDR-V11-V24-Fc were obtained whose $V_H$H sequence ID numbers were in Table 1.

The vectors each containing a nucleotide encoding the $V_H$H of one of 01-9F-CDR-V11-V1 to 01-9F-CDR-V11-V24 linked to human IgG1 heavy-chain constant region (SEQ ID NO: 14), were transiently transfected into 100 ml 293F suspension cell cultures, with 3 μg/ml PEI.

Example 6 Characterization of Exemplary Humanized 01-9F-CDR-V11 Antibodies

Cell supernatants containing humanized 01-9F-CDR-V11 antibodies were harvested after six days in shaking flasks, spun down to pellet cells, and tested for binding affinity to human TROP2 by BiAcore T200 system (GE healthcare, Pittsburgh, PA, USA) following the protocol in the foregoing Examples with modifications described below.

TABLE 5

Binding affinities of humanized 01-9F-CDR-V11 antibodies

| Clone ID# | Kinetics on Biacore Human TROP2-his $K_a$ ($M^{-1}s^{-1}$) | $K_d$ ($s^{-1}$) | $K_D$ (M) |
|---|---|---|---|
| 01-9F-CDR-V11-V1-Fc | 1.08E+06 | 1.86E−04 | 1.73E−10 |
| 01-9F-CDR-V11-V2-Fc | 9.98E+05 | 0.001605 | 1.61E−09 |
| 01-9F-CDR-V11-V3-Fc | 8.87E+05 | 0.002195 | 2.47E−09 |
| 01-9F-CDR-V11-V4-Fc | 1.74E+06 | 0.001492 | 8.60E−10 |
| 01-9F-CDR-V11-V6-Fc | 1.88E+06 | 0.001207 | 6.43E−10 |
| 01-9F-CDR-V11-V7-Fc | 2.03E+06 | 0.001184 | 5.83E−10 |
| 01-9F-CDR-V11-V8-Fc | 1.67E+06 | 0.002411 | 1.44E−09 |
| 01-9F-CDR-V11-V9-Fc | 2.93E+06 | 5.39E−04 | 1.84E−10 |
| 01-9F-CDR-V11-V11-Fc | 1.47E+06 | 2.94E−04 | 2.00E−10 |
| 01-9F-CDR-V11-V12-Fc | 1.40E+06 | 0.001613 | 1.16E−09 |
| 01-9F-CDR-V11-V13-Fc | 1.30E+06 | 0.002572 | 1.98E−09 |
| 01-9F-CDR-V11-V14-Fc | 1.42E+06 | 0.001709 | 1.21E−09 |
| 01-9F-CDR-V11-V16-Fc | 1.47E+06 | 0.001176 | 8.02E−10 |
| 01-9F-CDR-V11-V17-Fc | 1.39E+06 | 0.001709 | 1.23E−09 |
| 01-9F-CDR-V11-V18-Fc | 1.23E+06 | 0.002899 | 2.37E−09 |
| 01-9F-CDR-V11-V19-Fc | 1.39E+06 | 0.001916 | 1.38E−09 |
| 01-9F-CDR-V11-V21-Fc | 1.41E+06 | 0.001503 | 1.07E−09 |
| 01-9F-CDR-V11-V22-Fc | 1.11E+06 | 0.002367 | 2.14E−09 |
| 01-9F-CDR-V11-Fc | 1.48E+06 | 2.23E−04 | 1.51E−10 |
| 01-9F | 1.19E+06 | 2.24E−04 | 1.88E−10 |

For the BIAcore test, cell supernatants containing humanized 01-9F-CDR-V11 antibodies were respectively flowed onto the chip at a flow rate of 10 μL/min, and 40 nM human TROP2-his protein (prepared in-house with SEQ ID NO: 16) in HBS-EP$^+$ buffer (provided by Biacore) were flowed onto the chip at a flow rate of 30 μL/min. The $K_D$, $K_a$ and $K_d$ values were determined and summarized in Table 5 above.

It can be seen from Table 5 that the humanized 01-9F-CDR-V11 antibodies had high human TROP2 binding affinities, with 01-9F-CDR-V11-V1, 01-9F-CDR-V11-V9 and 01-9F-CDR-V11-V11 showing the highest binding affinities.

Example 7 Further Characterization of Exemplary Humanized 01-9F-CDR-V11 Antibodies The humanized antibodies 01-9F-CDR-V11-V1-Fc, 01-9F-CDR-V11-V9-Fc and 01-9F-CDR-V11-V11-Fc were purified as described above and tested in cell-based internalization assay, following the protocols in the foregoing Examples with modifications described below.

In the cell-based internalization assay, DT3C was used to conjugate these antibodies, and an in house made anti-CD22 antibody was used as a negative control. Briefly, $1.5\times10^3$ 293F-TROP2 cells (clone ID #3A8) in 100 μL FreeStyle293 medium (Gibco, Cat #12338-018) supplemented with 10% v/v FBS (Gibco, Cat #10099-141) were plated in 96 well-flat bottom plates (Thermo Fisher Scientific Inc., Cat #167008). The humanized antibodies or controls, 40 nM in FreeStyle293 medium with 10% v/v FBS, were mixed with DT3C protein, 40 nM in FreeStyle293 medium with 10% v/v FBS, at 1:1 volume ratio, and incubated at room temperature for 30 minutes, which were then serially diluted in the cell culture medium, 3-fold serial dilution, starting from 20 nM. The results were shown in FIG. 5.

Figure 5:
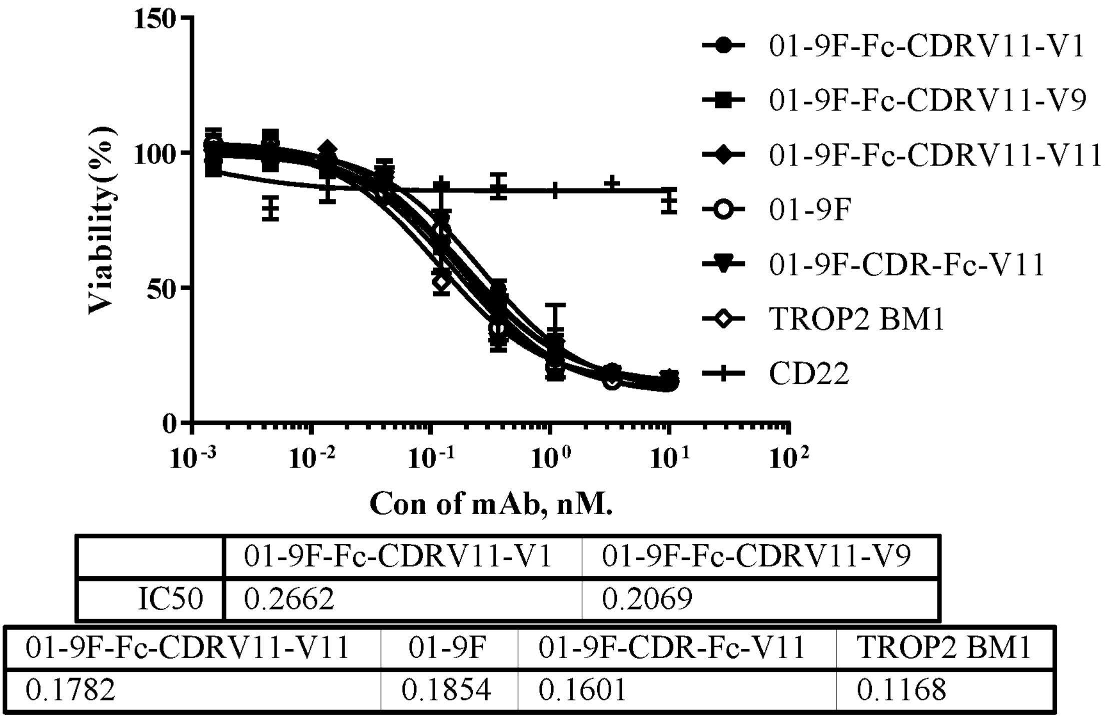
FIG. 5 shows the internalization-mediated cellular toxicities of DT3C conjugates of humanized antibodies 01-9F-CDR-V11-V1-Fc, 01-9F-CDR-V11-V9-Fc and 01-9F-CDR-V11-V11-Fc on 293F-TROP2 cells.

According to FIG. 5, the DT3C conjugates of humanized 01-9F-CDR-V11 antibodies, including 01-9F-CDR-V11-V1-Fc, 01-9F-CDR-V11-V9-Fc and 01-9F-CDR-V11-V11-Fc, caused target cell death at similar rates to the benchmark-DT3C conjugate.

The humanized antibody 01-9F-CDR-V11-V11-Fc was further tested in Biacore, Capture ELISA, Indirect ELISA, Cell-based binding FACS, Competitive ELISA and Protein thermal shift assay, following the protocols described below and protocols described in the foregoing Examples with or without modifications.

The BIAcore test results were summarized in Table 6 below.

Figure 6:
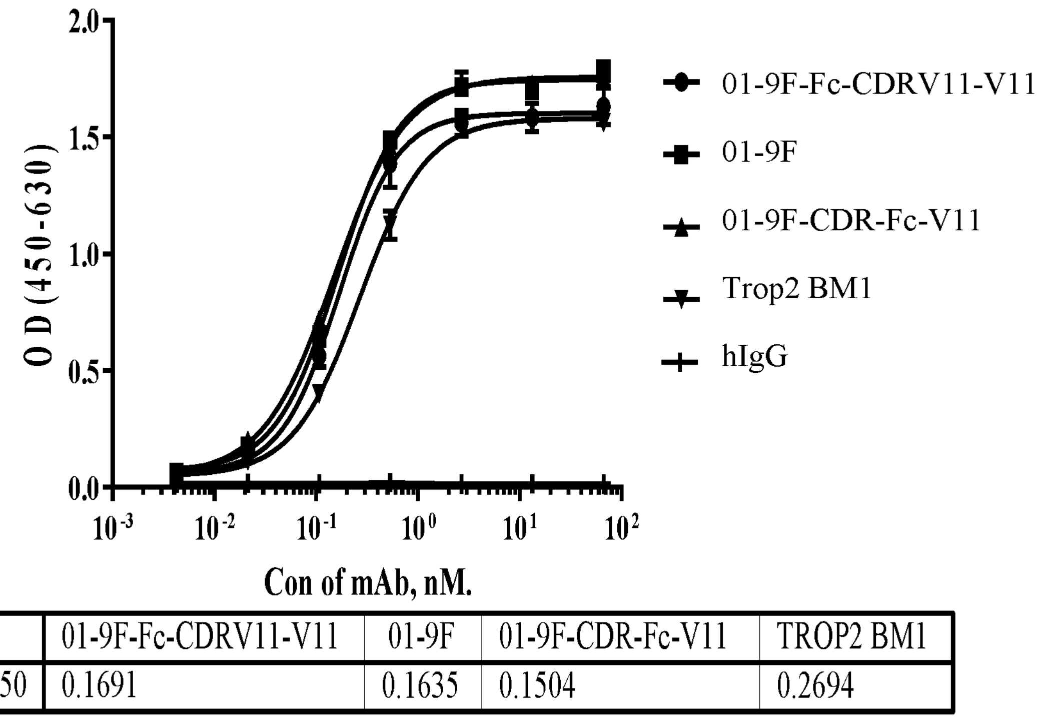
FIG. 6 shows the binding capability of humanized antibody 01-9F-CDR-V11-V11-Fc to human TROP2 in a capture ELISA.

For the capture ELISA, 96-well plates were coated with 100 μl 2 μg/ml AffiniPure F(ab')$_2$ Fragment GoatAnti-Human IgG, Fey fragment specific (Jackson Immuno Research, Cat #109-006-008) in PBS overnight at 4° C. Plates were washed once with wash buffer (PBS+0.05% v/v Tween-20, PBST) and then blocked with 200 μl/well blocking buffer (5% w/v non-fatty milk in PBST) for 2 hours at 37° C. Plates were washed 4 times and respectively incubated with 100 μl serially diluted anti-TROP2 antibodies of the disclosure, the benchmark or negative control hIgG (human immunoglobulin (pH4) for intravenous injection, Hualan Biological Engineering Inc.) (5-fold dilution in 2.5% w/v non-fatty milk in PBST, starting at 66.7 nM) for 40 minutes at 37° C., and then washed 4 times again. Plates containing captured anti-TROP2 antibodies were incubated with biotin-labeled human TROP2-his protein (prepared in house, SEQ ID NO: 16, 56.7 ng/mL in 2.5% w/v non-fatty milk in PBST, 100 μl/well) for 40 minutes at 37° C., washed 4 times, and incubated with streptavidin conjugated HRP (1:10000 dilution in PBST, Jackson Immuno Research, Cat #016-030-084, 100 μl/well) for 40 minutes at 37° C. After a final wash, plates were incubated with 100 μl/well ELISA substrate TMB (Innoreagents, Cat #TMB-S-002) at room temperature. The reaction was stopped in 3-10 minutes at room temperature with 50 μl/well 1M $H_2SO_4$, and the absorbance of each well was read on a microplate reader using dual wavelength mode with 450 nm for TMB and 630 nm as the reference wavelength. The OD (450-630) values were plotted against antibody concentration. Data was analyzed using Graphpad Prism software and $EC_{50}$ values were reported. The results were shown in FIG. 6.

Figure 7:
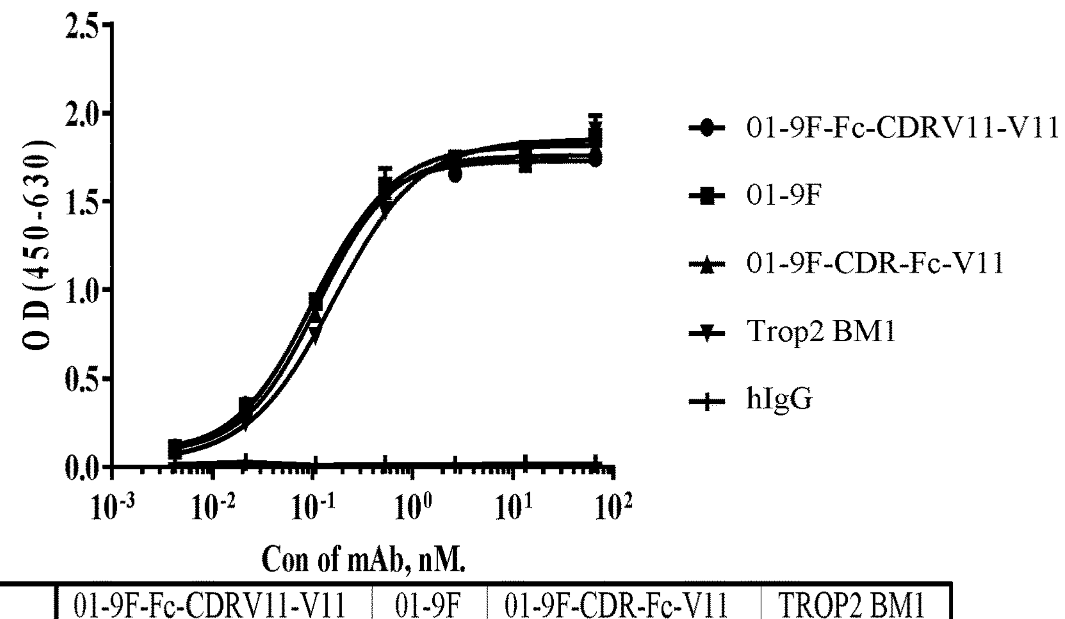
FIG. 7 shows the binding capability of humanized antibody 01-9F-CDR-V11-V11-Fc to human TROP2 in an indirect ELISA.
Figure 8:
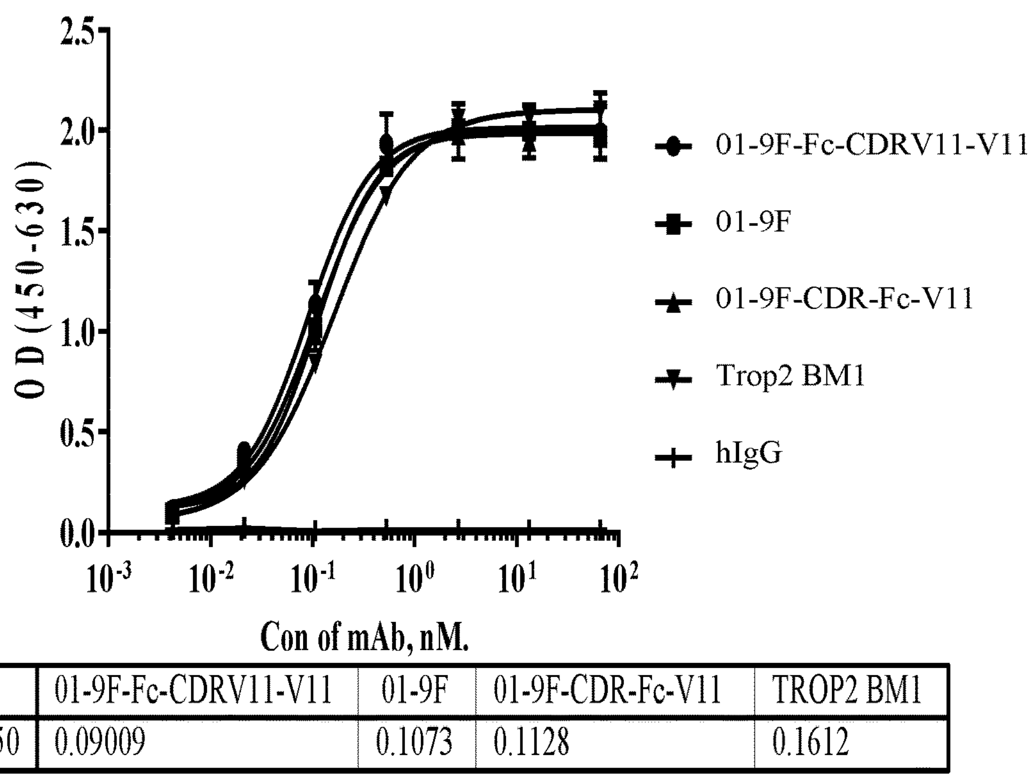
FIG. 8 shows the binding capability of humanized antibody 01-9F-CDR-V11-V11-Fc to cynomolgus TROP2 in an indirect ELISA.

For the indirect ELISA, AffiniPure Goat Anti-Human IgG, Fey fragment specific (Jackson Immunoresearch, Cat #109-005-098) was used, 100 μl/well. The results were shown in FIGS. 7 and 8.

Figure 9:
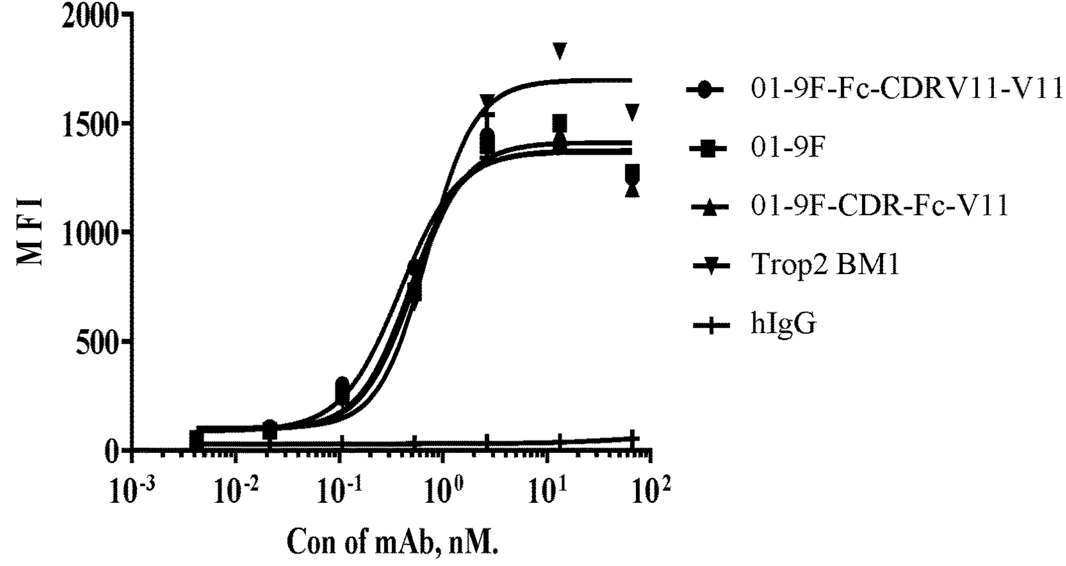
FIG. 9 shows the binding capability of humanized antibody 01-9F-CDR-V11-V11-Fc to 293F-TROP2 cells expressing human TROP2 in a cell based binding FACS assay.

In the cell-based binding FACS, the 293F-TROP2 cells were harvested from cell culture flasks, washed twice and re-suspended in phosphate buffered saline (PBS) containing 2% v/v Fetal Bovine Serum (FACS buffer). Then, $2\times10^5$ 293F-TROP2 cells per well were incubated in 96 well-plates with 100 μl of the anti-TROP2 antibodies or controls at various concentrations (starting at 66.7 nM, 4-fold serial dilution in FACS buffer) for 40 minutes on ice. Cells were washed twice with FACS buffer, and added with 100 μL/well R-Phycoerythrin AffiniPure Goat Anti-Human IgG, Fey fragment specific (1:1000 dilution in FACS buffer, Jackson Immunoresearch, Cat #109-115-098). Following an incubation of 40 minutes at 4° C. in dark, cells were washed twice and re-suspended in FACS buffer. Fluorescence was measured using a Becton Dickinson FACS Canto II-HTS equipment, and the MFI (mean fluorescence intensity) was plotted against antibody concentration. Data was analyzed using Graphpad Prism software and $EC_{50}$ values were reported. The results were shown in FIG. 9.

Figure 10:
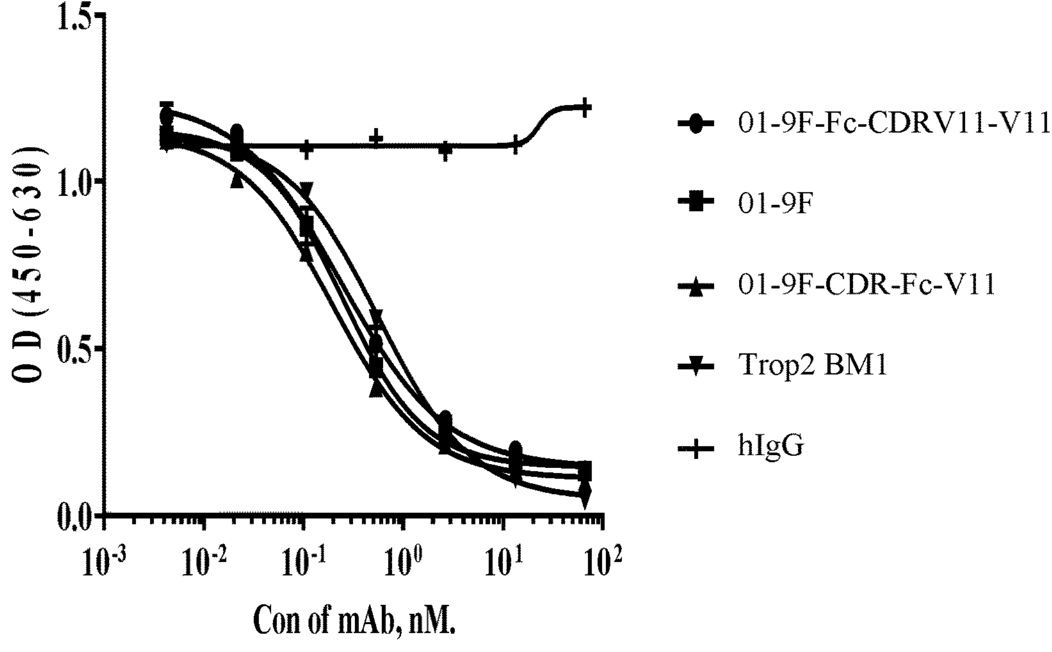
FIG. 10 shows the ability of humanized antibody 01-9F-CDR-V11-V11-Fc to block benchmark-human TROP2 binding in a competitive ELISA test.

For the epitope binning, 2 μg/mL benchmark was used, 100 μl/well. The humanized antibody 01-9F-CDR-V11-V11 or controls were diluted with biotin labeled human TROP2-his protein (SEQ ID NO: 16, 8.7 ng/mL in 2.5% w/v non-fatty milk in PBST), starting at 66.7 nM with a 5-fold serial dilution, and incubated at room temperature for 40 minutes. The results were shown in FIG. 10.

For the thermal shift assay, Protein Thermal Shift™ Dye Kit (Thermo Fisher, Cat #4461146) was used to determine Tm (melting temperature). Briefly, the GloMelt™ dye was allowed to thaw and reach room temperature. The vial containing the dye was vortexed and centrifuged. Then, 10× dye was prepared by adding 5 μL 200× dye to 95 μL PBS. 2 μL 10× dye and 10 μg humanized antibodies were added, and PBS was added to a total reaction volume of 20 μL. The tubes containing the dye and antibodies were briefly spun and placed in CFX Connect Real-Time PCR Detection System (Bio-Rad, Cat #1855201). The results were shown in FIGS. 11A-11C.

TABLE 6

Binding affinity of 01-9F-CDR-V11-V11-Fc

| | Kinetics on Biacore | | | | | |
|---|---|---|---|---|---|---|
| | Human TROP2-his | | | Cynomolgus TROP2-his | | |
| Clone ID# | $K_a$ ($M^{-1}s^{-1}$) | $K_d$ ($s^{-1}$) | $K_D$ (M) | $K_a$ ($M^{-1}s^{-1}$) | $K_d$ ($s^{-1}$) | $K_D$ (M) |
| 01-9F | 5.86E+05 | 1.70E−04 | 2.91E−10 | 5.25E+05 | 1.50E−04 | 2.85E−10 |
| 01-9F-CDR-V11-Fc | 3.89E+05 | 1.27E−04 | 3.27E−10 | 4.12E+05 | 1.24E−04 | 3.00E−10 |
| 01-9F-CDR-V11-V11-Fc | 3.94E+05 | 1.79E−04 | 4.53E−10 | 4.53E+05 | 1.80E−04 | 3.97E−10 |
| BM1 | 5.16E+05 | 2.86E−04 | 5.54E−10 | 5.22E+05 | 2.28E−04 | 4.36E−10 |

According to Table 6, 01-9F-CDR-V11-V11-Fc showed comparable binding affinity to human and cynomolgus TROP2 compared to 01-9F and 01-9F-CDR-V11-Fc, which was a bit higher than that of the benchmark. FIGS. 6 to 9 showed 01-9F-CDR-V11-V11-Fc had higher binding activity to human and monkey TROP2 than the benchmark.

As shown in FIG. 10, 01-9F-Fc-CDRV 11-V11 was capable of blocking BM1-TROP2 binding, indicating that it might bind to a similar epitope as BM1 did.

Figure 11A:
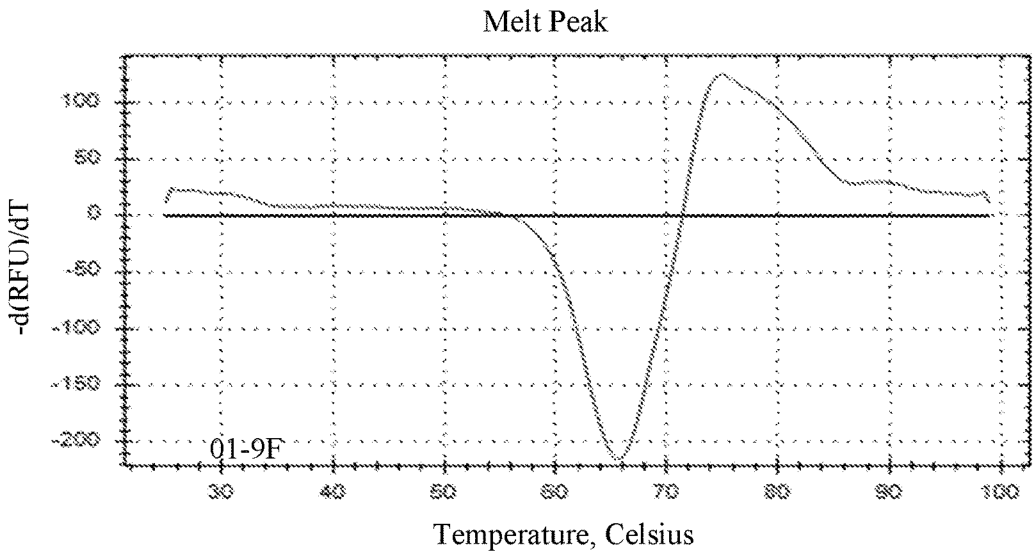
FIGS. 11A-11C show the protein thermal shift assay results of antibodies 01-9F (A), 01-9F-CDR-V11-Fc (B) and 01-9F-CDR-V11-V11-Fc (C).
Figure 11B:
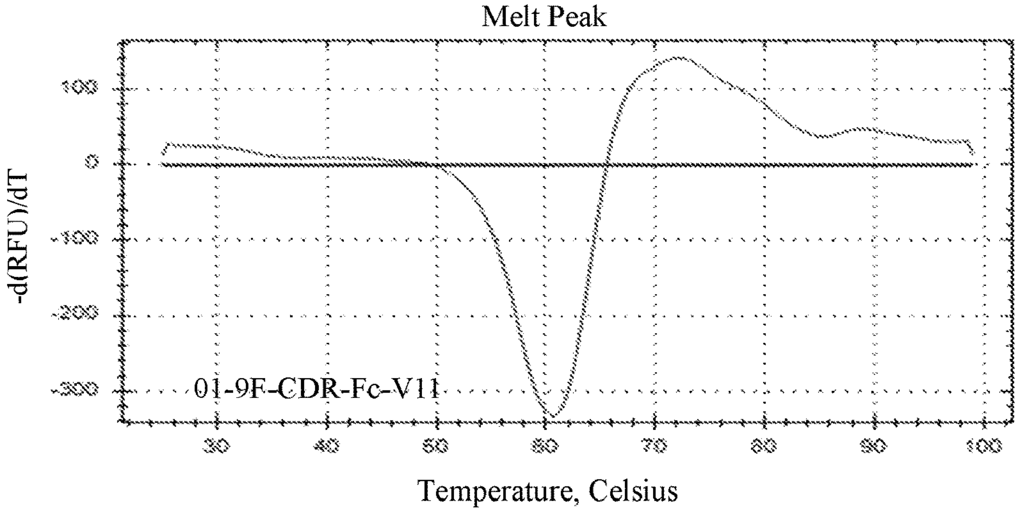
Figure 11C:
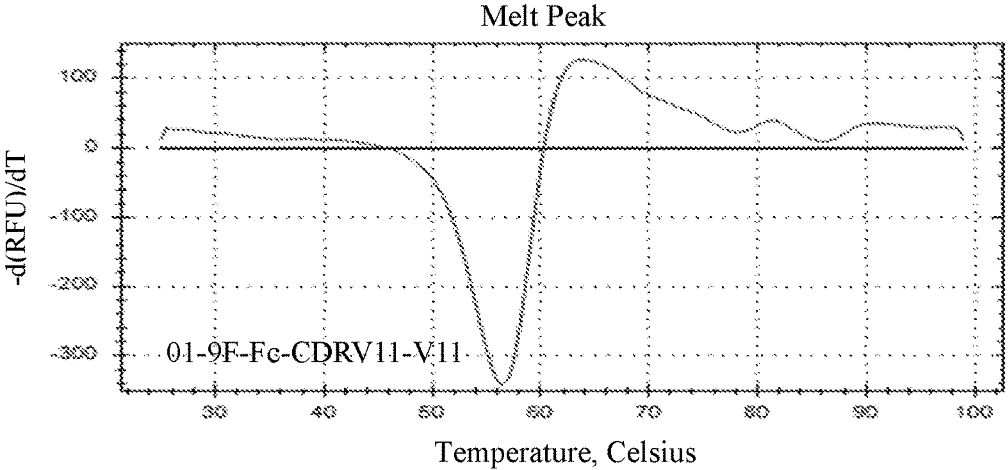

Further, as shown in FIGS. 11A-11C, with the melting temperatures, the antibodies 01-9F, 01-9F-CDR-V11-Fc and 01-9F-CDR-V11-V11-Fc were probably stable in human body.

While the disclosure has been described above in connection with one or more embodiments, it should be understood that the disclosure is not limited to those embodiments, and the description is intended to cover all alternatives, modifications, and equivalents, as may be included within the spirit and scope of the appended claims. All referenced cited herein are further incorporated by reference in their entirety.

Sequences in the present application are summarized below.

| Description/Sequence/SEQ ID NO. |
|---|
| $V_H$H CDR1 for 01-9F, 01-9F-CDR-V1 to 01-9F-CDR-V11, 01-9F-CDR-V11-V1 to 01-9F-CDR-V11-V24<br>RYCVA (SEQ ID NO: 1) |
| $V_H$H CDR2 for 01-9F, 01-9F-CDR-V1 to 01-9F-CDR-V3<br>RILSX1X2TTSYSX3X4VKG (SEQ ID NO: 2) X1 = D, X2 = G, X3 = D, X4 = S<br>RILSDGTTSYSDSVKG |
| $V_H$H CDR2 for 01-9F-CDR-V4 and 01-9F-CDR-V6<br>RILSX1X2TTSYSX3X4VKG (SEQ ID NO: 2) X1 = E, X2 = G, X3 = D, X4 = S<br>RILSEGTTSYSDSVKG |
| $V_H$H CDR2 for 01-9F-CDR-V5 and 01-9F-CDR-V7<br>RILSX1X2TTSYSX3X4VKG (SEQ ID NO: 2) X1 = D, X2 = A, X3 = D, X4 = S<br>RILSDATTSYSDSVKG |
| $V_H$H CDR2 for 01-9F-CDR-V8<br>RILSX1X2TTSYSX3X4VKG (SEQ ID NO: 2) X1 = E, X2 = G, X3 = E, X4 = S<br>RILSEGTTSYSESVKG |
| $V_H$H CDR2 for 01-9F-CDR-V9<br>RILSX1X2TTSYSX3X4VKG (SEQ ID NO: 2) X1 = D, X2 = A, X3 = E, X4 = S<br>RILSDATTSYSESVKG |
| $V_H$H CDR2 for 01-9F-CDR-V10<br>RILSX1X2TTSYSX3X4VKG (SEQ ID NO: 2) X1 = E, X2 = G, X3 = D, X4 = T<br>RILSEGTTSYSDTVKG |
| $V_H$H CDR2 for 01-9F-CDR-V11, 01-9F-CDR-V11-V1 to 01-9F-CDR-V11-V24<br>RILSX1X2TTSYSX3X4VKG (SEQ ID NO: 2) X1 = D, X2 = A, X3 = D, X4 = T<br>RILSDATTSYSDTVKG |
| $V_H$H CDR3 for 01-9F<br>EAFRPFTPSX1X2DCTTVLGIDY (SEQ ID NO: 3) X1 = D, X2 = G<br>EAFRPFTPSDGDCTTVLGIDY |
| $V_H$H CDR3 for 01-9F-CDR-V1, 01-9F-CDR-V4, 01-9F-CDR-V5, 01-9F-CDR-V8 and 01-9F-CDR-V9<br>EAFRPFTPSX1X2DCTTVLGIDY (SEQ ID NO: 3) X1 = E, X2 = G<br>EAFRPFTPSEGDCTTVLGIDY |
| $V_H$H CDR3 for 01-9F-CDR-V2, 01-9F-CDR-V6, 01-9F-CDR-V7, 01-9F-CDR-V10, and 01-9F-CDR-V11, and 01-9F-CDR-V11-V1 to 01-9F-CDR-V11-V24<br>EAFRPFTPSX1X2DCTTVLGIDY (SEQ ID NO: 3) X1 = D, X2 = A<br>EAFRPFTPSDADCTTVLGIDY |
| $V_H$H CDR3 for 01-9F-CDR-V3<br>EAFRPFTPSX1X2DCTTVLGIDY (SEQ ID NO: 3) X1 = I, X2 = G<br>EAFRPFTPSIGDCTTVLGIDY |
| $V_H$H for 01-9F<br>QVQLVESGGGX1VX2AGGSLRLSCVVSGLPYERYCVAWFRQGPGKEREGVARILSDGTTS<br>YSDSVKGRFTISKDNAKNTLYLQMNSLKSEDTATYYCAAEAFRPFTPSX3X4DCTTVLGID<br>YWGKGTX5VTVSS (SEQ ID NO: 4) X1 = S, X2 = Q, X3 = D, X4 = G, X5 = P<br>QVQLVESGGGSVQAGGSLRLSCVVSGLPYERYCVAWFRQGPGKEREGVARILSDGTTSYS<br>DSVKGRFTISKDNAKNTLYLQMNSLKSEDTATYYCAAEAFRPFTPSDGDCTTVLGIDYWG<br>KGTPVTVSS<br>CAAGTGCAACTTGTTGAAAGCGGGGGCGGTAGCGTACAGGCGGGAGGGAGCCTCCGA<br>TTGAGCTGCGTGGTCAGCGGGCTGCCGTATGAGAGATACTGCGTAGCATGGTTCAGGC<br>AAGGCCCGGGTAAAGAGCGAGAGGGAGTAGCTCGGATACTTTCTGACGGTACTACGTC<br>TTATAGTGACTCCGTGAAGGGGCGCTTCACTATTAGCAAGGATAATGCGAAAAACACA<br>TTGTACCTTCAGATGAACAGCCTGAAGAGTGAGGATACGGCTACTTATTATTGTGCAG<br>CGGAAGCATTCCGCCCATTCACACCCTCCGACGGGGATTGTACCACAGTGCTTGGTAT<br>AGACTACTGGGGAAAAGGAACGCCTGTTACTGTGAGCAGC (SEQ ID NO: 23) |
| $V_H$H for 01-9F-CDR-V1<br>QVQLVESGGGX1VX2AGGSLRLSCVVSGLPYERYCVAWFRQGPGKEREGVARILSDGTTS<br>YSDSVKGRFTISKDNAKNTLYLQMNSLKSEDTATYYCAAEAFRPFTPSX3X4DCTTVLGID<br>YWGKGTX5VTVSS (SEQ ID NO: 4) X1 = S, X2 = Q, X3 = E, X4 = G, X5 = P<br>QVQLVESGGGSVQAGGSLRLSCVVSGLPYERYCVAWFRQGPGKEREGVARILSDGTTSYS<br>DSVKGRFTISKDNAKNTLYLQMNSLKSEDTATYYCAAEAFRPFTPSEGDCTTVLGIDYWG<br>KGTPVTVSS |
| $V_H$H for 01-9F-CDR-V2<br>QVQLVESGGGX1VX2AGGSLRLSCVVSGLPYERYCVAWFRQGPGKEREGVARILSDGTTS<br>YSDSVKGRFTISKDNAKNTLYLQMNSLKSEDTATYYCAAEAFRPFTPSX3X4DCTTVLGID<br>YWGKGTX5VTVSS (SEQ ID NO: 4) X1 = S, X2 = Q, X3 = D, X4 = A, X5 = P<br>QVQLVESGGGSVQAGGSLRLSCVVSGLPYERYCVAWFRQGPGKEREGVARILSDGTTSYS<br>DSVKGRFTISKDNAKNTLYLQMNSLKSEDTATYYCAAEAFRPFTPSDADCTTVLGIDYWG<br>KGTPVTVSS |

-continued

| Description/Sequence/SEQ ID NO. |
| --- |
| $V_H$H for 01-9F-CDR-V3<br>QVQLVESGGGX1VX2AGGSLRLSCVVSGLPYERYCVAWFRQGPGKEREGVARILSDGTTS<br>YSDSVKGRFTISKDNAKNTLYLQMNSLKSEDTATYYCAAEAFRPFTPSX3X4DCTTVLGID<br>YWGKGTX5VTVSS (SEQ ID NO: 4) X1 = S, X2 = Q, X3 = I, X4 = G, X5 = P<br>QVQLVESGGGSVQAGGSLRLSCVVSGLPYERYCVAWFRQGPGKEREGVARILSDGTTSYS<br>DSVKGRFTISKDNAKNTLYLQMNSLKSEDTATYYCAAEAFRPFTPSIGDCTTVLGIDYWGK<br>GTPVTVSS |
| $V_H$H for 01-9F-CDR-V4<br>QVQLVESGGGSVQAGGSLRLSCVVSGLPYERYCVAWFRQGPGKEREGVARILSX1X2TTS<br>YSX3SVKGRFTISKDNAKNTLYLQMNSLKSEDTATYYCAAEAFRPFTPSEGDCTTVLGIDY<br>WGKGTPVTVSS (SEQ ID NO: 5) X1 = E, X2 = G, X3 = D<br>QVQLVESGGGSVQAGGSLRLSCVVSGLPYERYCVAWFRQGPGKEREGVARILSEGTTSYS<br>DSVKGRFTISKDNAKNTLYLQMNSLKSEDTATYYCAAEAFRPFTPSEGDCTTVLGIDYWG<br>KGTPVTVSS |
| $V_H$H for 01-9F-CDR-V5<br>QVQLVESGGGSVQAGGSLRLSCVVSGLPYERYCVAWFRQGPGKEREGVARILSX1X2TTS<br>YSX3SVKGRFTISKDNAKNTLYLQMNSLKSEDTATYYCAAEAFRPFTPSEGDCTTVLGIDY<br>WGKGTPVTVSS (SEQ ID NO: 5) X1 = D, X2 = A, X3 = D<br>QVQLVESGGGSVQAGGSLRLSCVVSGLPYERYCVAWFRQGPGKEREGVARILSDATTSYS<br>DSVKGRFTISKDNAKNTLYLQMNSLKSEDTATYYCAAEAFRPFTPSEGDCTTVLGIDYWG<br>KGTPVTVSS |
| $V_H$H for 01-9F-CDR-V8<br>QVQLVESGGGSVQAGGSLRLSCVVSGLPYERYCVAWFRQGPGKEREGVARILSX1X2TTS<br>YSX3SVKGRFTISKDNAKNTLYLQMNSLKSEDTATYYCAAEAFRPFTPSEGDCTTVLGIDY<br>WGKGTPVTVSS (SEQ ID NO: 5) X1 = E, X2 = G, X3 = E<br>QVQLVESGGGSVQAGGSLRLSCVVSGLPYERYCVAWFRQGPGKEREGVARILSEGTTSYS<br>ESVKGRFTISKDNAKNTLYLQMNSLKSEDTATYYCAAEAFRPFTPSEGDCTTVLGIDYWG<br>KGTPVTVSS |
| $V_H$H for 01-9F-CDR-V9<br>QVQLVESGGGSVQAGGSLRLSCVVSGLPYERYCVAWFRQGPGKEREGVARILSX1X2TTS<br>YSX3SVKGRFTISKDNAKNTLYLQMNSLKSEDTATYYCAAEAFRPFTPSEGDCTTVLGIDY<br>WGKGTPVTVSS (SEQ ID NO: 5) X1 = D, X2 = A, X3 = E<br>QVQLVESGGGSVQAGGSLRLSCVVSGLPYERYCVAWFRQGPGKEREGVARILSDATTSYS<br>ESVKGRFTISKDNAKNTLYLQMNSLKSEDTATYYCAAEAFRPFTPSEGDCTTVLGIDYWG<br>KGTPVTVSS |
| $V_H$H for 01-9F-CDR-V6<br>QVQLVESGGGSVQAGGSLRLSCVVSGLPYERYCVAWFRQGPGKEREGVARILSX1X2TTS<br>YSDX3VKGRFTISKDNAKNTLYLQMNSLKSEDTATYYCAAEAFRPFTPSDADCTTVLGIDY<br>WGKGTPVTVSS (SEQ ID NO: 6) X1 = E, X2 = G, X3 = S<br>QVQLVESGGGSVQAGGSLRLSCVVSGLPYERYCVAWFRQGPGKEREGVARILSEGTTSYS<br>DSVKGRFTISKDNAKNTLYLQMNSLKSEDTATYYCAAEAFRPFTPSDADCTTVLGIDYWG<br>KGTPVTVSS |
| $V_H$H for 01-9F-CDR-V7<br>QVQLVESGGGSVQAGGSLRLSCVVSGLPYERYCVAWFRQGPGKEREGVARILSX1X2TTS<br>YSDX3VKGRFTISKDNAKNTLYLQMNSLKSEDTATYYCAAEAFRPFTPSDADCTTVLGIDY<br>WGKGTPVTVSS (SEQ ID NO: 6) X1 = D, X2 = A, X3 = S<br>QVQLVESGGGSVQAGGSLRLSCVVSGLPYERYCVAWFRQGPGKEREGVARILSDATTSYS<br>DSVKGRFTISKDNAKNTLYLQMNSLKSEDTATYYCAAEAFRPFTPSDADCTTVLGIDYWG<br>KGTPVTVSS |
| $V_H$H for 01-9F-CDR-V10<br>QVQLVESGGGSVQAGGSLRLSCVVSGLPYERYCVAWFRQGPGKEREGVARILSX1X2TTS<br>YSDX3VKGRFTISKDNAKNTLYLQMNSLKSEDTATYYCAAEAFRPFTPSDADCTTVLGIDY<br>WGKGTPVTVSS (SEQ ID NO: 6) X1 = E, X2 = G, X3 = T<br>QVQLVESGGGSVQAGGSLRLSCVVSGLPYERYCVAWFRQGPGKEREGVARILSEGTTSYS<br>DTVKGRFTISKDNAKNTLYLQMNSLKSEDTATYYCAAEAFRPFTPSDADCTTVLGIDYWG<br>KGTPVTVSS |
| $V_H$H for 01-9F-CDR-V11<br>QVQLVESGGGSVQAGGSLRLSCVVSGLPYERYCVAWFRQGPGKEREGVARILSX1X2TTS<br>YSDX3VKGRFTISKDNAKNTLYLQMNSLKSEDTATYYCAAEAFRPFTPSDADCTTVLGIDY<br>WGKGTPVTVSS (SEQ ID NO: 6) X1 = D, X2 = A, X3 = T<br>QVQLVESGGGSVQAGGSLRLSCVVSGLPYERYCVAWFRQGPGKEREGVARILSDATTSYS<br>DTVKGRFTISKDNAKNTLYLQMNSLKSEDTATYYCAAEAFRPFTPSDADCTTVLGIDYWG<br>KGTPVTVSS<br>CAAGTGCAACTGGTAGAATCTGGGGGGGGCAGTGTACAAGCTGGGGGCAGCCTGAGA<br>CTGAGCTGTGTGGTGTCTGGCCTGCCCTATGAGAGATACTGTGTGGCCTGGTTCAGACA<br>AGGCCCTGGCAAGGAGAGAGAGGGGGTGGCTAGAATCCTGTCTGATGCCACCACAAG<br>CTACTCTGACACAGTGAAGGGCAGATTCACCATCAGCAAGGACAATGCCAAGAACAC<br>CCTGTACCTGCAGATGAACAGCCTGAAGTCTGAGGACACAGCCACCTACTACTGTGCT |

-continued

Description/Sequence/SEQ ID NO.

GCTGAGGCCTTCAGACCCTTCACCCCCTCTGATGCTGACTGCACCACAGTGCTGGGCAT
TGACTACTGGGGCAAGGGCACCCCTGTGACAGTGAGCTCT (SEQ ID NO: 24)

$V_H$H for 01-9F-CDR-V11-V1
QVQLVESGGGLVQPGGSLRLSCAVSGLPYERYCVAWFRQAPGKGLEGVARILSDATTSYS
DTVKGRFTISKDNAKNTLYLQMNSLKAEDTAVYYCAAEAFRPFTPSDADCTTVLGIDYWG
KGTTVTVSS (SEQ ID NO: 7)

$V_H$H for 01-9F-CDR-V11-V2
EVQLVESGGGLVQPGGSLRLSCAVSGX1TX2SRYCVAWFRQAPGKGLEGVARILSDATTS
YSDTVKGRFTISX3DNAKNSLYLQMNSLRAEDTAVYYCAX4EAFRPFTPSDADCTTVLGID
YWGQGTTVTVSS (SEQ ID NO: 8) X1 = F, X2 = Y, X3 = K, X4 = A
EVQLVESGGGLVQPGGSLRLSCAVSGFTYSRYCVAWFRQAPGKGLEGVARILSDATTSYS
DTVKGRFTISKDNAKNSLYLQMNSLRAEDTAVYYCAAEAFRPFTPSDADCTTVLGIDYWG
QGTTVTVSS $V_H$H for 01-9F-CDR-V11-V3
EVQLVESGGGLVQPGGSLRLSCAVSGX1TX2SRYCVAWFRQAPGKGLEGVARILSDATTS
YSDTVKGRFTISX3DNAKNSLYLQMNSLRAEDTAVYYCAX4EAFRPFTPSDADCTTVLGID
YWGQGTTVTVSS (SEQ ID NO: 8) X1 = L, X2 = F, X3 = K, X4 = A
EVQLVESGGGLVQPGGSLRLSCAVSGLTFSRYCVAWFRQAPGKGLEGVARILSDATTSYS
DTVKGRFTISKDNAKNSLYLQMNSLRAEDTAVYYCAAEAFRPFTPSDADCTTVLGIDYWG
QGTTVTVSS $V_H$H for 01-9F-CDR-V11-V4
EVQLVESGGGLVQPGGSLRLSCAVSGX1TX2SRYCVAWFRQAPGKGLEGVARILSDATTS
YSDTVKGRFTISX3DNAKNSLYLQMNSLRAEDTAVYYCAX4EAFRPFTPSDADCTTVLGID
YWGQGTTVTVSS (SEQ ID NO: 8) X1 = L, X2 = Y, X3 = R, X4 = A
EVQLVESGGGLVQPGGSLRLSCAVSGLTYSRYCVAWFRQAPGKGLEGVARILSDATTSYS
DTVKGRFTISRDNAKNSLYLQMNSLRAEDTAVYYCAAEAFRPFTPSDADCTTVLGIDYWG
QGTTVTVSS $V_H$H for 01-9F-CDR-V11-V5
EVQLVESGGGLVQPGGSLRLSCAVSGX1TX2SRYCVAWFRQAPGKGLEGVARILSDATTS
YSDTVKGRFTISX3DNAKNSLYLQMNSLRAEDTAVYYCAX4EAFRPFTPSDADCTTVLGID
YWGQGTTVTVSS (SEQ ID NO: 8) X1 = L, X2 = Y, X3 = K, X4 = R
EVQLVESGGGLVQPGGSLRLSCAVSGLTYSRYCVAWFRQAPGKGLEGVARILSDATTSYS
DTVKGRFTISKDNAKNSLYLQMNSLRAEDTAVYYCAREAFRPFTPSDADCTTVLGIDYWG
QGTTVTVSS $V_H$H for 01-9F-CDR-V11-V6
EVQLVESGGGLVQPGGSLRLSCAVSGX1TX2SRYCVAWFRQAPGKGLEGVARILSDATTS
YSDTVKGRFTISX3DNAKNSLYLQMNSLRAEDTAVYYCAX4EAFRPFTPSDADCTTVLGID
YWGQGTTVTVSS (SEQ ID NO: 8) X1 = L, X2 = Y, X3 = K, X4 = A
EVQLVESGGGLVQPGGSLRLSCAVSGLTYSRYCVAWFRQAPGKGLEGVARILSDATTSYS
DTVKGRFTISKDNAKNSLYLQMNSLRAEDTAVYYCAAEAFRPFTPSDADCTTVLGIDYWG
QGTTVTVSS $V_H$H for 01-9F-CDR-V11-V7
EVQLVESGGGLVQPGGSLRLSCAASGX1PX2SRYCVAWFRQAPGKGLEGVARILSDATTS
YSDTVKGRFTISX3DNAKNSLYLQMNSLRAEDTAVYYCAX4EAFRPFTPSDADCTTVLGID
YWGQGTTVTVSS (SEQ ID NO: 9) X1 = F, X2 = Y, X3 = K, X4 = A
EVQLVESGGGLVQPGGSLRLSCAASGFPYSRYCVAWFRQAPGKGLEGVARILSDATTSYS
DTVKGRFTISKDNAKNSLYLQMNSLRAEDTAVYYCAAEAFRPFTPSDADCTTVLGIDYWG
QGTTVTVSS $V_H$H for 01-9F-CDR-V11-V8
EVQLVESGGGLVQPGGSLRLSCAASGX1PX2SRYCVAWFRQAPGKGLEGVARILSDATTS
YSDTVKGRFTISX3DNAKNSLYLQMNSLRAEDTAVYYCAX4EAFRPFTPSDADCTTVLGID
YWGQGTTVTVSS (SEQ ID NO: 9) X1 = L, X2 = F, X3 = K, X4 = A
EVQLVESGGGLVQPGGSLRLSCAASGLPFSRYCVAWFRQAPGKGLEGVARILSDATTSYS
DTVKGRFTISKDNAKNSLYLQMNSLRAEDTAVYYCAAEAFRPFTPSDADCTTVLGIDYWG
QGTTVTVSS $V_H$H for 01-9F-CDR-V11-V9
EVQLVESGGGLVQPGGSLRLSCAASGX1PX2SRYCVAWFRQAPGKGLEGVARILSDATTS
YSDTVKGRFTISX3DNAKNSLYLQMNSLRAEDTAVYYCAX4EAFRPFTPSDADCTTVLGID
YWGQGTTVTVSS (SEQ ID NO: 9) X1 = L, X2 = Y, X3 = R, X4 = A
EVQLVESGGGLVQPGGSLRLSCAASGLPYSRYCVAWFRQAPGKGLEGVARILSDATTSYS
DTVKGRFTISRDNAKNSLYLQMNSLRAEDTAVYYCAAEAFRPFTPSDADCTTVLGIDYWG
QGTTVTVSS $V_H$H for 01-9F-CDR-V11-V10
EVQLVESGGGLVQPGGSLRLSCAASGX1PX2SRYCVAWFRQAPGKGLEGVARILSDATTS
YSDTVKGRFTISX3DNAKNSLYLQMNSLRAEDTAVYYCAX4EAFRPFTPSDADCTTVLGID
YWGQGTTVTVSS (SEQ ID NO: 9) X1 = L, X2 = Y, X3 = K, X4 = R
EVQLVESGGGLVQPGGSLRLSCAASGLPYSRYCVAWFRQAPGKGLEGVARILSDATTSYS -continued

| Description/Sequence/SEQ ID NO. |
| --- |
| DTVKGRFTISKDNAKNSLYLQMNSLRAEDTAVYYCAREAFRPFTPSDADCTTVLGIDYWG<br>QGTTVTVSS |
| $V_H$H for 01-9F-CDR-V11-V11<br>EVQLVESGGGLVQPGGSLRLSCAASGX1PX2SRYCVAWFRQAPGKGLEGVARILSDATTS<br>YSDTVKGRFTISX3DNAKNSLYLQMNSLRAEDTAVYYCAX4EAFRPFTPSDADCTTVLGID<br>YWGQGTTVTVSS (SEQ ID NO: 9) X1 = L, X2 = Y, X3 = K, X4 = A<br>EVQLVESGGGLVQPGGSLRLSCAASGLPYSRYCVAWFRQAPGKGLEGVARILSDATTSYS<br>DTVKGRFTISKDNAKNSLYLQMNSLRAEDTAVYYCAAEAFRPFTPSDADCTTVLGIDYWG<br>QGTTVTVSS<br>GAGGTGCAGCTCGTGGAGAGCGGCGGGGGCCTGGTGCAACCTGGCGGGAGCCTGAGA<br>CTGAGCTGCGCCGCTAGCGGCCTGCCCTACAGCAGATACTGCGTGGCCTGGTTCAGAC<br>AAGCCCCCGGCAAGGGCCTGGAGGGCGTGGCTAGAATCCTGAGCGACGCCACCACAA<br>GCTACAGCGACACCGTGAAGGGCAGATTCACCATCAGCAAGGACAACGCCAAGAACA<br>GCCTGTACCTGCAGATGAACAGCCTGAGAGCCGAGGACACCGCCGTGTACTACTGCGC<br>CGCCGAGGCCTTCAGACCCTTCACCCCTAGCGACGCCGACTGCACCACCGTGCTGGGC<br>ATCGACTACTGGGGCCAAGGCACCACCGTGACCGTGAGCAGC (SEQ ID NO: 25) |
| $V_H$H for 01-9F-CDR-V11-V12<br>EVQLVESGGGLVQPGGSLRLSCAASGX1TX2ERYCVAWFRQAPGKGLEGVARILSDATTS<br>YSDTVKGRFTISX3DNAKNSLYLQMNSLRAEDTAVYYCAX4EAFRPFTPSDADCTTVLGID<br>YWGQGTTVTVSS (SEQ ID NO: 10) X1 = F, X2 = Y, X3 = K, X4 = A<br>EVQLVESGGGLVQPGGSLRLSCAASGFTYERYCVAWFRQAPGKGLEGVARILSDATTSYS<br>DTVKGRFTISKDNAKNSLYLQMNSLRAEDTAVYYCAAEAFRPFTPSDADCTTVLGIDYWG<br>QGTTVTVSS |
| $V_H$H for 01-9F-CDR-V11-V13<br>EVQLVESGGGLVQPGGSLRLSCAASGX1TX2ERYCVAWFRQAPGKGLEGVARILSDATTS<br>YSDTVKGRFTISX3DNAKNSLYLQMNSLRAEDTAVYYCAX4EAFRPFTPSDADCTTVLGID<br>YWGQGTTVTVSS (SEQ ID NO: 10) X1 = L, X2 = F, X3 = K, X4 = A<br>EVQLVESGGGLVQPGGSLRLSCAASGLTFERYCVAWFRQAPGKGLEGVARILSDATTSYS<br>DTVKGRFTISKDNAKNSLYLQMNSLRAEDTAVYYCAAEAFRPFTPSDADCTTVLGIDYWG<br>QGTTVTVSS |
| $V_H$H for 01-9F-CDR-V11-V14<br>EVQLVESGGGLVQPGGSLRLSCAASGX1TX2ERYCVAWFRQAPGKGLEGVARILSDATTS<br>YSDTVKGRFTISX3DNAKNSLYLQMNSLRAEDTAVYYCAX4EAFRPFTPSDADCTTVLGID<br>YWGQGTTVTVSS (SEQ ID NO: 10) X1 = L, X2 = Y, X3 = R, X4 = A<br>EVQLVESGGGLVQPGGSLRLSCAASGLTYERYCVAWFRQAPGKGLEGVARILSDATTSYS<br>DTVKGRFTISRDNAKNSLYLQMNSLRAEDTAVYYCAAEAFRPFTPSDADCTTVLGIDYWG<br>QGTTVTVSS |
| $V_H$H for 01-9F-CDR-V11-V15<br>EVQLVESGGGLVQPGGSLRLSCAASGX1TX2ERYCVAWFRQAPGKGLEGVARILSDATTS<br>YSDTVKGRFTISX3DNAKNSLYLQMNSLRAEDTAVYYCAX4EAFRPFTPSDADCTTVLGID<br>YWGQGTTVTVSS (SEQ ID NO: 10) X1 = L, X2 = Y, X3 = K, X4 = R<br>EVQLVESGGGLVQPGGSLRLSCAASGLTYERYCVAWFRQAPGKGLEGVARILSDATTSYS<br>DTVKGRFTISKDNAKNSLYLQMNSLRAEDTAVYYCAREAFRPFTPSDADCTTVLGIDYWG<br>QGTTVTVSS |
| $V_H$H for 01-9F-CDR-V11-V16<br>EVQLVESGGGLVQPGGSLRLSCAASGX1TX2ERYCVAWFRQAPGKGLEGVARILSDATTS<br>YSDTVKGRFTISX3DNAKNSLYLQMNSLRAEDTAVYYCAX4EAFRPFTPSDADCTTVLGID<br>YWGQGTTVTVSS (SEQ ID NO: 10) X1 = L, X2 = Y, X3 = K, X4 = A<br>EVQLVESGGGLVQPGGSLRLSCAASGLTYERYCVAWFRQAPGKGLEGVARILSDATTSYS<br>DTVKGRFTISKDNAKNSLYLQMNSLRAEDTAVYYCAAEAFRPFTPSDADCTTVLGIDYWG<br>QGTTVTVSS |
| $V_H$H for 01-9F-CDR-V11-V17<br>EVQLVESGGGLVQPGGSLRLSCAASGX1TX2SRYCVAWFRQAPGKGLEGVARILSDATTS<br>YSDTVKGRFTISX3DNAKNTLYLQMNSLRAEDTAVYYCAX4EAFRPFTPSDADCTTVLGID<br>YWGKGTTVTVSS (SEQ ID NO: 11) X1 = F, X2 = Y, X3 = K, X4 = A<br>EVQLVESGGGLVQPGGSLRLSCAASGFTYSRYCVAWFRQAPGKGLEGVARILSDATTSYS<br>DTVKGRFTISKDNAKNTLYLQMNSLRAEDTAVYYCAAEAFRPFTPSDADCTTVLGIDYWG<br>KGTTVTVSS |
| $V_H$H for 01-9F-CDR-V11-V18<br>EVQLVESGGGLVQPGGSLRLSCAASGX1TX2SRYCVAWFRQAPGKGLEGVARILSDATTS<br>YSDTVKGRFTISX3DNAKNTLYLQMNSLRAEDTAVYYCAX4EAFRPFTPSDADCTTVLGID<br>YWGKGTTVTVSS (SEQ ID NO: 11) X1 = L, X2 = F, X3 = K, X4 = A<br>EVQLVESGGGLVQPGGSLRLSCAASGLTFSRYCVAWFRQAPGKGLEGVARILSDATTSYS<br>DTVKGRFTISKDNAKNTLYLQMNSLRAEDTAVYYCAAEAFRPFTPSDADCTTVLGIDYWG<br>KGTTVTVSS |
| $V_H$H for 01-9F-CDR-V11-V19<br>EVQLVESGGGLVQPGGSLRLSCAASGX1TX2SRYCVAWFRQAPGKGLEGVARILSDATTS<br>YSDTVKGRFTISX3DNAKNTLYLQMNSLRAEDTAVYYCAX4EAFRPFTPSDADCTTVLGID |

-continued

| Description/Sequence/SEQ ID NO. |
|---|
| YWGKGTTVTVSS (SEQ ID NO: 11) X1 = L, X2 = Y, X3 = R, X4 = A<br>EVQLVESGGGLVQPGGSLRLSCAASGLTYSRYCVAWFRQAPGKGLEGVARILSDATTSYS<br>DTVKGRFTISRDNAKNTLYLQMNSLRAEDTAVYYCAAEAFRPFTPSDADCTTVLGIDYWG<br>KGTTVTVSS |
| $V_H$H for 01-9F-CDR-V11-V20<br>EVQLVESGGGLVQPGGSLRLSCAASGX1TX2SRYCVAWFRQAPGKGLEGVARILSDATTS<br>YSDTVKGRFTISX3DNAKNTLYLQMNSLRAEDTAVYYCAX4EAFRPFTPSDADCTTVLGID<br>YWGKGTTVTVSS (SEQ ID NO: 11) X1 = L, X2 = Y, X3 = K, X4 = R<br>EVQLVESGGGLVQPGGSLRLSCAASGLTYSRYCVAWFRQAPGKGLEGVARILSDATTSYS<br>DTVKGRFTISKDNAKNTLYLQMNSLRAEDTAVYYCAREAFRPFTPSDADCTTVLGIDYWG<br>KGTTVTVSS |
| $V_H$H for 01-9F-CDR-V11-V21<br>EVQLVESGGGLVQPGGSLRLSCAASGX1TX2SRYCVAWFRQAPGKGLEGVARILSDATTS<br>YSDTVKGRFTISX3DNAKNTLYLQMNSLRAEDTAVYYCAX4EAFRPFTPSDADCTTVLGID<br>YWGKGTTVTVSS (SEQ ID NO: 11) X1 = L, X2 = Y, X3 = K, X4 = A<br>EVQLVESGGGLVQPGGSLRLSCAASGLTYSRYCVAWFRQAPGKGLEGVARILSDATTSYS<br>DTVKGRFTISKDNAKNTLYLQMNSLRAEDTAVYYCAAEAFRPFTPSDADCTTVLGIDYWG<br>KGTTVTVSS |
| $V_H$H for 01-9F-CDR-V11-V22<br>QVQLVESGGGLVQPGGSLRLSCAASGGSEYRYCVAWFRQAPGQGLEAVARILSDATTSYS<br>DTVKGRFTISRDNSKNTLYLQMNSLRAEDTAVYYCAAEAFRPFTPSDADCTTVLGIDYWG<br>QGTLVTVSS (SEQ ID NO: 12) |
| $V_H$H for 01-9F-CDR-V11-V23<br>EVQLVESGGGLVQPGGSLRLSCAASGFTVSRYCVAWXIRQAPGKGLEX2VSRILSDATTSY<br>SDTVKGRFTISRDNSKNTLYLQMNSLRAEDTAVYYCAREAFRPFTPSDADCTTVLGIDYW<br>GKGTTVTVSS (SEQ ID NO: 13) X1 = V, X2 = W<br>EVQLVESGGGLVQPGGSLRLSCAASGFTVSRYCVAWVRQAPGKGLEWVSRILSDATTSYS<br>DTVKGRFTISRDNSKNTLYLQMNSLRAEDTAVYYCAREAFRPFTPSDADCTTVLGIDYWG<br>KGTTVTVSS |
| $V_H$H for 01-9F-CDR-V11-V24<br>EVQLVESGGGLVQPGGSLRLSCAASGFTVSRYCVAWXIRQAPGKGLEX2VSRILSDATTSY<br>SDTVKGRFTISRDNSKNTLYLQMNSLRAEDTAVYYCAREAFRPFTPSDADCTTVLGIDYW<br>GKGTTVTVSS (SEQ ID NO: 13) X1 = F, X2 = G<br>EVQLVESGGGLVQPGGSLRLSCAASGFTVSRYCVAWFRQAPGKGLEGVSRILSDATTSYS<br>DTVKGRFTISRDNSKNTLYLQMNSLRAEDTAVYYCAREAFRPFTPSDADCTTVLGIDYWG<br>KGTTVTVSS |
| $V_H$H CDR1 for 01-5A<br>RYCVA (SEQ ID NO: 1) |
| $V_H$H CDR2 for 01-5A<br>RILSX1X2TTSYSX3X4VKG (SEQ ID NO: 2) X1 = D, X2 = G, X3 = D, X4 = S<br>RILSDGTTSYSDSVKG |
| $V_H$H CDR3 for 01-5A<br>EAFRPFTPSX1X2DCTTVLGIDY (SEQ ID NO: 3) X1 = D, X2 = G<br>EAFRPFTPSDGDCTTVLGIDY |
| $V_H$H for camelid 01-5A<br>QVQLVESGGGX1VX2AGGSLRLSCVVSGLPYERYCVAWFRQGPGKEREGVARILSDGTTS<br>YSDSVKGRFTISKDNAKNTLYLQMNSLKSEDTATYYCAAEAFRPFTPSX3X4DCTTVLGID<br>YWGKGTX5VTVSS (SEQ ID NO: 4) X1 = T, X2 = G, X3 = D, X4 = G, X5 = L<br>QVQLVESGGGTVGAGGSLRLSCVVSGLPYERYCVAWFRQGPGKEREGVARILSDGTTSYS<br>DSVKGRFTISKDNAKNTLYLQMNSLKSEDTATYYCAAEAFRPFTPSDGDCTTVLGIDYWG<br>KGTLVTVSS |
| Constant region for heavy chain only antibodies<br>EPKSCDKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEKTIS<br>KAKGQPREPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK (SEQ ID NO: 14)<br>GAGCCCAAAAGCTGTGACAAGACCCACACCTGTCCCCCCTGTCCTGCCCCTGAGCTCC<br>TTGGGGGCCCATCTGTGTTCCTGTTCCCCCCCAAGCCCAAGGACACCCTGATGATCAGC<br>AGAACCCCTGAGGTGACCTGTGTGGTGGTGGATGTGAGCCATGAGGACCCTGAGGTGA<br>AGTTCAACTGGTATGTGGATGGGGTGGAGGTGCACAATGCCAAGACCAAGCCTAGAG<br>AGGAGCAGTACAACAGCACCTACAGAGTGGTGTCTGTGCTGACAGTGCTGCACCAAGA<br>CTGGCTGAATGGCAAGGAGTACAAGTGCAAGGTGAGCAACAAGGCCCTGCCTGCCCC<br>CATTGAGAAGACAATCAGCAAGGCCAAGGGGCAGCCTAGAGAGCCCCAAGTGTACAC<br>CCTGCCCCCTAGCAGAGAGGAGATGACCAAGAACCAAGTGAGCCTGACCTGCCTGGT<br>GAAGGGCTTCTACCCCTCTGACATTGCTGTGGAGTGGGAGAGCAATGGGCAGCCTGAG<br>AACAACTACAAGACCACCCCCCCTGTGCTGGACTCTGATGGCAGCTTCTTCCTGTACA<br>GCAAGCTGACAGTGGACAAGAGCAGATGGCAGCAAGGCAATGTGTTCAGCTGCTCTGT |

-continued

| Description/Sequence/SEQ ID NO. |
|---|
| GATGCATGAGGCCCTGCACAACCACTACACACAGAAGAGCCTGAGCCTGAGCCCTGG CAAGTGA (SEQ ID NO: 26) |
| Human TROP2-Fc protein MDMRVPAQLLGLLLLWFPGSRCHTAAQDNCTCPTNKMTVCSPDGPGGRCQCRALGSGM AVDCSTLTSKCLLLKARMSAPKNARTLVRPSEHALVDNDGLYDPDCDPEGRFKARQCNQ TSVCWCVNSVGVRRTDKGDLSLRCDELVRTHHILIDLRHRPTAGAFNHSDLDAELRRLFR ERYRLHPKFVAAVHYEQPTIQIELRQNTSQKAAGDVDIGDAAYYFERDIKGESLFQGRGGL DLRVRGEPLQVERTLIYYLDEIPPKFSMKRLTEPKSCDKTHTCPPCPAPELLGGPSVFLFPPK PKDTLMISRTPEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQQGNVFSC SVMHEALHNHYTQKSLSLSPGK (SEQ ID NO: 15) |
| Human TROP2-his protein MDMRVPAQLLGLLLLWFPGSRCHTAAQDNCTCPTNKMTVCSPDGPGGRCQCRALGSGM AVDCSTLTSKCLLLKARMSAPKNARTLVRPSEHALVDNDGLYDPDCDPEGRFKARQCNQ TSVCWCVNSVGVRRTDKGDLSLRCDELVRTHHILIDLRHRPTAGAFNHSDLDAELRRLFR ERYRLHPKFVAAVHYEQPTIQIELRQNTSQKAAGDVDIGDAAYYFERDIKGESLFQGRGGL DLRVRGEPLQVERTLIYYLDEIPPKFSMKRLTHHHHHHHHHH (SEQ ID NO: 16) |
| Heavy chain for benchmark (an analog of sacituzumab) SVQLQQSGSELKKPGASVKVSCKASGYTFTNYGMNWVKQAPGQGLKWMGWINTYTGEP TYTDDFKGRFAFSLDTSVSTAYLQISSLKADDTAVYFCARGGFGSSYWYFDVWGQGSLVT VSSASTKGPSVFPLAPSSKSTSGGTAALGCLVKDYFPEPVTVSWNSGALTSGVHTFPAVLQ SSGLYSLSSVVTVPSSSLGTQTYICNVNHKPSNTKVDKRVEPKSCDKTHTCPPCPAPELLGG PSVFLFPPKPKDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQVYTLPPSREE MTKNQVSLTCLVKGFYPSDIAVEWESNGQPENNYKTTPPVLDSDGSFFLYSKLTVDKSRW QQGNVFSCSVMHEALHNHYTQKSLSLSPGK (SEQ ID NO: 17) |
| Light chain for benchmark (an analog of sacituzumab) DIQLTQSPSSLSASVGDRVSITCKASQDVSIAVAWYQQKPGKAPKLLIYSASYRYTGVPDRF SGSGSGTDFTLTISSLQPEDFAVYYCQQHYITPLTFGAGTKVEIKRTVAAPSVFIFPPSDEQL KSGTASVVCLLNNFYPREAKVQWKVDNALQSGNSQESVTEQDSKDSTYSLSSTLTLSKAD YEKHKVYACEVTHQGLSSPVTKSFNRGEC (SEQ ID NO: 18) |
| Cynomolgus monkey TROP2-his protein MARGPGLAPPPLRLPLLLLLLAAVTGHTAAQDNCTCPTNKMTVCSPDGPGGRCQCRALGS GVAVDCSTLTSKCLLLKARMSAPKNARTLVRPNEHALVDNDGLYDPDCDPEGRFKARQC NQTSVCWCVNSVGVRRTDKGDLSLRCDELVRTHHILIDLRHRPTAGAFNHSDLDAELRRL FRERYRLHPKFVAAVHYEQPTIQIELRQNTSQKAAGDVDIGDAAYYFERDVKGESLFQGR GGLDLRVRGEPLQVERTLIYYLDEIPPKFSMKRHHHHHHHHHH (SEQ ID NO: 19) |
| Full length human TROP2 MARGPGLAPPPLRLPLLLLVLAAVTGHTAAQDNCTCPTNKMTVCSPDGPGGRCQCRALGS GMAVDCSTLTSKCLLLKARMSAPKNARTLVRPSEHALVDNDGLYDPDCDPEGRFKARQC NQTSVCWCVNSVGVRRTDKGDLSLRCDELVRTHHILIDLRHRPTAGAFNHSDLDAELRRL FRERYRLHPKFVAAVHYEQPTIQIELRQNTSQKAAGDVDIGDAAYYFERDIKGESLFQGRG GLDLRVRGEPLQVERTLIYYLDEIPPKFSMKRLTAGLIAVIVVVVVALVAGMAVLVITNRR KSGKYKKVEIKELGELRKEPSLGGGGYPYDVPDYA (SEQ ID NO: 20) |
| DTTP-1170 protein MGADDVVDSSKSFVMENFSSYHGTKPGYVDSIQKGIQKPKSGTQGNYDDDWKGFYSTDN KYDAAGYSVDNENPLSGKAGGVVKVTYPGLTKVLALKVDNAETIKKELGLSLTEPLMEQ VGTEEFIKRFGDGASRVVLSLPFAEGSSSVEYINNWEQAKALSVELEINFETRGKRGQDAM YEYMAQACAGNRVRRSVGSSLSCINLDWDVIRDKTKTKIESLKEHGPIKNKMSESPNKTVS EEKAKQYLEEFHQTALEHPELSELKTVTGTNPVFAGANYAAWAVNVAQVIDSETADNLE KTTAALSILPGIGSVMGIADGAVHHNTEEIVAQSIALSSLMVAQAIPLVGELVDIGFAAYNF VESIINLFQVVHNSYNRPAYSPGHKHQVQLVESGGGWVQPGGSLRLSCAASGFTFSDTAM MWVRQAPGKGREWVAAIDTGGGYTYYADSVKGRFTISRDNAKNTLYLQMNSLKPEDTA RYYCAKTYSGNYYSNYTVANYGTTGRGTLVTVSSHHHHHH (SEQ ID NO: 21) |
| DT3C protein MKYLLPTAAAGLLLLAAQPAMAMGADDVVDSSKSFVMENFSSYHGTKPGYVDSIQKGIQ KPKSGTQGNYDDDWKGFYSTDNKYDAAGYSVDNENPLSGKAGGVVKVTYPGLTKVLAL KVDNAETIKKELGLSLTEPLMEQVGTEEFIKRFGDGASRVVLSLPFAEGSSSVEYINNWEQ AKALSVELEINFETRGKRGQDAMYEYMAQACAGNRVRRSVGSSLSCINLDWDVIRDKTK TKIESLKEHGPIKNKMSESPNKTVSEEKAKQYLEEFHQTALEHPELSELKTVTGTNPVFAGA NYAAWAVNVAQVIDSETADNLEKTTAALSILPGIGSVMGIADGAVHHNTEEIVAQSIALSS LMVAQAIPLVGELVDIGFAAYNFVESIINLFQVVHNSYNRPAYSPGHKHIDEILAALPKTDT YKLILNGKTLKGETTTEAVDAATAEKVFKQYANDNGVDGEWTYDDATKTFTVTEKPEVI DASELTPAVTTYKLVINGKTLKGETTTEAVDAATAEKVFKQYANDNGVDGEWTYDDATK TFTVTEKPEVIDASELTPAVTTYKLVINGKTLKGETTTKAVDAETAEKAFKQYANDNGVD GVWTYDDATKTFTVTELEHHHHHH (SEQ ID NO: 22) |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A heavy chain only antibody, or an antigen-binding portion thereof, capable of binding to TROP2, comprising a variable region comprising a CDR1 region, a CDR2 region and a CDR3 region, wherein the CDR1 region, the CDR2 region and the CDR3 region comprise amino acid sequences set forth in (1) SEQ ID NOs: 1, 2 and 3, respectively, wherein $5^{th}$, $6^{th}$, $12^{th}$ and $13^{th}$ amino acid residues in SEQ ID NO: 2 are D, G, D and S, respectively, and $10^{th}$ and $11^{th}$ amino acid residues in SEQ ID NO: 3 are D and G, respectively;

(2) SEQ ID NOs: 1, 2 and 3, respectively, wherein $5^{th}$, $6^{th}$, $12^{th}$ and $13^{th}$ amino acid residues in SEQ ID NO: 2 are D, G, D and S, respectively, and $10^{th}$ and $11^{th}$ amino acid residues in SEQ ID NO: 3 are E and G, respectively;

(3) SEQ ID NOs: 1, 2 and 3, respectively, wherein $5^{th}$, $6^{th}$, $12^{th}$ and $13^{th}$ amino acid residues in SEQ ID NO: 2 are D, G, D and S, respectively, and $10^{th}$ and $11^{th}$ amino acid residues in SEQ ID NO: 3 are D and A, respectively;

(4) SEQ ID NOs: 1, 2 and 3, respectively, wherein $5^{th}$, $6^{th}$, $12^{th}$ and $13^{th}$ amino acid residues in SEQ ID NO: 2 are D, G, D and S, respectively, and $10^{th}$ and $11^{th}$ amino acid residues in SEQ ID NO: 3 are I and G, respectively;

(5) SEQ ID NOs: 1, 2 and 3, respectively, wherein $5^{th}$, $6^{th}$, $12^{th}$ and $13^{th}$ amino acid residues in SEQ ID NO: 2 are E, G, D and S, respectively, and $10^{th}$ and $11^{th}$ amino acid residues in SEQ ID NO: 3 are E and G, respectively;

(6) SEQ ID NOs: 1, 2 and 3, respectively, wherein $5^{th}$, $6^{th}$ $12^{th}$ and $13^{th}$ amino acid residues in SEQ ID NO: 2 are D, A, D and S, respectively, and $10^{th}$ and $11^{th}$ amino acid residues in SEQ ID NO: 3 are E and G, respectively;

(7) SEQ ID NOs: 1, 2 and 3, respectively, wherein $5^{th}$, $6^{th}$, $12^{th}$ and $13^{th}$ amino acid residues in SEQ ID NO: 2 are E, G, D and S, respectively, and $10^{th}$ and $11^{th}$ amino acid residues in SEQ ID NO: 3 are D and A, respectively;

(8) SEQ ID NOs: 1, 2 and 3, respectively, wherein $5^{th}$, $6^{th}$, $12^{th}$ and $13^{th}$ amino acid residues in SEQ ID NO: 2 are D, A, D and S, respectively, and $10^{th}$ and $11^{th}$ amino acid residues in SEQ ID NO: 3 are D and A, respectively;

(9) SEQ ID NOs: 1, 2 and 3, respectively, wherein $5^{th}$, $6^{th}$ $12^{th}$ and $13^{th}$ amino acid residues in SEQ ID NO: 2 are E, G, E and S, respectively, and $10^{th}$ and $11^{th}$ amino acid residues in SEQ ID NO: 3 are E and G, respectively;

(10) SEQ ID NOs: 1, 2 and 3, respectively, wherein $5^{th}$, $6^{th}$, $12^{th}$ and $13^{th}$ amino acid residues in SEQ ID NO: 2 are D, A, E and S, respectively, and $10^{th}$ and $11^{th}$ amino acid residues in SEQ ID NO: 3 are E and G, respectively;

(11) SEQ ID NOs: 1, 2 and 3, respectively, wherein $5^{th}$, $6^{th}$, $12^{th}$ and $13^{th}$ amino acid residues in SEQ ID NO: 2 are E, G, D and T, respectively, and $10^{th}$ and $11^{th}$ amino acid residues in SEQ ID NO: 3 are D and A, respectively; or

(12) SEQ ID NOs: 1, 2 and 3, respectively, wherein $5^{th}$, $6^{th}$, $12^{th}$ and $13^{th}$ amino acid residues in SEQ ID NO: 2 are D, A, D and T, respectively, and $10^{th}$ and $11^{th}$ amino acid residues in SEQ ID NO: 3 are D and A, respectively.

2. The heavy chain only antibody, or the antigen-binding portion thereof, of claim 1, wherein the variable region comprises an amino acid sequence having at least 90%, 91%, 92%, 93%, 94%, 95%, 96%, 97%, 98%, 99% or 100% identity to SEQ ID NOs: 4, 5, 6, 7, 8, 9, 10, 11, 12, or 13, wherein $11^{th}$, $13^{th}$, $107^{th}$, $108^{th}$ and $124^{th}$ amino acid residues in SEQ ID NO: 4 are S, Q, D, G and P, respectively; S, Q, E, G and P, respectively; S, Q, D, A and P, respectively; S, Q, I, G and P, respectively; or T, G, D, G and L, respectively, wherein $54^{th}$, $55^{th}$ and $61^{st}$ amino acid residues in SEQ ID NO: 5 are E, G and D, respectively; D, A and D, respectively; E, G and E, respectively; or D, A and E, respectively, wherein $54^{th}$, $55^{th}$ and $62^{nd}$ amino acid residues in SEQ ID NO: 6 are E, G and S, respectively; D, A and S, respectively; E, G and T, respectively; or D, A and T, respectively, wherein $27^{th}$, $29^{th}$, $71^{st}$ and $97^{th}$ amino acid residues in SEQ ID NO: 8 are F, Y, K and A, respectively; L, F, K and A, respectively; L, Y, R and A, respectively; L, Y, K and R, respectively; or L, Y, K and A, respectively, wherein $27^{th}$, $29^{th}$, $71^{st}$ and $97^{th}$ amino acid residues in SEQ ID NO: 9 are F, Y, K and A, respectively; L, F, K and A, respectively; L, Y, R and A, respectively; L, Y, K and R, respectively; or L, Y, K and A, respectively, wherein $27^{th}$, $29^{th}$, $71^{st}$ and $97^{th}$ amino acid residues in SEQ ID NO: 10 are F, Y, K and A, respectively;

L, F, K and A, respectively; L, Y, R and A, respectively; L, Y, K and R, respectively; or L, Y, K and A, respectively, wherein $27^{th}$, $29^{th}$, $71^{st}$ and $97^{th}$ amino acid residues in SEQ ID NO: 11 are F, Y, K and A, respectively; L, F, K and A, respectively; L, Y, R and A, respectively; L, Y, K and R, respectively; or L, Y, K and A, respectively, and wherein $37^{th}$ and $47^{th}$ amino acid residues in SEQ ID NO: 13 are V and W, respectively; or F and G, respectively.

3. The heavy chain only antibody, or the antigen-binding portion thereof, of claim 1, comprising a constant region comprising the amino acid sequence of SEQ ID NO: 14, linked to the variable region.

4. The heavy chain only antibody, or the antigen-binding portion thereof, of claim 1, which is able to (a) bind human TROP2; (b) bind monkey TROP2; and (c) be internalized by $TROP2^+$ cells.

5. The heavy chain only antibody, or the antigen-binding portion thereof, of claim 1, which is camelid, chimeric or humanized.

6. An immunoconjugate comprising the heavy chain only antibody, or the antigen-binding portion thereof, of claim 1, linked to a toxin, or a radioisotope.

7. The immunoconjugate of claim 6, wherein the toxin is a recombinant protein comprising the amino acid sequence of SEQ ID NO: 22.

8. A pharmaceutical composition comprising the immunoconjugate of claim 6, and a pharmaceutically acceptable carrier, wherein the immunoconjugate comprises the heavy chain only antibody, or the antigen-binding portion thereof, linked to a toxin.

9. A nucleic acid molecule encoding the heavy chain only antibody, or the antigen-binding portion thereof, of claim 1.

10. An expression vector comprising the nucleic acid molecule of claim 9.

11. A host cell comprising the expression vector of claim 10.

12. A pharmaceutical composition comprising the heavy chain only antibody, or antigen-binding portion thereof, of claim 1, and a pharmaceutically acceptable carrier.

13. The pharmaceutical composition of claim 12, further comprising an anti-tumor agent.

14. A method for treating a cancer with TROP2 expression in a subject in need thereof, comprising administering to the subject a therapeutically effective amount of the pharmaceutical composition of claim 12.

15. The method of claim 14, wherein the cancer is selected from the group consisting of breast cancer, colorectal cancer, gastric adenocarcinoma, esophageal cancer, hepatocellular carcinoma, non-small-cell lung cancer, small-cell lung cancer, ovarian epithelial cancer, prostate cancer, pancreatic ductal adenocarcinoma, head and neck cancer, squamous cell cancer, renal cell cancer, urinary bladder neoplasm, cervical cancer, endometrial cancer, follicular thyroid cancer, and glioblastoma multiforme.

16. A method for cancer imaging in a subject in need thereof, comprising administering the subject with the heavy chain only antibody, or the antigen-binding portion thereof, of claim 1, wherein the heavy chain only antibody, or the antigen-binding portion thereof, is radioactively labeled, wherein the cancer exhibits TROP2 expression.

17. A method for treating a cancer with TROP2 expression in a subject in need thereof, comprising administering to the subject a therapeutically effective amount of the pharmaceutical composition of claim 8.

18. The method of claim 17, wherein the disease is cancer is selected from the group consisting of breast cancer, colorectal cancer, gastric adenocarcinoma, esophageal cancer, hepatocellular carcinoma, non-small-cell lung cancer, small-cell lung cancer, ovarian epithelial cancer, prostate cancer, pancreatic ductal adenocarcinoma, head and neck cancer, squamous cell cancer, renal cell cancer, urinary bladder neoplasm, cervical cancer, endometrial cancer, follicular thyroid cancer, and glioblastoma multiforme.

19. A heavy chain only antibody, or an antigen-binding portion thereof, capable of binding to TROP2, comprising a variable region that comprises the amino acid sequence set forth in SEQ ID NOs: 4, 5, 6, 7, 8, 9, 10, 11, 12, or 13, wherein $11^{th}$, $13^{th}$, $107^{th}$, $108^{th}$ and $124^{th}$ amino acid residues in SEQ ID NO: 4 are S, Q, D, G and P, respectively; S, Q, E, G and P, respectively; S, Q, D, A and P, respectively; S, Q, I, G and P, respectively; or T, G, D, G and L, respectively, wherein $54^{th}$, $55^{th}$ and $61^{st}$ amino acid residues in SEQ ID NO: 5 are E, G and D, respectively; D, A and D, respectively; E, G and E, respectively; or D, A and E, respectively, wherein $54^{th}$, $55^{th}$ and $62^{nd}$ amino acid residues in SEQ ID NO: 6 are E, G and S, respectively; D, A and S, respectively; E, G and T, respectively; or D, A and T, respectively, wherein $27^{th}$, $29^{th}$, $71^{st}$ and $97^{th}$ amino acid residues in SEQ ID NO: 8 are F, Y, K and A, respectively; L, F, K and A, respectively; L, Y, R and A, respectively; L, Y, K and R, respectively; or L, Y, K and A, respectively, wherein $27^{th}$, $29^{th}$, $71^{st}$ and $97^{th}$ amino acid residues in SEQ ID NO: 9 are F, Y, K and A, respectively; L, F, K and A, respectively; L, Y, R and A, respectively; L, Y, K and R, respectively; or L, Y, K and A, respectively, wherein $27^{th}$, $29^{th}$, $71^{st}$ and $97^{th}$ amino acid residues in SEQ ID NO: 10 are F, Y, K and A, respectively; L, F, K and A, respectively; L, Y, R and A, respectively; L, Y, K and R, respectively; or L, Y, K and A, respectively, wherein $27^{th}$, $29^{th}$, $71^{st}$ and $97^{th}$ amino acid residues in SEQ ID NO: 11 are F, Y, K and A, respectively; L, F, K and A, respectively; L, Y, R and A, respectively; L, Y, K and R, respectively; or L, Y, K and A, respectively, and wherein $37^{th}$ and $47^{th}$ amino acid residues in SEQ ID NO: 13 are V and W, respectively; or F and G, respectively.

* * * * *

SEQUENCE LISTING

```
<160> NUMBER OF SEQ ID NOS: 26

<210> SEQ ID NO 1
<211> LENGTH: 5
<212> TYPE: PRT
<213> ORGANISM: Artificial Sequence
<220> FEATURE:
<223> OTHER INFORMATION: VHH CDR1 for 01-9F, 01-9F-CDR-V1 to 01-9F-CDR-
      V11, 01-9F-CDR-V11-V1 to 01-9F-CDR-V11-V24

<400> SEQUENCE: 1

Arg Tyr Cys Val Ala
1               5


<210> SEQ ID NO 2
<211> LENGTH: 16
<212> TYPE: PRT
<213> ORGANISM: Artificial Sequence
<220> FEATURE:
<223> OTHER INFORMATION: VHH CDR2 for 01-9F and 01-5A antibodies
<220> FEATURE:
<221> NAME/KEY: misc_feature
<222> LOCATION: (5)..(5)
<223> OTHER INFORMATION: Xaa can be Asp or Glu
<220> FEATURE:
<221> NAME/KEY: misc_feature
<222> LOCATION: (6)..(6)
<223> OTHER INFORMATION: Xaa can be Gly or Ala
<220> FEATURE:
<221> NAME/KEY: misc_feature
<222> LOCATION: (12)..(12)
<223> OTHER INFORMATION: Xaa can be Asp or Glu
<220> FEATURE:
<221> NAME/KEY: misc_feature
<222> LOCATION: (13)..(13)
<223> OTHER INFORMATION: Xaa can be Ser or Thr

<400> SEQUENCE: 2

Arg Ile Leu Ser Xaa Xaa Thr Thr Ser Tyr Ser Xaa Xaa Val Lys Gly
1               5                   10                  15


<210> SEQ ID NO 3
<211> LENGTH: 21
<212> TYPE: PRT
<213> ORGANISM: Artificial Sequence
<220> FEATURE:
<223> OTHER INFORMATION: VHH CDR3 for 01-9F and 01-5A antibodies
<220> FEATURE:
<221> NAME/KEY: misc_feature
<222> LOCATION: (10)..(10)
<223> OTHER INFORMATION: Xaa can be Asp, Glu or Ile
<220> FEATURE:
<221> NAME/KEY: misc_feature
<222> LOCATION: (11)..(11)
<223> OTHER INFORMATION: Xaa can be Gly or Ala

<400> SEQUENCE: 3

Glu Ala Phe Arg Pro Phe Thr Pro Ser Xaa Xaa Asp Cys Thr Thr Val
1               5                   10                  15

Leu Gly Ile Asp Tyr
            20


<210> SEQ ID NO 4
```

```
<211> LENGTH: 129
<212> TYPE: PRT
<213> ORGANISM: Artificial Sequence
<220> FEATURE:
<223> OTHER INFORMATION: VHH of 01-9F, 01-9F-CDR-V1 to 01-9F-CDR-V3, and
      01-5A
<220> FEATURE:
<221> NAME/KEY: misc_feature
<222> LOCATION: (11)..(11)
<223> OTHER INFORMATION: Xaa can be Ser or Thr
<220> FEATURE:
<221> NAME/KEY: misc_feature
<222> LOCATION: (13)..(13)
<223> OTHER INFORMATION: Xaa can be Gln or Gly
<220> FEATURE:
<221> NAME/KEY: misc_feature
<222> LOCATION: (107)..(107)
<223> OTHER INFORMATION: Xaa can be Asp, Glu or Ile
<220> FEATURE:
<221> NAME/KEY: misc_feature
<222> LOCATION: (108)..(108)
<223> OTHER INFORMATION: Xaa can be Gly or Ala
<220> FEATURE:
<221> NAME/KEY: misc_feature
<222> LOCATION: (124)..(124)
<223> OTHER INFORMATION: Xaa can be Pro or Leu

<400> SEQUENCE: 4

Gln Val Gln Leu Val Glu Ser Gly Gly Gly Xaa Val Xaa Ala Gly Gly
1               5                   10                  15

Ser Leu Arg Leu Ser Cys Val Val Ser Gly Leu Pro Tyr Glu Arg Tyr
            20                  25                  30

Cys Val Ala Trp Phe Arg Gln Gly Pro Gly Lys Glu Arg Glu Gly Val
        35                  40                  45

Ala Arg Ile Leu Ser Asp Gly Thr Thr Ser Tyr Ser Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Ser Glu Asp Thr Ala Thr Tyr Tyr Cys Ala
                85                  90                  95

Ala Glu Ala Phe Arg Pro Phe Thr Pro Ser Xaa Xaa Asp Cys Thr Thr
            100                 105                 110

Val Leu Gly Ile Asp Tyr Trp Gly Lys Gly Thr Xaa Val Thr Val Ser
        115                 120                 125

Ser


<210> SEQ ID NO 5
<211> LENGTH: 129
<212> TYPE: PRT
<213> ORGANISM: Artificial Sequence
<220> FEATURE:
<223> OTHER INFORMATION: VHH of 01-9F-CDR-V4, 01-9F-CDR-V5, 01-9F-CDR-V8
      and 01-9F-CDR-V9
<220> FEATURE:
<221> NAME/KEY: misc_feature
<222> LOCATION: (54)..(54)
<223> OTHER INFORMATION: Xaa can be Glu or Asp
<220> FEATURE:
<221> NAME/KEY: misc_feature
<222> LOCATION: (55)..(55)
<223> OTHER INFORMATION: Xaa can be Gly or Ala
<220> FEATURE:
<221> NAME/KEY: misc_feature
<222> LOCATION: (61)..(61)
<223> OTHER INFORMATION: Xaa can be Asp or Glu

<400> SEQUENCE: 5

Gln Val Gln Leu Val Glu Ser Gly Gly Gly Ser Val Gln Ala Gly Gly
```

```
1               5                   10                  15

Ser Leu Arg Leu Ser Cys Val Val Ser Gly Leu Pro Tyr Glu Arg Tyr
            20                  25                  30

Cys Val Ala Trp Phe Arg Gln Gly Pro Gly Lys Glu Arg Glu Gly Val
        35                  40                  45

Ala Arg Ile Leu Ser Xaa Xaa Thr Thr Ser Tyr Ser Xaa Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Ser Glu Asp Thr Ala Thr Tyr Tyr Cys Ala
                85                  90                  95

Ala Glu Ala Phe Arg Pro Phe Thr Pro Ser Glu Gly Asp Cys Thr Thr
            100                 105                 110

Val Leu Gly Ile Asp Tyr Trp Gly Lys Gly Thr Pro Val Thr Val Ser
        115                 120                 125

Ser


<210> SEQ ID NO 6
<211> LENGTH: 129
<212> TYPE: PRT
<213> ORGANISM: Artificial Sequence
<220> FEATURE:
<223> OTHER INFORMATION: VHH of 01-9F-CDR-V6, 01-9F-CDR-V7, 01-9F-CDR-
      V10 and 01-9F-CDR-V11
<220> FEATURE:
<221> NAME/KEY: misc_feature
<222> LOCATION: (54)..(54)
<223> OTHER INFORMATION: Xaa can be Asp or Glu
<220> FEATURE:
<221> NAME/KEY: misc_feature
<222> LOCATION: (55)..(55)
<223> OTHER INFORMATION: Xaa can be Gly or Ala
<220> FEATURE:
<221> NAME/KEY: misc_feature
<222> LOCATION: (62)..(62)
<223> OTHER INFORMATION: Xaa can be Ser or Thr

<400> SEQUENCE: 6

Gln Val Gln Leu Val Glu Ser Gly Gly Gly Ser Val Gln Ala Gly Gly
1               5                   10                  15

Ser Leu Arg Leu Ser Cys Val Val Ser Gly Leu Pro Tyr Glu Arg Tyr
            20                  25                  30

Cys Val Ala Trp Phe Arg Gln Gly Pro Gly Lys Glu Arg Glu Gly Val
        35                  40                  45

Ala Arg Ile Leu Ser Xaa Xaa Thr Thr Ser Tyr Ser Asp Xaa Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Ser Glu Asp Thr Ala Thr Tyr Tyr Cys Ala
                85                  90                  95

Ala Glu Ala Phe Arg Pro Phe Thr Pro Ser Asp Ala Asp Cys Thr Thr
            100                 105                 110

Val Leu Gly Ile Asp Tyr Trp Gly Lys Gly Thr Pro Val Thr Val Ser
        115                 120                 125

Ser


<210> SEQ ID NO 7
<211> LENGTH: 129
<212> TYPE: PRT
<213> ORGANISM: Artificial Sequence
```

<220> FEATURE:
<223> OTHER INFORMATION: VHH of 01-9F-CDR-V11-V1

<400> SEQUENCE: 7

Gln Val Gln Leu Val Glu Ser Gly Gly Gly Leu Val Gln Pro Gly Gly
1 5 10 15

Ser Leu Arg Leu Ser Cys Ala Val Ser Gly Leu Pro Tyr Glu Arg Tyr
20 25 30

Cys Val Ala Trp Phe Arg Gln Ala Pro Gly Lys Gly Leu Glu Gly Val
35 40 45

Ala Arg Ile Leu Ser Asp Ala Thr Thr Ser Tyr Ser Asp Thr Val Lys
50 55 60

Gly Arg Phe Thr Ile Ser Lys Asp Asn Ala Lys Asn Thr Leu Tyr Leu
65 70 75 80

Gln Met Asn Ser Leu Lys Ala Glu Asp Thr Ala Val Tyr Tyr Cys Ala
85 90 95

Ala Glu Ala Phe Arg Pro Phe Thr Pro Ser Asp Ala Asp Cys Thr Thr
100 105 110

Val Leu Gly Ile Asp Tyr Trp Gly Lys Gly Thr Thr Val Thr Val Ser
115 120 125

Ser

<210> SEQ ID NO 8
<211> LENGTH: 129
<212> TYPE: PRT
<213> ORGANISM: Artificial Sequence
<220> FEATURE:
<223> OTHER INFORMATION: VHH of 01-9F-CDR-V11-V2 to 01-9F-CDR-V11-V6
<220> FEATURE:
<221> NAME/KEY: misc_feature
<222> LOCATION: (27)..(27)
<223> OTHER INFORMATION: Xaa can be Phe or Leu
<220> FEATURE:
<221> NAME/KEY: misc_feature
<222> LOCATION: (29)..(29)
<223> OTHER INFORMATION: Xaa can be Tyr or Phe
<220> FEATURE:
<221> NAME/KEY: misc_feature
<222> LOCATION: (71)..(71)
<223> OTHER INFORMATION: Xaa can be Lys or Arg
<220> FEATURE:
<221> NAME/KEY: misc_feature
<222> LOCATION: (97)..(97)
<223> OTHER INFORMATION: Xaa can be Ala or Arg

<400> SEQUENCE: 8

Glu Val Gln Leu Val Glu Ser Gly Gly Gly Leu Val Gln Pro Gly Gly
1 5 10 15

Ser Leu Arg Leu Ser Cys Ala Val Ser Gly Xaa Thr Xaa Ser Arg Tyr
20 25 30

Cys Val Ala Trp Phe Arg Gln Ala Pro Gly Lys Gly Leu Glu Gly Val
35 40 45

Ala Arg Ile Leu Ser Asp Ala Thr Thr Ser Tyr Ser Asp Thr Val Lys
50 55 60

Gly Arg Phe Thr Ile Ser Xaa Asp Asn Ala Lys Asn Ser Leu Tyr Leu
65 70 75 80

Gln Met Asn Ser Leu Arg Ala Glu Asp Thr Ala Val Tyr Tyr Cys Ala
85 90 95

Xaa Glu Ala Phe Arg Pro Phe Thr Pro Ser Asp Ala Asp Cys Thr Thr
100 105 110

Val Leu Gly Ile Asp Tyr Trp Gly Gln Gly Thr Thr Val Thr Val Ser

```
        115                 120                 125

Ser


<210> SEQ ID NO 9
<211> LENGTH: 129
<212> TYPE: PRT
<213> ORGANISM: Artificial Sequence
<220> FEATURE:
<223> OTHER INFORMATION: VHH of 01-9F-CDR-V11-V7 to 01-9F-CDR-V11-V11
<220> FEATURE:
<221> NAME/KEY: misc_feature
<222> LOCATION: (27)..(27)
<223> OTHER INFORMATION: Xaa can be Phe or Leu
<220> FEATURE:
<221> NAME/KEY: misc_feature
<222> LOCATION: (29)..(29)
<223> OTHER INFORMATION: Xaa can be Tyr or Phe
<220> FEATURE:
<221> NAME/KEY: misc_feature
<222> LOCATION: (71)..(71)
<223> OTHER INFORMATION: Xaa can be Lys or Arg
<220> FEATURE:
<221> NAME/KEY: misc_feature
<222> LOCATION: (97)..(97)
<223> OTHER INFORMATION: Xaa can be Ala or Arg

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Xaa Pro Xaa Ser Arg Tyr
            20                  25                  30

Cys Val Ala Trp Phe Arg Gln Ala Pro Gly Lys Gly Leu Glu Gly Val
        35                  40                  45

Ala Arg Ile Leu Ser Asp Ala Thr Thr Ser Tyr Ser Asp Thr Val Lys
    50                  55                  60

Gly Arg Phe Thr Ile Ser Xaa Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Xaa Glu Ala Phe Arg Pro Phe Thr Pro Ser Asp Ala Asp Cys Thr Thr
            100                 105                 110

Val Leu Gly Ile Asp Tyr Trp Gly Gln Gly Thr Thr Val Thr Val Ser
        115                 120                 125

Ser


<210> SEQ ID NO 10
<211> LENGTH: 129
<212> TYPE: PRT
<213> ORGANISM: Artificial Sequence
<220> FEATURE:
<223> OTHER INFORMATION: VHH of 01-9F-CDR-V11-V12 to 01-9F-CDR-V11-V16
<220> FEATURE:
<221> NAME/KEY: misc_feature
<222> LOCATION: (27)..(27)
<223> OTHER INFORMATION: Xaa can be Phe or Leu
<220> FEATURE:
<221> NAME/KEY: misc_feature
<222> LOCATION: (29)..(29)
<223> OTHER INFORMATION: Xaa can be Tyr or Phe
<220> FEATURE:
<221> NAME/KEY: misc_feature
<222> LOCATION: (71)..(71)
<223> OTHER INFORMATION: Xaa can be Lys or Arg
<220> FEATURE:
<221> NAME/KEY: misc_feature
<222> LOCATION: (97)..(97)
<223> OTHER INFORMATION: Xaa can be Ala or Arg
```

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Xaa Thr Xaa Glu Arg Tyr
            20                  25                  30

Cys Val Ala Trp Phe Arg Gln Ala Pro Gly Lys Gly Leu Glu Gly Val
        35                  40                  45

Ala Arg Ile Leu Ser Asp Ala Thr Thr Ser Tyr Ser Asp Thr Val Lys
    50                  55                  60

Gly Arg Phe Thr Ile Ser Xaa Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Xaa Glu Ala Phe Arg Pro Phe Thr Pro Ser Asp Ala Asp Cys Thr Thr
            100                 105                 110

Val Leu Gly Ile Asp Tyr Trp Gly Gln Gly Thr Thr Val Thr Val Ser
        115                 120                 125

Ser
```

<210> SEQ ID NO 11
<211> LENGTH: 129
<212> TYPE: PRT
<213> ORGANISM: Artificial Sequence
<220> FEATURE:
<223> OTHER INFORMATION: VHH of 01-9F-CDR-V11-V17 to 01-9F-CDR-V11-V21
<220> FEATURE:
<221> NAME/KEY: misc_feature
<222> LOCATION: (27)..(27)
<223> OTHER INFORMATION: Xaa can be Phe or Leu
<220> FEATURE:
<221> NAME/KEY: misc_feature
<222> LOCATION: (29)..(29)
<223> OTHER INFORMATION: Xaa can be Tyr or Phe
<220> FEATURE:
<221> NAME/KEY: misc_feature
<222> LOCATION: (71)..(71)
<223> OTHER INFORMATION: Xaa can be Lys or Arg
<220> FEATURE:
<221> NAME/KEY: misc_feature
<222> LOCATION: (97)..(97)
<223> OTHER INFORMATION: Xaa can be Ala or Arg

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Xaa Thr Xaa Ser Arg Tyr
            20                  25                  30

Cys Val Ala Trp Phe Arg Gln Ala Pro Gly Lys Gly Leu Glu Gly Val
        35                  40                  45

Ala Arg Ile Leu Ser Asp Ala Thr Thr Ser Tyr Ser Asp Thr Val Lys
    50                  55                  60

Gly Arg Phe Thr Ile Ser Xaa Asp Asn Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Xaa Glu Ala Phe Arg Pro Phe Thr Pro Ser Asp Ala Asp Cys Thr Thr
            100                 105                 110

Val Leu Gly Ile Asp Tyr Trp Gly Lys Gly Thr Thr Val Thr Val Ser
        115                 120                 125
```

Ser

<210> SEQ ID NO 12
<211> LENGTH: 129
<212> TYPE: PRT
<213> ORGANISM: Artificial Sequence
<220> FEATURE:
<223> OTHER INFORMATION: VHH of 01-9F-CDR-V11-V22

<400> SEQUENCE: 12

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Glu Tyr Arg Tyr
            20                  25                  30

Cys Val Ala Trp Phe Arg Gln Ala Pro Gly Gln Gly Leu Glu Ala Val
        35                  40                  45

Ala Arg Ile Leu Ser Asp Ala Thr Thr Ser Tyr Ser Asp Thr Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Glu Ala Phe Arg Pro Phe Thr Pro Ser Asp Ala Asp Cys Thr Thr
            100                 105                 110

Val Leu Gly Ile Asp Tyr Trp Gly Gln Gly Thr Leu Val Thr Val Ser
        115                 120                 125

Ser
```

<210> SEQ ID NO 13
<211> LENGTH: 129
<212> TYPE: PRT
<213> ORGANISM: Artificial Sequence
<220> FEATURE:
<223> OTHER INFORMATION: VHH of 01-9F-CDR-V11-V23 and 01-9F-CDR-V11-V24
<220> FEATURE:
<221> NAME/KEY: misc_feature
<222> LOCATION: (37)..(37)
<223> OTHER INFORMATION: Xaa can be Val or Phe
<220> FEATURE:
<221> NAME/KEY: misc_feature
<222> LOCATION: (47)..(47)
<223> OTHER INFORMATION: Xaa can be Trp or Gly

<400> SEQUENCE: 13

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Arg Tyr
            20                  25                  30

Cys Val Ala Trp Xaa Arg Gln Ala Pro Gly Lys Gly Leu Glu Xaa Val
        35                  40                  45

Ser Arg Ile Leu Ser Asp Ala Thr Thr Ser Tyr Ser Asp Thr Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Ala Phe Arg Pro Phe Thr Pro Ser Asp Ala Asp Cys Thr Thr
            100                 105                 110

Val Leu Gly Ile Asp Tyr Trp Gly Lys Gly Thr Thr Val Thr Val Ser
        115                 120                 125
```

Ser

<210> SEQ ID NO 14
<211> LENGTH: 232
<212> TYPE: PRT
<213> ORGANISM: Artificial Sequence
<220> FEATURE:
<223> OTHER INFORMATION: Constant region for heavy chain only antibodies

<400> SEQUENCE: 14

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 15
<211> LENGTH: 502
<212> TYPE: PRT
<213> ORGANISM: Artificial Sequence
<220> FEATURE:
<223> OTHER INFORMATION: Human TROP2-Fc protein

<400> SEQUENCE: 15

```
Met Asp Met Arg Val Pro Ala Gln Leu Leu Gly Leu Leu Leu Leu Trp
1               5                   10                  15

Phe Pro Gly Ser Arg Cys His Thr Ala Ala Gln Asp Asn Cys Thr Cys
            20                  25                  30

Pro Thr Asn Lys Met Thr Val Cys Ser Pro Asp Gly Pro Gly Gly Arg
        35                  40                  45

Cys Gln Cys Arg Ala Leu Gly Ser Gly Met Ala Val Asp Cys Ser Thr
    50                  55                  60
```

```
Leu Thr Ser Lys Cys Leu Leu Leu Lys Ala Arg Met Ser Ala Pro Lys
65                  70                  75                  80

Asn Ala Arg Thr Leu Val Arg Pro Ser Glu His Ala Leu Val Asp Asn
                85                  90                  95

Asp Gly Leu Tyr Asp Pro Asp Cys Asp Pro Glu Gly Arg Phe Lys Ala
            100                 105                 110

Arg Gln Cys Asn Gln Thr Ser Val Cys Trp Cys Val Asn Ser Val Gly
        115                 120                 125

Val Arg Arg Thr Asp Lys Gly Asp Leu Ser Leu Arg Cys Asp Glu Leu
    130                 135                 140

Val Arg Thr His His Ile Leu Ile Asp Leu Arg His Arg Pro Thr Ala
145                 150                 155                 160

Gly Ala Phe Asn His Ser Asp Leu Asp Ala Glu Leu Arg Arg Leu Phe
                165                 170                 175

Arg Glu Arg Tyr Arg Leu His Pro Lys Phe Val Ala Ala Val His Tyr
            180                 185                 190

Glu Gln Pro Thr Ile Gln Ile Glu Leu Arg Gln Asn Thr Ser Gln Lys
        195                 200                 205

Ala Ala Gly Asp Val Asp Ile Gly Asp Ala Ala Tyr Tyr Phe Glu Arg
    210                 215                 220

Asp Ile Lys Gly Glu Ser Leu Phe Gln Gly Arg Gly Gly Leu Asp Leu
225                 230                 235                 240

Arg Val Arg Gly Glu Pro Leu Gln Val Glu Arg Thr Leu Ile Tyr Tyr
                245                 250                 255

Leu Asp Glu Ile Pro Pro Lys Phe Ser Met Lys Arg Leu Thr Glu Pro
            260                 265                 270

Lys Ser Cys Asp Lys Thr His Thr Cys Pro Pro Cys Pro Ala Pro Glu
        275                 280                 285

Leu Leu Gly Gly Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Lys Val Ser Asn Lys Ala Leu Pro
    370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Glu Glu Met Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480
```

```
Ser Val Met His Glu Ala Leu His Asn His Tyr Thr Gln Lys Ser Leu
                485                 490                 495

Ser Leu Ser Pro Gly Lys
            500


<210> SEQ ID NO 16
<211> LENGTH: 280
<212> TYPE: PRT
<213> ORGANISM: Artificial Sequence
<220> FEATURE:
<223> OTHER INFORMATION: Human TROP2-his protein

<400> SEQUENCE: 16

Met Asp Met Arg Val Pro Ala Gln Leu Leu Gly Leu Leu Leu Leu Trp
1               5                   10                  15

Phe Pro Gly Ser Arg Cys His Thr Ala Ala Gln Asp Asn Cys Thr Cys
            20                  25                  30

Pro Thr Asn Lys Met Thr Val Cys Ser Pro Asp Gly Pro Gly Gly Arg
        35                  40                  45

Cys Gln Cys Arg Ala Leu Gly Ser Gly Met Ala Val Asp Cys Ser Thr
    50                  55                  60

Leu Thr Ser Lys Cys Leu Leu Leu Lys Ala Arg Met Ser Ala Pro Lys
65                  70                  75                  80

Asn Ala Arg Thr Leu Val Arg Pro Ser Glu His Ala Leu Val Asp Asn
                85                  90                  95

Asp Gly Leu Tyr Asp Pro Asp Cys Asp Pro Glu Gly Arg Phe Lys Ala
            100                 105                 110

Arg Gln Cys Asn Gln Thr Ser Val Cys Trp Cys Val Asn Ser Val Gly
        115                 120                 125

Val Arg Arg Thr Asp Lys Gly Asp Leu Ser Leu Arg Cys Asp Glu Leu
    130                 135                 140

Val Arg Thr His His Ile Leu Ile Asp Leu Arg His Arg Pro Thr Ala
145                 150                 155                 160

Gly Ala Phe Asn His Ser Asp Leu Asp Ala Glu Leu Arg Arg Leu Phe
                165                 170                 175

Arg Glu Arg Tyr Arg Leu His Pro Lys Phe Val Ala Ala Val His Tyr
            180                 185                 190

Glu Gln Pro Thr Ile Gln Ile Glu Leu Arg Gln Asn Thr Ser Gln Lys
        195                 200                 205

Ala Ala Gly Asp Val Asp Ile Gly Asp Ala Ala Tyr Tyr Phe Glu Arg
    210                 215                 220

Asp Ile Lys Gly Glu Ser Leu Phe Gln Gly Arg Gly Gly Leu Asp Leu
225                 230                 235                 240

Arg Val Arg Gly Glu Pro Leu Gln Val Glu Arg Thr Leu Ile Tyr Tyr
                245                 250                 255

Leu Asp Glu Ile Pro Pro Lys Phe Ser Met Lys Arg Leu Thr His His
            260                 265                 270

His His His His His His His His
        275                 280


<210> SEQ ID NO 17
<211> LENGTH: 451
<212> TYPE: PRT
<213> ORGANISM: Artificial Sequence
<220> FEATURE:
<223> OTHER INFORMATION: Heavy chain of sacituzumab

<400> SEQUENCE: 17
```

```
Ser Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Ser Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 18
<211> LENGTH: 214
<212> TYPE: PRT
<213> ORGANISM: Artificial Sequence
<220> FEATURE:
<223> OTHER INFORMATION: Light chain of sacituzumab

<400> SEQUENCE: 18

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 19
<211> LENGTH: 282
<212> TYPE: PRT
<213> ORGANISM: Artificial Sequence
<220> FEATURE:
<223> OTHER INFORMATION: Cynomolgus monkey TROP2-his protein

<400> SEQUENCE: 19

Met Ala Arg Gly Pro Gly Leu Ala Pro Pro Pro Leu Arg Leu Pro Leu
1               5                   10                  15

Leu Leu Leu Leu Leu Ala Ala Val Thr Gly His Thr Ala Ala Gln Asp
            20                  25                  30

Asn Cys Thr Cys Pro Thr Asn Lys Met Thr Val Cys Ser Pro Asp Gly
        35                  40                  45
```

```
Pro Gly Gly Arg Cys Gln Cys Arg Ala Leu Gly Ser Gly Val Ala Val
    50                  55                  60

Asp Cys Ser Thr Leu Thr Ser Lys Cys Leu Leu Leu Lys Ala Arg Met
65                  70                  75                  80

Ser Ala Pro Lys Asn Ala Arg Thr Leu Val Arg Pro Asn Glu His Ala
                85                  90                  95

Leu Val Asp Asn Asp Gly Leu Tyr Asp Pro Asp Cys Asp Pro Glu Gly
            100                 105                 110

Arg Phe Lys Ala Arg Gln Cys Asn Gln Thr Ser Val Cys Trp Cys Val
        115                 120                 125

Asn Ser Val Gly Val Arg Arg Thr Asp Lys Gly Asp Leu Ser Leu Arg
    130                 135                 140

Cys Asp Glu Leu Val Arg Thr His His Ile Leu Ile Asp Leu Arg His
145                 150                 155                 160

Arg Pro Thr Ala Gly Ala Phe Asn His Ser Asp Leu Asp Ala Glu Leu
                165                 170                 175

Arg Arg Leu Phe Arg Glu Arg Tyr Arg Leu His Pro Lys Phe Val Ala
            180                 185                 190

Ala Val His Tyr Glu Gln Pro Thr Ile Gln Ile Glu Leu Arg Gln Asn
        195                 200                 205

Thr Ser Gln Lys Ala Ala Gly Asp Val Asp Ile Gly Asp Ala Ala Tyr
    210                 215                 220

Tyr Phe Glu Arg Asp Val Lys Gly Glu Ser Leu Phe Gln Gly Arg Gly
225                 230                 235                 240

Gly Leu Asp Leu Arg Val Arg Gly Glu Pro Leu Gln Val Glu Arg Thr
                245                 250                 255

Leu Ile Tyr Tyr Leu Asp Glu Ile Pro Pro Lys Phe Ser Met Lys Arg
            260                 265                 270

His His His His His His His His His His
        275                 280
```

```
<210> SEQ ID NO 20
<211> LENGTH: 336
<212> TYPE: PRT
<213> ORGANISM: Artificial Sequence
<220> FEATURE:
<223> OTHER INFORMATION: Full length human TROP2

<400> SEQUENCE: 20

Met Ala Arg Gly Pro Gly Leu Ala Pro Pro Pro Leu Arg Leu Pro Leu
1               5                   10                  15

Leu Leu Leu Val Leu Ala Ala Val Thr Gly His Thr Ala Ala Gln Asp
            20                  25                  30

Asn Cys Thr Cys Pro Thr Asn Lys Met Thr Val Cys Ser Pro Asp Gly
        35                  40                  45

Pro Gly Gly Arg Cys Gln Cys Arg Ala Leu Gly Ser Gly Met Ala Val
    50                  55                  60

Asp Cys Ser Thr Leu Thr Ser Lys Cys Leu Leu Leu Lys Ala Arg Met
65                  70                  75                  80

Ser Ala Pro Lys Asn Ala Arg Thr Leu Val Arg Pro Ser Glu His Ala
                85                  90                  95

Leu Val Asp Asn Asp Gly Leu Tyr Asp Pro Asp Cys Asp Pro Glu Gly
            100                 105                 110

Arg Phe Lys Ala Arg Gln Cys Asn Gln Thr Ser Val Cys Trp Cys Val
        115                 120                 125
```

```
Asn Ser Val Gly Val Arg Arg Thr Asp Lys Gly Asp Leu Ser Leu Arg
    130                 135                 140

Cys Asp Glu Leu Val Arg Thr His His Ile Leu Ile Asp Leu Arg His
145                 150                 155                 160

Arg Pro Thr Ala Gly Ala Phe Asn His Ser Asp Leu Asp Ala Glu Leu
                165                 170                 175

Arg Arg Leu Phe Arg Glu Arg Tyr Arg Leu His Pro Lys Phe Val Ala
            180                 185                 190

Ala Val His Tyr Glu Gln Pro Thr Ile Gln Ile Glu Leu Arg Gln Asn
        195                 200                 205

Thr Ser Gln Lys Ala Ala Gly Asp Val Asp Ile Gly Asp Ala Ala Tyr
    210                 215                 220

Tyr Phe Glu Arg Asp Ile Lys Gly Glu Ser Leu Phe Gln Gly Arg Gly
225                 230                 235                 240

Gly Leu Asp Leu Arg Val Arg Gly Glu Pro Leu Gln Val Glu Arg Thr
                245                 250                 255

Leu Ile Tyr Tyr Leu Asp Glu Ile Pro Pro Lys Phe Ser Met Lys Arg
            260                 265                 270

Leu Thr Ala Gly Leu Ile Ala Val Ile Val Val Val Val Val Ala Leu
        275                 280                 285

Val Ala Gly Met Ala Val Leu Val Ile Thr Asn Arg Arg Lys Ser Gly
    290                 295                 300

Lys Tyr Lys Lys Val Glu Ile Lys Glu Leu Gly Glu Leu Arg Lys Glu
305                 310                 315                 320

Pro Ser Leu Gly Gly Gly Gly Tyr Pro Tyr Asp Val Pro Asp Tyr Ala
                325                 330                 335
```

<210> SEQ ID NO 21
<211> LENGTH: 519
<212> TYPE: PRT
<213> ORGANISM: Artificial Sequence
<220> FEATURE:
<223> OTHER INFORMATION: DTTP-1170 protein

<400> SEQUENCE: 21

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160
```

```
Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys His Gln Val Gln Leu Val Glu Ser Gly Gly Gly Trp Val Gln
385                 390                 395                 400

Pro Gly Gly Ser Leu Arg Leu Ser Cys Ala Ala Ser Gly Phe Thr Phe
                405                 410                 415

Ser Asp Thr Ala Met Met Trp Val Arg Gln Ala Pro Gly Lys Gly Arg
            420                 425                 430

Glu Trp Val Ala Ala Ile Asp Thr Gly Gly Gly Tyr Thr Tyr Tyr Ala
        435                 440                 445

Asp Ser Val Lys Gly Arg Phe Thr Ile Ser Arg Asp Asn Ala Lys Asn
    450                 455                 460

Thr Leu Tyr Leu Gln Met Asn Ser Leu Lys Pro Glu Asp Thr Ala Arg
465                 470                 475                 480

Tyr Tyr Cys Ala Lys Thr Tyr Ser Gly Asn Tyr Tyr Ser Asn Tyr Thr
                485                 490                 495

Val Ala Asn Tyr Gly Thr Thr Gly Arg Gly Thr Leu Val Thr Val Ser
            500                 505                 510

Ser His His His His His His
        515
```

<210> SEQ ID NO 22
<211> LENGTH: 624
<212> TYPE: PRT
<213> ORGANISM: Artificial Sequence
<220> FEATURE:
<223> OTHER INFORMATION: DT3C protein

<400> SEQUENCE: 22

```
Met Lys Tyr Leu Leu Pro Thr Ala Ala Ala Gly Leu Leu Leu Leu Ala
1               5                   10                  15

Ala Gln Pro Ala Met Ala Met Gly Ala Asp Asp Val Val Asp Ser Ser
            20                  25                  30

Lys Ser Phe Val Met Glu Asn Phe Ser Ser Tyr His Gly Thr Lys Pro
        35                  40                  45

Gly Tyr Val Asp Ser Ile Gln Lys Gly Ile Gln Lys Pro Lys Ser Gly
    50                  55                  60

Thr Gln Gly Asn Tyr Asp Asp Asp Trp Lys Gly Phe Tyr Ser Thr Asp
65                  70                  75                  80

Asn Lys Tyr Asp Ala Ala Gly Tyr Ser Val Asp Asn Glu Asn Pro Leu
                85                  90                  95

Ser Gly Lys Ala Gly Gly Val Val Lys Val Thr Tyr Pro Gly Leu Thr
            100                 105                 110

Lys Val Leu Ala Leu Lys Val Asp Asn Ala Glu Thr Ile Lys Lys Glu
        115                 120                 125

Leu Gly Leu Ser Leu Thr Glu Pro Leu Met Glu Gln Val Gly Thr Glu
    130                 135                 140

Glu Phe Ile Lys Arg Phe Gly Asp Gly Ala Ser Arg Val Val Leu Ser
145                 150                 155                 160

Leu Pro Phe Ala Glu Gly Ser Ser Ser Val Glu Tyr Ile Asn Asn Trp
                165                 170                 175

Glu Gln Ala Lys Ala Leu Ser Val Glu Leu Glu Ile Asn Phe Glu Thr
            180                 185                 190

Arg Gly Lys Arg Gly Gln Asp Ala Met Tyr Glu Tyr Met Ala Gln Ala
        195                 200                 205

Cys Ala Gly Asn Arg Val Arg Arg Ser Val Gly Ser Ser Leu Ser Cys
    210                 215                 220

Ile Asn Leu Asp Trp Asp Val Ile Arg Asp Lys Thr Lys Thr Lys Ile
225                 230                 235                 240

Glu Ser Leu Lys Glu His Gly Pro Ile Lys Asn Lys Met Ser Glu Ser
                245                 250                 255

Pro Asn Lys Thr Val Ser Glu Glu Lys Ala Lys Gln Tyr Leu Glu Glu
            260                 265                 270

Phe His Gln Thr Ala Leu Glu His Pro Glu Leu Ser Glu Leu Lys Thr
        275                 280                 285

Val Thr Gly Thr Asn Pro Val Phe Ala Gly Ala Asn Tyr Ala Ala Trp
    290                 295                 300

Ala Val Asn Val Ala Gln Val Ile Asp Ser Glu Thr Ala Asp Asn Leu
305                 310                 315                 320

Glu Lys Thr Thr Ala Ala Leu Ser Ile Leu Pro Gly Ile Gly Ser Val
                325                 330                 335

Met Gly Ile Ala Asp Gly Ala Val His His Asn Thr Glu Glu Ile Val
            340                 345                 350

Ala Gln Ser Ile Ala Leu Ser Ser Leu Met Val Ala Gln Ala Ile Pro
        355                 360                 365

Leu Val Gly Glu Leu Val Asp Ile Gly Phe Ala Ala Tyr Asn Phe Val
    370                 375                 380

Glu Ser Ile Ile Asn Leu Phe Gln Val Val His Asn Ser Tyr Asn Arg
385                 390                 395                 400

Pro Ala Tyr Ser Pro Gly His Lys His Ile Asp Glu Ile Leu Ala Ala
                405                 410                 415
```

```
Leu Pro Lys Thr Asp Thr Tyr Lys Leu Ile Leu Asn Gly Lys Thr Leu
            420                 425                 430

Lys Gly Glu Thr Thr Thr Glu Ala Val Asp Ala Ala Thr Ala Glu Lys
        435                 440                 445

Val Phe Lys Gln Tyr Ala Asn Asp Asn Gly Val Asp Gly Glu Trp Thr
    450                 455                 460

Tyr Asp Asp Ala Thr Lys Thr Phe Thr Val Thr Glu Lys Pro Glu Val
465                 470                 475                 480

Ile Asp Ala Ser Glu Leu Thr Pro Ala Val Thr Thr Tyr Lys Leu Val
                485                 490                 495

Ile Asn Gly Lys Thr Leu Lys Gly Glu Thr Thr Thr Glu Ala Val Asp
            500                 505                 510

Ala Ala Thr Ala Glu Lys Val Phe Lys Gln Tyr Ala Asn Asp Asn Gly
        515                 520                 525

Val Asp Gly Glu Trp Thr Tyr Asp Asp Ala Thr Lys Thr Phe Thr Val
    530                 535                 540

Thr Glu Lys Pro Glu Val Ile Asp Ala Ser Glu Leu Thr Pro Ala Val
545                 550                 555                 560

Thr Thr Tyr Lys Leu Val Ile Asn Gly Lys Thr Leu Lys Gly Glu Thr
                565                 570                 575

Thr Thr Lys Ala Val Asp Ala Glu Thr Ala Glu Lys Ala Phe Lys Gln
            580                 585                 590

Tyr Ala Asn Asp Asn Gly Val Asp Gly Val Trp Thr Tyr Asp Asp Ala
        595                 600                 605

Thr Lys Thr Phe Thr Val Thr Glu Leu Glu His His His His His His
    610                 615                 620
```

<210> SEQ ID NO 23
<211> LENGTH: 387
<212> TYPE: DNA
<213> ORGANISM: Artificial Sequence
<220> FEATURE:
<223> OTHER INFORMATION: VHH for 01-9F

<400> SEQUENCE: 23

```
caagtgcaac ttgttgaaag cgggggcggt agcgtacagg cgggagggag cctccgattg     60

agctgcgtgg tcagcgggct gccgtatgag agatactgcg tagcatggtt caggcaaggc    120

ccgggtaaag agcgagaggg agtagctcgg atactttctg acggtactac gtcttatagt    180

gactccgtga aggggcgctt cactattagc aaggataatg cgaaaaacac attgtacctt    240

cagatgaaca gcctgaagag tgaggatacg gctacttatt attgtgcagc ggaagcattc    300

cgcccattca caccctccga cggggattgt accacagtgc ttggtataga ctactgggga    360

aaaggaacgc ctgttactgt gagcagc                                        387
```

<210> SEQ ID NO 24
<211> LENGTH: 387
<212> TYPE: DNA
<213> ORGANISM: Artificial Sequence
<220> FEATURE:
<223> OTHER INFORMATION: VHH for 01-9F-CDR-V11

<400> SEQUENCE: 24

```
caagtgcaac tggtagaatc tgggggggc agtgtacaag ctgggggcag cctgagactg     60

agctgtgtgg tgtctggcct gccctatgag agatactgtg tggcctggtt cagacaaggc    120

cctggcaagg agagagaggg ggtggctaga atcctgtctg atgccaccac aagctactct    180
```

-continued

```
gacacagtga agggcagatt caccatcagc aaggacaatg ccaagaacac cctgtacctg    240

cagatgaaca gcctgaagtc tgaggacaca gccacctact actgtgctgc tgaggccttc    300

agacccttca cccccctctga tgctgactgc accacagtgc tgggcattga ctactggggc    360

aagggcaccc ctgtgacagt gagctct                                        387


<210> SEQ ID NO 25
<211> LENGTH: 387
<212> TYPE: DNA
<213> ORGANISM: Artificial Sequence
<220> FEATURE:
<223> OTHER INFORMATION: VHH for 01-9F-CDR-V11-V11

<400> SEQUENCE: 25

gaggtgcagc tcgtggagag cggcgggggc ctggtgcaac ctggcgggag cctgagactg     60

agctgcgccg ctagcggcct gccctacagc agatactgcg tggcctggtt cagacaagcc    120

cccggcaagg gcctggaggg cgtggctaga atcctgagcg acgccaccac aagctacagc    180

gacaccgtga agggcagatt caccatcagc aaggacaacg ccaagaacag cctgtacctg    240

cagatgaaca gcctgagagc cgaggacacc gccgtgtact actgcgccgc cgaggccttc    300

agacccttca cccctagcga cgccgactgc accaccgtgc tgggcatcga ctactggggc    360

caaggcacca ccgtgaccgt gagcagc                                        387


<210> SEQ ID NO 26
<211> LENGTH: 699
<212> TYPE: DNA
<213> ORGANISM: Artificial Sequence
<220> FEATURE:
<223> OTHER INFORMATION: Constant region for heavy chain only antibodies

<400> SEQUENCE: 26

gagcccaaaa gctgtgacaa gacccacacc tgtcccccct gtcctgcccc tgagctcctt     60

gggggcccat ctgtgttcct gttccccccc aagcccaagg acaccctgat gatcagcaga    120

acccctgagg tgacctgtgt ggtggtggat gtgagccatg aggaccctga ggtgaagttc    180

aactggtatg tggatggggt ggaggtgcac aatgccaaga ccaagcctag agaggagcag    240

tacaacagca cctacagagt ggtgtctgtg ctgacagtgc tgcaccaaga ctggctgaat    300

ggcaaggagt acaagtgcaa ggtgagcaac aaggccctgc ctgcccccat tgagaagaca    360

atcagcaagg ccaaggggca gcctagagag ccccaagtgt acaccctgcc ccctagcaga    420

gaggagatga ccaagaacca agtgagcctg acctgcctgg tgaagggctt ctacccctct    480

gacattgctg tggagtggga gagcaatggg cagcctgaga acaactacaa gaccaccccc    540

cctgtgctgg actctgatgg cagcttcttc ctgtacagca agctgacagt ggacaagagc    600

agatggcagc aaggcaatgt gttcagctgc tctgtgatgc atgaggccct gcacaaccac    660

tacacacaga agagcctgag cctgagccct ggcaagtga                           699
```